(12) United States Patent  (10) Patent No.: US 8,436,040 B2
Binet et al.                 (45) Date of Patent:     May 7, 2013

(54) METHOD OF TREATING CONDITIONS INVOLVING PPAR-RECEPTORS WITH INDOLE COMPOUNDS

(75) Inventors: Jean Binet, Fontaine les Dijon (FR); Benaiessa Boubia, Saint Apollinaire (FR); Pierre Dodey, Fontaine les Dijon (FR); Christiane Legendre, Velard sur Ouche (FR); Martine Barth, Asnieres les Dijon (FR); Olivia Poupardin-Olivier, Varois et Chaignot (FR)

(73) Assignee: Laboratoires Fournier S.A., Dijon Cedex (FR)

( * ) Notice: Subject to any disclaimer, the term of this patent is extended or adjusted under 35 U.S.C. 154(b) by 382 days.

(21) Appl. No.: 12/795,148

(22) Filed: Jun. 7, 2010

(65) Prior Publication Data

US 2010/0286137 A1   Nov. 11, 2010

Related U.S. Application Data

(60) Division of application No. 12/039,324, filed on Feb. 28, 2008, now Pat. No. 7,795,297, which is a continuation of application No. PCT/FR2006/050818, filed on Aug. 29, 2006.

(30) Foreign Application Priority Data

Aug. 30, 2005  (FR) ...................................... 05 08858

(51) Int. Cl.
  *A61K 31/404*  (2006.01)
  *C07D 209/04*  (2006.01)
(52) U.S. Cl.
  USPC ............ 514/419; 548/469; 548/494; 514/415
(58) Field of Classification Search ................... 548/469, 548/494; 514/415, 419
  See application file for complete search history.

(56) References Cited

U.S. PATENT DOCUMENTS

| 5,622,983 | A | 4/1997 | Horwell et al. | |
| 5,631,281 | A | 5/1997 | Horwell et al. | |
| 6,288,103 | B1 | 9/2001 | Faull et al. | |
| 7,557,122 | B2 * | 7/2009 | Boubia et al. | 514/300 |
| 7,728,002 | B2 * | 6/2010 | Boubia et al. | 514/300 |
| 7,795,297 | B2 * | 9/2010 | Binet et al. | 514/419 |

FOREIGN PATENT DOCUMENTS

| WO | WO 97/28149 | 8/1997 |
| WO | WO 98/41092 | 9/1998 |
| WO | WO 99/07678 | 2/1999 |
| WO | WO 00/46196 | 8/2000 |
| WO | WO 01/60807 | 8/2001 |
| WO | WO 02/071827 | 9/2002 |
| WO | WO 2005/009958 A1 | 2/2005 |
| WO | WO 2006/060535 | 6/2006 |

OTHER PUBLICATIONS

International Search Report dated May 30, 2006 (Seven (7) pages).

* cited by examiner

*Primary Examiner* — Golam M M Shameem
(74) *Attorney, Agent, or Firm* — Crowell & Moring LLP

(57) ABSTRACT

Indole compounds corresponding to the formula (I):

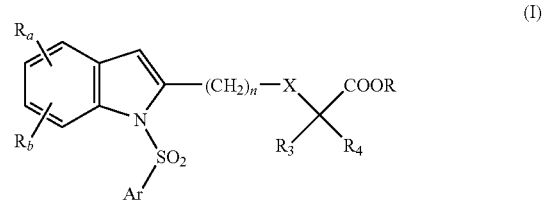

as defined in the claims, pharmaceutically acceptable addition salts of such compounds, pharmaceutical compositions containing such compounds, the process for their preparation, and their use as pharmacologically active substances, especially in the treatment of hypertriglyceridemia, hyperlipidemia, hypercholesterolemia, diabetes, endothelial dysfunction, cardiovascular disease, inflammatory disease and neurodegeneration.

3 Claims, No Drawings

METHOD OF TREATING CONDITIONS INVOLVING PPAR-RECEPTORS WITH INDOLE COMPOUNDS

CROSS REFERENCE TO RELATED APPLICATIONS

This application is a division of application Ser. No. 12/039,324, now, U.S. Pat. No. 7,795,297, which in turn was a continuation of international patent application no. PCT/FR2006/050818, filed Aug. 29, 2006, designating the United States of America and published in French on Mar. 8, 2007 as WO 2007/026097, the entire disclosure of which is incorporated herein by reference. Priority is claimed based on French Patent application no. FR 0508858, filed Aug. 30, 2005.

SPECIFICATION

The present invention relates to novel indole compounds, to the process for their manufacture and to their use in therapeutics for the prevention or treatment of pathological conditions involving a dysfunction of the PPAR-type nuclear receptors.

PRIOR ART

It is known in therapeutics that diseases of the cardiovascular system are an important risk factor for health. These diseases are frequently the consequence of a high cholesterol and/or triglyceride level, so it is important to keep these levels below values currently accepted by the medical profession.

In the case of cholesterol, it is particularly necessary to evaluate the amounts of cholesterol bound to the different lipoproteins so as to adapt the treatments to eliminate the cholesterol bound to the LDLs. The known families of compounds used to regulate these parameters include statins, which are HMG CoA reductase inhibitors and which make it possible essentially to treat excessively high LDL-cholesterol levels, and compounds of the fibrate family, which act by activating the PPARα (peroxisome proliferator activated receptor alpha) nuclear receptors and make it possible to lower the triglyceride and cholesterol levels.

Study of the PPAR nuclear receptors has led to the identification of 3 subtypes called PPARα, PPARγ and PPARδ. By binding to precise fragments of the DNA, these different receptors regulate the expression of target genes that code for proteins involved in the mechanisms for regulating the lipid metabolism.

Thus:
  PPARα is expressed essentially in the liver and is involved in the catabolism of the fatty acids by regulating the β- and ω-oxidation;
  PPARδ is expressed ubiquitously, but is present mainly in the kidneys, skeletal muscles, heart and intestine.

Like the other PPAR-type receptors, PPARδ forms a heterodimer with RXR (retinoid X receptor) and is then capable of binding to certain elements of the target genes of the nucleus and controlling the transcription factors. Among the different studies dedicated to this nuclear receptor, it has been demonstrated, for example, that the activation of PPARδ makes it possible to increase the HDL-cholesterol level in the db/db mouse (FEBS Letters (2000), 473, 333-336) and the insulin-dependent obese rhesus monkey and favors the efflux of cholesterol via Apo A1 in human THP-1 cells (Proc. Nat. Ac. Sci. USA (2001), 98, 5306-5311).

As a result of the study of these different nuclear receptors, it seems that compounds which are capable of activating either the PPARα receptors, or the PPARδ receptors, or both these receptors simultaneously, might have an extremely valuable pharmacological profile for the treatment of pathological conditions such as hyperlipidemia, hypercholesterolemia and the various diseases of the cardiovascular system that are the consequence of a metabolic syndrome.

The known documents of the prior art that mention such compounds include e.g. the document WO 97/28149, which describes PPARδ receptor agonists, the document WO 01/60807, which describes PPARα receptor agonists, or the documents WO 05/009958 and WO 06/060535, which propose indole compounds that act on the PPAR receptors.

Other references include documents WO 02/071827 and Bioorg. Med. Chem. Lett., 14 (11) pp 2759-2763 (06/2004), which describe RXR receptor modulating derivatives and their use in therapeutics for the treatment of pathological conditions involved in the metabolic syndrome.

Moreover, various indole compounds have been described elsewhere in the prior art. Thus:
  the documents WO 00/46196 and WO 99/07678 disclose compounds derived from indole-2-carboxylic acid for their anti-inflammatory activity;
  the document WO 98/41092 describes indole-2-carboxamide derivatives that act on pain.

SUMMARY OF THE INVENTION

The present invention relates to novel compounds derived from indole which are PPAR activators and are selected from
i) the compounds of the formula

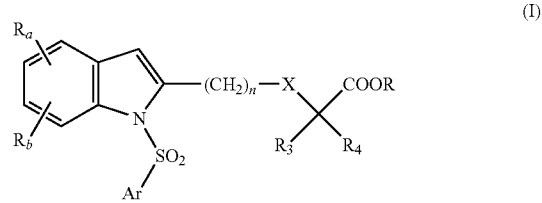

in which:
$R_a$ and $R_b$ independently are each a hydrogen atom, a halogen atom, a $C_1$-$C_6$ alkyl, $CF_3$, CN, CO—$R_2$ or $OR_2$ group or a phenyl group optionally substituted by a $C_1$-$C_4$ alkyl or $CF_3$ group;
$R_2$ is a $C_1$-$C_4$ alkyl or $CF_3$ group or a phenyl group optionally substituted by a $C_1$-$C_4$ alkyl or $CF_3$ group;
$R_3$ and $R_4$ independently are each a hydrogen atom or a $C_1$-$C_4$ alkyl group;
R is a hydrogen atom or a $C_1$-$C_3$ alkyl group;
n=1, 2 or 3;
X is a single bond, an oxygen atom or a sulfur atom; and
Ar is an aromatic or heteroaromatic ring selected from phenyl, naphthyl, quinolinyl, isoquinolinyl, pyridinyl, pyrazolyl, imidazolyl, isoxazolyl, thiazolyl, benzimidazolyl, benzothiazolyl, 2,1,3-benzothiadiazolyl, 3,4-dihydro-1,4-benzoxazinyl, 5,6,7,8-tetrahydronaphthalenyl, 1,2,3,4-tetrahydroquinolinyl, 1,2,3,4-tetrahydroisoquinolinyl, 1,2,3,4-tetrahydro-2-oxoquinolinyl, 3,4-dihydro-2H-benzopyranyl, indolyl, 2,3-dihydroindolyl, benzofuranyl, 2,3-dihydrobenzofuranyl, 1,3-benzodioxolyl, 1,4-benzodioxanyl and benzoxazolyl groups optionally substituted by one or more atoms or groups of atoms selected from halogen atoms and $C_1$-$C_6$ alkyl, phenyl, $CF_3$, CN, CO—$R_2$, $OR_2$, $SR_2$, NH—$COR_2$, morpholinyl, amino and 4-morpholinosulfonyl groups; and
ii) their pharmaceutically acceptable salts.

Preferred compounds according to the invention are the compounds of formula (I) given above in which at least one of the following conditions is met:
  at least one of $R_a$ and $R_b$ is other than a hydrogen atom;

Ar is a phenyl or nitrogen-containing heteroaromatic group selected from quinolinyl, isoquinolinyl, pyridinyl, pyrazolyl, imidazolyl, isoxazolyl, thiazolyl, benzimidazolyl, benzothiazolyl, 2,1,3-benzothiadiazolyl, 1,2,3,4-tetrahydroquinolinyl, 1,2,3,4-tetrahydroisoquinolinyl, 1,2,3,4-tetrahydro-2-oxoquinolinyl, indolyl, 2,3-dihydroindolyl and benzoxazolyl groups optionally substituted by one or more atoms or groups of atoms selected from halogen atoms and $C_1$-$C_6$ alkyl, $CF_3$, CN, CO—$R_2$, $OR_2$, $SR_2$, NH—$COR_2$, morpholinyl, amino and 4-morpholinosulfonyl groups; and n is equal to 1 or 2.

A first particular family of compounds according to the invention consists of the compounds of formula (I) in which X is an oxygen atom, and their pharmaceutically acceptable salts.

A second particular family of compounds according to the invention consists of the compounds of formula I in which X is a single bond and at least one of $R_3$ and $R_4$ is a $C_1$-$C_4$ alkyl group, and their pharmaceutically acceptable salts.

A third particular family of compounds according to the invention consists of the compounds of formula I in which X is a single bond and $R_3$ and $R_4$ are a hydrogen atom, and their pharmaceutically acceptable salts.

According to a second feature, the invention relates to the above-mentioned compounds for their use as pharmacologically active substances, and to the pharmaceutical compositions in which they are present.

The invention further relates to the use of at least one compound of formula (I) or one of its pharmaceutically acceptable salts as an active principle for the preparation of a drug intended for use in therapeutics, especially for combating hypercholesterolemia, hyperlipidemia, hypertriglyceridemia, dyslipidemia, insulin resistance, diabetes or obesity, as well as cardiovascular diseases which are the consequence of a serum lipoprotein imbalance. The compounds according to the invention are also useful as active principles of drugs intended for the prevention or treatment of diseases associated with an endothelial dysfunction, atherosclerosis, myocardial infarction, hypertension, cerebrovascular problems, certain inflammatory diseases, e.g. rheumatoid arthritis, and neurodegeneration, such as Alzheimer's disease or Parkinson's disease in particular.

DETAILED DESCRIPTION

In the present description, $C_1$-$C_n$ alkyl group (n being an integer) is understood as meaning a linear, branched or cyclic hydrocarbon chain having from 1 to n carbon atoms. By way of example, and without implying a limitation, a $C_1$-$C_6$ alkyl group can be a linear or branched group of the general formula $C_nH_{2n+1}$, such as methyl, ethyl, propyl, butyl, pentyl, hexyl, 1-methylethyl, 1-methylpropyl, 2-methylpropyl, 1,1-dimethylethyl, 1-methylbutyl, 1,1-dimethylpropyl, 1-methylpentyl or 1,1-dimethylbutyl, or a cyclic group of the general formula $C_nH_{2n-1}$, such as cyclopropyl, cyclobutyl, cyclopentyl, cyclohexyl or cyclopentylmethyl. Halogen is understood as meaning a fluorine, chlorine, bromine or iodine atom, fluorine and chlorine atoms being preferred.

The compounds of formula (I) in which R is a hydrogen atom are carboxylic acids, which can be used in the form of free acids or in the form of salts, said salts being obtained by combining the acid with a pharmaceutically acceptable, non-toxic mineral or organic base. Examples of mineral bases which can be used are sodium, potassium, magnesium or calcium hydroxides. Examples of organic bases which can be used are amines, amino alcohols, basic amino acids, such as lysine or arginine, or compounds carrying a quaternary ammonium group, e.g. betaine or choline.

The compounds of formula (I) in which the substituents $R_3$ and $R_4$ are different have a center of asymmetry. Where these compounds are concerned, the invention covers both the racemic compound and each of the optical isomers, considered separately.

Preferred compounds according to the invention are those in which Ar is a phenyl group or a nitrogen-containing heterocycle. Other preferred compounds are those in which $R_a$ is a halogen atom or a trifluoromethyl group, as well as those in which n is equal to 1 or 2.

The compounds according to the invention can be prepared by a first process that consists in a) using the SONOGASHIRA reaction (see, for example, Tet. Lett., 1975, 4467) to react a compound of the formula

(II)

in which:

$R_a$ and $R_b$ independently are each a hydrogen, fluorine, chlorine or bromine atom or a $C_1$-$C_6$ alkyl, $CF_3$, CN, CO—$R_2$ or $OR_2$ group; and $R_2$ is a $C_1$-$C_4$ alkyl or $CF_3$ group or a phenyl group optionally substituted by a $C_1$-$C_4$ alkyl or $CF_3$ group, with an acetylenic derivative of the formula

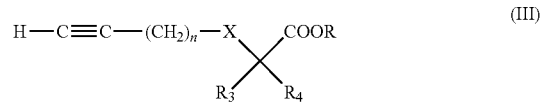

(III)

in which:

n=1, 2 or 3;

$R_3$ and $R_4$ independently are each a hydrogen atom or a $C_1$-$C_4$ alkyl group;

R is a $C_1$-$C_3$ alkyl group; and

X is a single bond, an oxygen atom or a sulfur atom, in the presence of cuprous iodide, a palladium-based catalyst, e.g. tetrakis-(triphenylphosphine)palladium, and an organic base, e.g. triethylamine, in a solvent, e.g. dimethylformamide (DMF), at a temperature between 0 and 60° C., for 2 to 24 hours, to give the compound of the formula

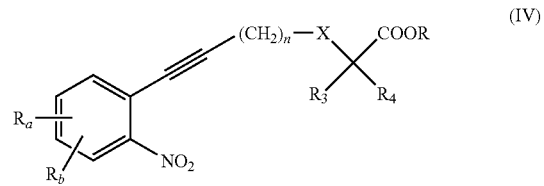

(IV)

in which:

$R_a$, $R_b$, n, X, $R_3$, $R_4$ and R are as defined in the starting compounds;

b) reducing the "nitro" group carried by the compound of formula IV above, e.g. by reaction with stannous chloride in the presence of ethanol, in a solvent, e.g. ethyl acetate, at a temperature close to room temperature, for 1 to 24 hours, to give the aniline of the formula

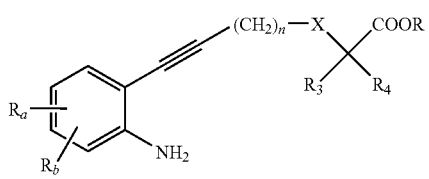

in which:
$R_a$, $R_b$, n, X, $R_3$, $R_4$ and R are as defined in the starting compound;
c) reacting the compound of formula V with an arylsulfonyl chloride of the formula Ar—SO$_2$—Cl    (VI)

in which:
Ar is an aromatic or heteroaromatic ring selected from phenyl, naphthyl, quinolinyl, isoquinolinyl, pyridinyl, pyrazolyl, imidazolyl, isoxazolyl, thiazolyl, benzimidazolyl, benzothiazolyl, 2,1,3-benzothiadiazolyl, 3,4-dihydro-1,4-benzoxazinyl, 5,6,7,8-tetrahydronaphthalenyl, 1,2,3,4-tetrahydroquinolinyl, 1,2,3,4-tetrahydroisoquinolinyl, 1,2,3,4-tetrahydro-2-oxoquinolinyl, 3,4-dihydro-2H-benzopyranyl, indolyl, 2,3-dihydroindolyl, benzofuranyl, 2,3-dihydrobenzofuranyl, 1,3-benzodioxolyl, 1,4-benzodioxanyl and benzoxazolyl groups optionally substituted by one or more atoms or groups of atoms selected from halogen atoms and $C_1$-$C_6$ alkyl, phenyl, CF$_3$, CN, CO—$R_2$, SR$_2$, OR$_2$, NH—COR$_2$, morpholinyl, amino and 4-morpholinosulfonyl groups, in the presence of pyridine, at room temperature, for 10 to 120 min, to give the compound of the formula

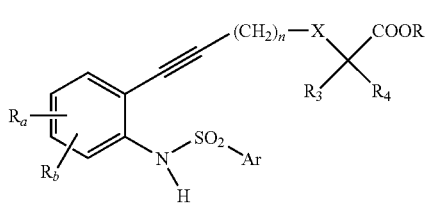

in which:
$R_a$, $R_b$, n, X, $R_3$, $R_4$, R and Ar are as defined in the starting compounds;
d) cyclizing the compound of formula VII, e.g. by reaction with copper(II) acetate (see, for example, J. Org. Chem., 2004, 69 (4), 1126-1136) in a solvent such as 1,2-dichloroethane, at a temperature close to the reflux temperature of the solvent, for 4 to 24 hours, to give the compound of the formula

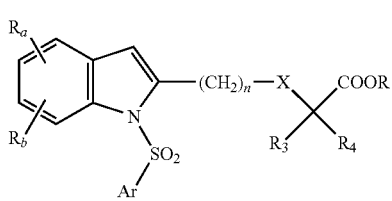

in which:
$R_a$, $R_b$, n, X, $R_3$, $R_4$, R and Ar are as defined in the starting compounds; and e) if necessary, hydrolyzing the ester group of the compound of formula Ia, e.g. by reaction with a mineral base such as sodium hydroxide or lithium hydroxide, by procedures well known to those skilled in the art, and then treating the product with acid to give the compound of formula I in its free acid form:

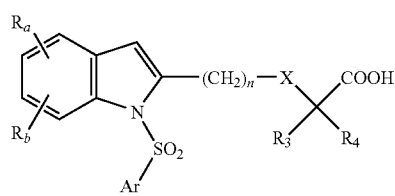

In a first variant of the preparative process, the compounds of formula I can be obtained by a series of reactions consisting in
a) carrying out a halogenation reaction, preferably an iodination, on an aniline of the formula

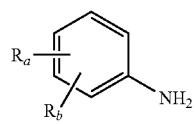

in which:
$R_a$ and $R_b$ independently are each a hydrogen atom, a halogen atom or a $C_1$-$C_6$ alkyl, CF$_3$, CN, CO—$R_2$ or OR$_2$ group; and
$R_2$ is a $C_1$-$C_4$ alkyl or CF$_3$ group or a phenyl group optionally substituted by a $C_1$-$C_4$ alkyl or CF$_3$ group,
with the aid of a halogenating agent, e.g. benzyltrimethylammonium dichloroiodate, in a solvent such as dichloromethane or methanol, at room temperature, for 5 to 24 hours, to give the compound of the formula

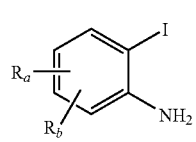

in which:
$R_a$ and $R_b$ are as defined in the starting compounds;
b) reacting the compound of formula IX with an acetylenic derivative of the formula $$H-C\equiv C-(CH_2)_n-X\underset{R_3\ R_4}{\diagdown}COOR \quad (III)$$

in which:
n=1, 2 or 3;
$R_3$ and $R_4$ independently are each a hydrogen atom or a $C_1$-$C_4$ alkyl group;
R is a $C_1$-$C_3$ alkyl group; and
X is a single bond, an oxygen atom or a sulfur atom, under conditions analogous to those described for step a) of the general process above, to give the compound of the formula

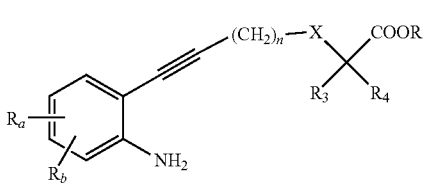

(V)

in which:
$R_a$, $R_b$, n, X, $R_3$, $R_4$ and R are as defined in the starting compound;
c) cyclizing the compound of formula V above, under conditions analogous to those described for carrying out step (d) of the general process above, to give the indole compound of the formula

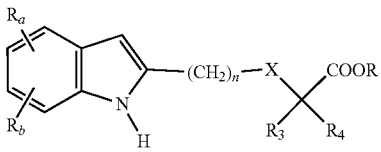

(X)

in which:
$R_a$, $R_b$, n, X, $R_3$, $R_4$ and R are as defined in the starting compound;
d) reacting the compound of formula (X) above with an arylsulfonyl chloride of the formula

Ar—SO$_2$—Cl    (VI)

in which:
Ar is an aromatic or heteroaromatic ring selected from phenyl, naphthyl, quinolinyl, isoquinolinyl, pyridinyl, pyrazolyl, imidazolyl, isoxazolyl, thiazolyl, benzimidazolyl, benzothiazolyl, 2,1,3-benzothiadiazolyl, 3,4-dihydro-1,4-benzoxazinyl, 5,6,7,8-tetrahydronaphthalenyl, 1,2,3,4-tetrahydroquinolinyl, 1,2,3,4-tetrahydroisoquinolinyl, 1,2,3,4-tetrahydro-2-oxoquinolinyl, 3,4-dihydro-2H-benzopyranyl, indolyl, 2,3-dihydroindolyl, benzofuranyl, 2,3-dihydrobenzofuranyl, 1,3-benzodioxolyl, 1,4-benzodioxanyl and benzoxazolyl groups optionally substituted by one or more atoms or groups of atoms selected from halogen atoms and $C_1$-$C_6$ alkyl, phenyl, CF$_3$, CN, CO—R$_2$, SR$_2$, OR$_2$, NH—COR$_2$, morpholinyl, amino and 4-morpholinosulfonyl groups,
in a solvent, e.g. dimethylformamide, at room temperature, for 1 to 12 hours, generally after activation of the indole compounds of formula (X) with sodium hydride, to give the compound of formula (Ia):

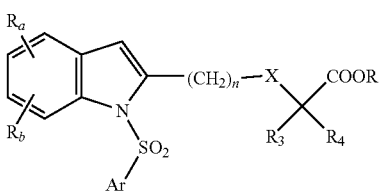

(Ia)

in which:
$R_a$, $R_b$, n, X, $R_3$, $R_4$, R and Ar are as defined in the starting compounds; and e) if necessary, hydrolyzing the ester group of the compound of formula Ia, e.g. by reaction with a mineral base such as sodium hydroxide or lithium hydroxide, by procedures well known to those skilled in the art, and then treating the product with acid to give the compound of formula I in its free acid form:

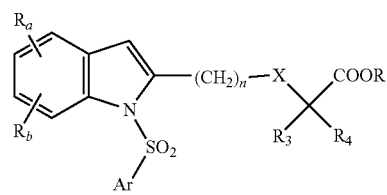

(Ib)

In a second variant of the preparative process, the compounds of formula I can be obtained by a series of reactions consisting in
a) reacting the compound of formula IX:

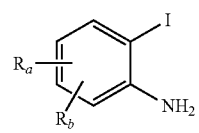

(IX)

in which:
$R_a$ and $R_b$ independently are each a hydrogen, fluorine, chlorine or bromine atom or a $C_1$-$C_6$ alkyl, CF$_3$, CN, CO—R$_2$ or OR$_2$ group; and
$R_2$ is a $C_1$-$C_4$ alkyl or CF$_3$ group or a phenyl group optionally substituted by a $C_1$-$C_4$ alkyl or CF$_3$ group,
with an arylsulfonyl chloride of the formula Ar—SO$_2$—Cl    (VI)

in which:
Ar is an aromatic or heteroaromatic ring selected from phenyl, naphthyl, quinolinyl, isoquinolinyl, pyridinyl, pyrazolyl, imidazolyl, isoxazolyl, thiazolyl, benzimidazolyl, benzothiazolyl, 2,1,3-benzothiadiazolyl, 3,4-dihydro-1,4-benzoxazinyl, 5,6,7,8-tetrahydronaphthalenyl, 1,2,3,4-tetrahydroquinolinyl, 1,2,3,4-tetrahydroisoquinolinyl, 1,2,3,4-tetrahydro-2-oxoquinolinyl, 3,4-dihydro-2H-benzopyranyl, indolyl, 2,3-dihydroindolyl, benzofuranyl, 2,3-dihydrobenzofuranyl, 1,3-benzodioxolyl, 1,4-benzodioxanyl and benzoxazolyl groups optionally substituted by one or more atoms or groups of atoms selected from halogen atoms and $C_1$-$C_6$ alkyl, phenyl, CF$_3$, CN, CO—R$_2$, OR$_2$, SR$_2$, NH—COR$_2$, morpholinyl, amino and 4-morpholinosulfonyl groups,
in a solvent, e.g. dimethylformamide, at room temperature, for 1 to 12 hours, to give the compound of the formula

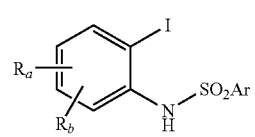

(XI)

in which:
$R_a$, $R_b$ and Ar are as defined in the starting compounds;

b) reacting the compound of formula XI with an acetylenic derivative of the formula

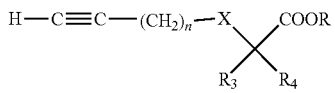 (III)

in which:
n=1, 2 or 3;
$R_3$ and $R_4$ independently are each a hydrogen atom or a $C_1$-$C_4$ alkyl group;
R is a $C_1$-$C_3$ alkyl group; and
X is a single bond, an oxygen atom or a sulfur atom, under conditions analogous to those described for step a) of the general process above, to give the compound of the formula

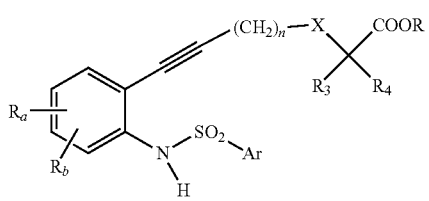 (VII)

in which:
$R_a$, $R_b$, n, X, $R_3$, $R_4$, R and Ar are as defined in the starting compounds;
c) cyclizing the compound of formula VII above, under conditions analogous to those described for carrying out step (d) of the general process above, to give the indole compound of the formula

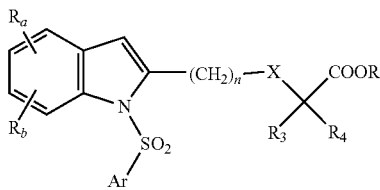 (Ia)

in which:
$R_a$, $R_b$, n, X, $R_3$, $R_4$, R and Ar are as defined in the starting compounds; and
d) if necessary, hydrolyzing the ester group of the compound of formula Ia, e.g. by reaction with a mineral base such as sodium hydroxide or lithium hydroxide, by procedures well known to those skilled in the art, and then treating the product with acid to give the compound of formula I in its free acid form:

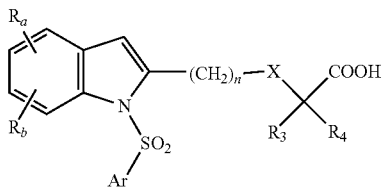 (Ib)

During this last process, it is possible to carry out the two steps b) and c) in a single operation.

The compounds of formula I according to the invention in which $R_a$ (this process also applies to $R_b$) is an optionally substituted phenyl ring can be obtained from the halogenated compound of the formula

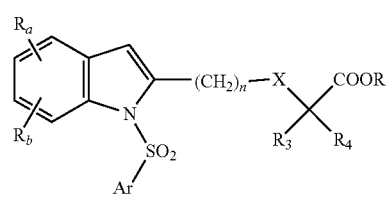 (Ic)

in which:
$R_a$ is a halogen atom, preferably a bromine atom, $R_b$ is a hydrogen atom, a fluorine or chlorine atom or a $C_1$-$C_6$ alkyl, $CF_3$, CN, CO—$R_2$ or $OR_2$ group;
$R_2$ is a $C_1$-$C_4$ alkyl or $CF_3$ group or a phenyl group optionally substituted by a $C_1$-$C_4$ alkyl or $CF_3$ group;
$R_3$ and $R_4$ independently are each a hydrogen atom or a $C_1$-$C_4$ alkyl group;
R is a $C_1$-$C_3$ alkyl group;
n=1, 2 or 3;
X is a single bond, an oxygen atom or a sulfur atom; and
Ar is an aromatic or heteroaromatic ring selected from phenyl, naphthyl, quinolinyl, isoquinolinyl, pyridinyl, pyrazolyl, imidazolyl, isoxazolyl, thiazolyl, benzimidazolyl, benzothiazolyl, 2,1,3-benzothiadiazolyl, 3,4-dihydro-1,4-benzoxazinyl, 5,6,7,8-tetrahydronaphthalenyl, 1,2,3,4-tetrahydroquinolinyl, 1,2,3,4-tetrahydroisoquinolinyl, 1,2,3,4-tetrahydro-2-oxoquinolinyl, 3,4-dihydro-2H-benzopyranyl, indolyl, 2,3-dihydroindolyl, benzofuranyl, 2,3-dihydrobenzofuranyl, 1,3-benzodioxolyl, 1,4-benzodioxanyl and benzoxazolyl groups optionally substituted by one or more atoms or groups of atoms selected from chlorine and fluorine atoms and $C_1$-$C_6$ alkyl, phenyl, $CF_3$, CN, CO—$R_2$, $OR_2$, $SR_2$, NH—$COR_2$, morpholinyl, amino and 4-morpholinosulfonyl groups,
with a phenylboronic acid of the formula

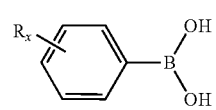 (XII)

in which:
$R_x$ is a hydrogen atom or a $C_1$-$C_4$ alkyl or $CF_3$ group,
according to a SUZUKI reaction (see, for example, Chem. Rev., 1995, 95, 2457), in the presence of tetrakis(triphenylphosphine)palladium and a base, e.g. sodium carbonate, in a solvent, e.g. a mixture of tetrahydrofuran, methanol and water, at a temperature between 30° C. and the reflux temperature of the solvent, for 5 to 24 hours, to give a compound of formula Id:

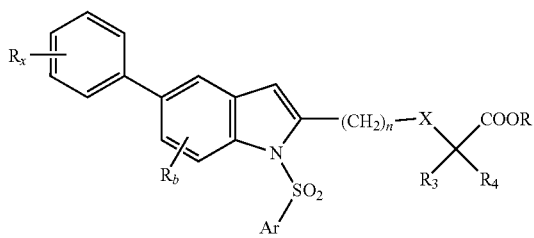

(Id)

in which:
R, $R_b$, $R_x$, X, $R_3$, $R_4$, n and Ar are as defined in the starting compounds.

The compounds of the invention in the form of salts of an acid of formula Ib with a mineral or organic base can be obtained in conventional manner by using the methods well known to those skilled in the art, e.g. by mixing stoichiometric amounts of the acid and the base in a solvent, e.g. water or a water/alcohol mixture, and then lyophilizing the solution obtained.

In some of the reaction steps described above, it is possible advantageously to replace the traditional heating methods, well known to those skilled in the art, by microwave heating using reactors adapted to this mode of reaction. In this case, those skilled in the art will understand that the "heating" times will be considerably reduced compared with the times required for conventional heating.

The following Examples of the preparation of compounds of formula (I) will afford a better understanding of the invention.

In these Examples, which do not limit the scope of the invention, 'Preparation' denotes the Examples that describe the synthesis of intermediates, and 'Example' denotes those that describe the synthesis of compounds of formula (I) according to the invention. Among the abbreviations, 'mM' denotes millimol. The melting points are measured on a Koffler bench or with a Mettler apparatus and the nuclear magnetic resonance spectral values are characterized by the chemical shift calculated relative to TMS, by the number of protons associated with the signal and by the shape of the signal (s for singlet, d for doublet, dd for doublet of doublets, t for triplet, q for quadruplet, quin for quintuplet, m for multiplet). The operating frequency and the solvent used are indicated for each compound. Room temperature is 20° C.±5° C. In certain cases, the structure of the compounds was confirmed by mass spectroscopy following liquid chromatography (LC/MS coupling); the measurements were made on an UPTISPHERE HDO column with an HDO phase (column: 50×2 mm×3 μm), flow rate: 0.6 ml/min (split: ⅓), mobile phase: A=$H_2O$+0.5% TFA (trifluoroacetic acid), B=acetonitrile+0.5% TFA (gradient programming: B=10 to 90% in 7 min, then plateau at 90% for 2 min, then return to 10% in 1 min and stabilization at 10% for 3 min); working temperature: 45° C.; UV detection: 210 to 260 nm. The mass spectrum is obtained by ESI+, spray: 3500 V, source block temperature: 130° C., desolvation: 230° C., desolvation gas: 600 l/h, cone gas: 100 l/h, voltage: 10 V/30 V/60 V. The result is expressed by the mass (m/z) and the retention time (Tr).

Preparation 1

5-(5-Chloro-2-nitrophenyl)-4-pentynoic acid methyl ester 35.5 g (125 mM) of 4-chloro-2-iodo-1-nitrobenzene, 510 ml of triethylamine, 2.88 g (2.5 mM) of tetrakis(triphenylphosphine)palladium, 0.72 g of cuprous iodide and 50 ml of dimethylformamide (DMF) are mixed. 14 g (125 mM) of the methyl ester of 4-pentynoic acid are then added at room temperature, with stirring, and the reaction mixture is stirred for 24 hours at room temperature. 100 ml of toluene are added and the solvents are driven off under reduced pressure. The evaporation residue is taken up with 150 ml of ethyl acetate and 80 ml of N hydrochloric acid. The organic phase is separated off, washed with water and then dried over magnesium sulfate and concentrated under reduced pressure. The brown oil obtained is purified by chromatography on silica gel using a cyclohexane/ethyl acetate mixture (9/1; v/v) as the eluent to give 21.5 g of the expected product in the form of a yellow solid (yield=65%).
M.p.=75-78° C.

Preparation 2

5-(2-Amino-5-chlorophenyl)-4-pentynoic acid methyl ester 90.6 g (400 mM) of stannous chloride, 70 ml of ethyl acetate and 22 ml of ethanol are introduced into a round-bottomed flask. This mixture is stirred for 15 min at room temperature and a solution of 21.5 g (80 mM) of the compound obtained according to Preparation 1 is then added slowly. The reaction mixture is stirred for 24 hours at room temperature and then poured into a mixture of 200 g of ice and 200 ml of N sodium hydroxide solution. The mixture obtained is extracted twice with 200 ml of ethyl acetate; the combined organic phases are washed with water, dried over magnesium sulfate and concentrated under reduced pressure. The oil obtained is purified by chromatography on silica gel using a cyclohexane/ethyl acetate mixture (80/20; v/v) as the eluent to give 9.1 g of the expected compound in the form of an orange-yellow solid (yield=30%).
M.p.=67° C.

Preparation 3

[5-Chloro-2-(phenylsulfonylamino)phenyl]-4-pentynoic acid methyl ester

A solution of 1.2 g (5 mM) of the compound obtained according to Preparation 2 in 15 ml of pyridine is prepared and 0.77 ml (6 mM) of benzenesulfonyl chloride is added. The mixture is stirred for 1 hour at room temperature and then concentrated under reduced pressure. The residual oil is purified by chromatography on silica gel using a cyclohexane/ethyl acetate mixture (8/2; v/v) as the eluent to give 1.8 g of the expected compound in the form of a beige solid (yield=95%).
$^1$H NMR (DMSOd$_6$, 300 MHz) δ=2.56 (s, 4H), 3.65 (s, 3H), 7.28-7.36 (m, 3H), 7.54-7.72 (m, 5H), 9.69 (s, 1H).

Example 1

5-Chloro-1-(phenylsulfonyl)-1H-indole-2-propanoic acid methyl ester

A solution of 300 mg (0.79 mM) of the ester obtained according to Preparation 3 in 35 ml of 1,2-dichloroethane is prepared, 15 mg (0.08 mM) of copper (cupric) acetate are added and the mixture is refluxed for 24 hours, with stirring. The solvent is then driven off under reduced pressure and the residual viscous solid is purified by chromatography on silica gel using a toluene/ethyl acetate mixture (9/1; v/v) as the eluent to give 230 mg of the compound obtained in the form of a yellow solid (yield=77%).
M.p.=93-96° C.

Example 2

5-Chloro-1-(phenylsulfonyl)-1H-indole-2-propanoic acid 180 mg (0.46 mM) of the ester obtained according to Example 1 are mixed with 16 ml of THF and 4 ml of water, and 20 mg (0.48 mM) of lithium hydroxide (LiOH.1H$_2$O) are added. The mixture is stirred for 3 hours at room temperature and then concentrated under reduced pressure. The evaporation residue is taken up in 10 ml of water and the solution is acidified with 1 N hydrochloric acid solution. The white precipitate is extracted with ethyl acetate and the organic phase is separated off, dried over magnesium sulfate and concentrated under reduced pressure to give 160 mg of the expected product in the form of a yellow solid (yield=93%).
M.p.=165-168° C.

Example 2a

5-Chloro-1-(phenylsulfonyl)-1H-indole-2-propanoic acid sodium salt 114 mg (0.313 mM) of the acid obtained according to Example 2 are mixed with 10 ml of water and 0.313 ml of N sodium hydroxide solution. A few drops of methanol are added, with stirring, to give a solution. The mixture is stirred for 15 min at room temperature and then partially concentrated under reduced pressure. The residual solution is then filtered and lyophilized to give 115 mg of the expected salt in the form of a fine white powder (yield=95%).
M.p.≧250° C.

Preparation 4

2-Iodo-4-(trifluoromethyl)aniline

A solution of 5 g (31 mM) of 4-(trifluoromethyl)aniline in 90 ml of methanol and 30 ml of dichloromethane is prepared and 3.56 g (35.6 mM) of calcium carbonate are added. 14.9 g (42.7 mM) of trimethylbenzylammonium dichloroiodide are then added in portions at room temperature, with stirring. The reaction medium is stirred for 24 hours at room temperature and then filtered to remove the mineral salts. The filtrate is concentrated under reduced pressure and the crude product is purified by chromatography on silica gel using a cyclohexane/ethyl acetate mixture (8/2; v/v) as the eluent to give 6.65 g of the expected compound in the form of an orange oil (yield=75%).
$^1$H NMR (CDCl$_3$, 300 MHz) δ=5.0 (s, 2H), 6.82 (d, J=5.5 Hz, 1H), 7.38 (dd, J=5.5 Hz, 1.3 Hz, 1H), 7.79 (d, J=1.3 Hz, 1H).

Preparation 5

5-[2-Amino-5-(trifluoromethyl)phenyl]-4-pentynoic acid methyl ester

A solution of 1.5 g (5.23 mM) of the compound obtained according to Preparation 4, 0.644 g (5.75 mM) of methyl 4-pentynoate and 90 mg (0.13 mM) of dichlorobis(triphenylphosphine)palladium in 1 ml of dimethylformamide and 2 ml of diethylamine is prepared and 50 mg (0.26 mM) of cuprous iodide are added. The reaction mixture is irradiated in a microwave oven at 120° C. for 10 minutes. The solvents are then driven off under reduced pressure and the evaporation residue is purified by chromatography on silica gel using a cyclohexane/ethyl acetate mixture (8/2; v/v) as the eluent to give 1.16 g of the expected compound in the form of an orange oil (yield=82%).
$^1$H NMR (DMSOd$_6$, 300 MHz) δ=2.65-2.75 (m, 4H), 3.64 (s, 3H), 5.99 (s, 2H), 6.78 (d, J=8.3 Hz, 1H), 7.31 (d, J=8.3 Hz, 1H), 7.33 (s, 1H).

Preparation 6

5-(Trifluoromethyl)-1H-indole-2-propanoic acid methyl ester

A solution of 1.16 g (4.28 mM) of the ester obtained according to Preparation 5 in 5 ml of 1,2-dichloroethane is prepared and 1.3 g (6.4 mM) of cupric acetate are added. The reaction mixture is irradiated in a microwave oven at 150° C. for 30 minutes and then cooled and filtered. The filtrate is concentrated under reduced pressure to give 1 g of the expected compound in the form of a brown solid (yield=86%).
M.p.=106-108° C.

Example 3

1-(Phenylsulfonyl)-5-(trifluoromethyl)-1H-indole-2-propanoic acid methyl ester 0.18 g (4.6 mM) of sodium hydride (60% dispersion in oil) is added at 0° C. to a solution of 1 g (3.69 mM) of the ester obtained according to Preparation 6. This mixture is stirred for 15 min and 0.98 g (5.5 mM) of benzenesulfonyl chloride is added, still at 0° C. The mixture is stirred for 30 min at room temperature and 100 ml of 15% aqueous ammonium chloride solution are then added. The mixture is extracted 3 times with 50 ml of dichloromethane. The combined organic phases are dried over magnesium sulfate and concentrated under reduced pressure. The residual oil is purified by chromatography on silica gel using a cyclohexane/ethyl acetate mixture (8/2; v/v) as the eluent to give 0.95 g of the expected product in the form of an oil, which crystallizes into orange stars (yield=62%).
M.p.=81-83° C.

Example 4

1-(Phenylsulfonyl)-5-(trifluoromethyl)-1H-indole-2-propanoic acid

By following a procedure analogous to Example 2 starting from the compound obtained according to Example 3, the expected product is obtained in the form of a beige solid (yield 85%).
M.p.=170-172° C.

Preparation 7

5-(2-Amino-5-bromophenyl)-4-pentynoic acid methyl ester

By following a procedure analogous to Preparation 5 starting from 4-bromo-2-iodoaniline, the expected compound is obtained in the form of a yellow oil (yield=23%).

¹H NMR (DMSOd₆, 250 MHz) δ=2.61-2.74 (m, 4H), 3.63 (s, 3H), 5.46 (s, 2H), 6.63 (dd, J=8.3 Hz, 0.7 Hz, 1H), 7.1-7.2 (m, 2H).

Preparation 8

5-Bromo-1H-indole-2-propanoic acid methyl ester

By following a procedure analogous to Preparation 6 starting from the compound obtained according to Preparation 7, the expected compound is obtained in the form of a brown solid (yield=98%).

¹H NMR (DMSOd₆, 250 MHz) δ=2.75 (t, J=7.3 Hz, 2H), 2.98 (t, J=7.2 Hz, 2H), 3.60 (s, 3H), 6.14 (s, 1H), 7.1 (dd, J=8.5 Hz, 1.9 Hz, 1H), 7.2 (d, J=8.5 Hz, 1H), 7.58 (d, J=1.9 Hz, 1H), 11.1 (s, 1H).

Example 5

5-Bromo-1-(phenylsulfonyl)-1H-indole-2-propanoic acid methyl ester

By following a procedure analogous to Example 3 starting from the compound obtained according to Preparation 8, the expected compound is obtained in the form of a light brown solid (yield=25%).
M.p.=109-113° C.

Example 6

5-Bromo-1-(phenylsulfonyl)-1H-indole-2-propanoic acid

By following a procedure analogous to Example 2 starting from the compound obtained according to Example 5, the expected compound is obtained in the form of a beige solid (yield=81%).
M.p.=188-190° C.

Example 7

1-(Phenylsulfonyl)-5-[4-(trifluoromethyl)phenyl]-1H-indole-2-propanoic acid methyl ester A solution of 0.5 g (1.18 mM) of the ester obtained according to Example 5 and 0.68 g (0.59 mM) of tetrakis(triphenylphosphine)palladium in 5 ml of THF is prepared and a solution of 0.84 g (4.4 mM) of 4-(trifluoromethyl)phenylboronic acid in 2.5 ml of methanol is added, followed by a solution of 282 mg (2.6 mM) of sodium carbonate in 1 ml of water. The mixture is then stirred at the reflux temperature of the solvent for 24 hours. After it has returned to room temperature, the mixture is diluted with 20 ml of dichloromethane and dried over magnesium sulfate. The solution obtained is concentrated under reduced pressure and the evaporation residue is taken up in solution in 50 ml of ethyl ether. The solution obtained is washed 3 times with 15 ml of 1 N sodium hydroxide solution and then with water until the washings are neutral, dried over magnesium sulfate and concentrated under reduced pressure. The residual oil is purified by chromatography on silica gel using a cyclohexane/ethyl acetate mixture (85/15; v/v) as the eluent to give 57 mg of the expected compound in the form of a beige oil (yield=10%).

¹H NMR (DMSOd₆, 250 MHz) δ=2.84 (t, J=7.1 Hz, 2H), 3.32 (d, J=7.2 Hz, 2H), 3.62 (s, 3H), 6.68 (s, 1H), 7.56-7.71 (m, 5H), 7.78-7.91 (m, 6H), 8.13 (d, 1H).

Example 8

1-(Phenylsulfonyl)-5-[4-(trifluoromethyl)phenyl]-1H-indole-2-propanoic acid

By following a procedure analogous to Example 2 starting from the compound obtained according to Example 7, the expected product is obtained in the form of a yellow solid (yield=76%).
M.p.=162° C.

Preparation 9

5-(2-Nitrophenyl)-4-pentynoic acid methyl ester

By following a procedure analogous to Preparation 1 starting from 1-iodo-2-nitrobenzene, the expected product is obtained in the form of a yellow solid (yield=53%).
M.p.=44-46° C.

Preparation 10

6-(5-Chloro-2-nitrophenyl)-5-hexynoic acid methyl ester

By following a procedure analogous to Preparation 1 starting from the methyl ester of 5-hexynoic acid, the expected product is obtained in the form of a brown oil (yield=73%).

¹H NMR (DMSOd₆, 250 MHz) δ=1.81 (m, 2H), 2.54 (m, 4H), 3.60 (s, 3H), 7.69 (dd, 1H), 7.81 (d, 1H), 8.09 (d, 1H).

Preparation 11

7-(5-Chloro-2-nitrophenyl)-6-heptynoic acid methyl ester

By following a procedure analogous to Preparation 1 starting from the methyl ester of 6-heptynoic acid, the expected product is obtained in the form of a brown oil (yield=98%).

¹H NMR (DMSOd₆, 250 MHz) δ=1.34-1.73 (m, 4H), 2.36 (t, 2H), 2.53 (t, 2H), 3.59 (s, 3H), 7.66 (dd, 1H), 7.79 (d, 1H), 8.09 (d, 1H).

Preparation 12

5-(2-Aminophenyl)-4-pentynoic acid methyl ester

By following a procedure analogous to Preparation 2 starting from the compound obtained according to Preparation 9, the expected product is obtained in the form of a colorless oil (yield=53%).

¹H NMR (DMSOd₆, 250 MHz) δ=2.67 (m, 4H), 3.63 (s, 3H), 5.25 (s, 2H), 6.46 (m, 1H), 6.65 (dd, 1H), 7.02 (m, 2H).

Preparation 13

6-(2-Amino-5-chlorophenyl)-5-hexynoic acid methyl ester

By following a procedure analogous to Preparation 2 starting from the compound obtained according to Preparation 10, the expected product is obtained in the form of a yellow solid (yield=41%).

¹H NMR (DMSOd₆, 250 MHz) δ=1.83 (m, 2H), 2.48 (m, 4H), 3.59 (s, 3H), 5.40 (s, 2H), 6.67 (d, 1H), 7.03 (dd, 1H), 7.08 (d, 1H).

Preparation 14

7-(2-Amino-5-chlorophenyl)-6-heptynoic acid methyl ester

By following a procedure analogous to Preparation 2 starting from the compound obtained according to Preparation 11, the expected product is obtained in the form of a yellow solid (yield=68%).
M.p.=66° C.

Preparation 15

5-(2-Amino-5-fluorophenyl)-4-pentynoic acid methyl ester

By following a procedure analogous to Preparation 5 starting from 4-fluoro-2-iodoaniline, the expected product is obtained in the form of a brown solid (yield=45%).
$^1$H NMR (DMSOd$_6$, 300 MHz) δ=2.6-2.75 (m, 4H), 3.63 (s, 3H), 5.16 (s, 2H), 6.6-6.7 (m, 1H), 6.8-6.85 (m, 2H).

Preparation 16

5-(2-Amino-4,5-dichlorophenyl)-4-pentynoic acid methyl ester

By following a procedure analogous to Preparation 5 starting from 4,5-dichloro-2-iodoaniline, the expected product is obtained in the form of beige crystals (yield=87%).
$^1$H NMR (DMSOd$_6$, 300 MHz) δ=2.65-2.75 (m, 4H), 3.63 (s, 3H), 5.70 (s, 2H), 6.87 (s, 1H), 7.24 (s, 1H).

Preparation 17

5-(2-Amino-5,6-dichlorophenyl)-4-pentynoic acid methyl ester

By following a procedure analogous to Preparation 5 starting from 3,4-dichloro-2-iodoaniline, the expected product is obtained in the form of a colorless oil (yield=49%).
$^1$H NMR (DMSOd$_6$, 300 MHz) δ=2.6-2.8 (m, 4H), 3.63 (s, 3H), 5.74 (s, 2H), 6.65 (d, 1H), 7.20 (d, 1H).

Preparation 18

5-[2-Amino-4-(trifluoromethyl)phenyl]-4-pentynoic acid methyl ester

By following a procedure analogous to Preparation 5 starting from 5-(trifluoromethyl)-2-iodoaniline, the expected product is obtained in the form of orange crystals (yield=71%).
M.p.=42° C.

Preparation 19

5-(2-Amino-5-acetylphenyl)-4-pentynoic acid methyl ester

By following a procedure analogous to Preparation 5 starting from 4-amino-3-iodoacetophenone, the expected product is obtained in the form of a yellow solid (yield=39%).
$^1$H NMR (DMSOd$_6$, 300 MHz) δ=2.39 (s, 3H), 2.65-2.75 (m, 4H), 3.64 (s, 3H), 6.15 (s, 2H), 6.69 (d, 1H), 7.64 (dd, 1H), 7.69 (d, 1H).

Preparation 20

5-(2-Amino-4-chloro-5-fluorophenyl)-4-pentynoic acid methyl ester

By following a procedure analogous to Preparation 5 starting from 5-chloro-4-fluoro-2-iodoaniline, the expected product is obtained in the form of brown crystals (yield=81%).
M.p.=67-68° C.

Preparation 21

5-(2-Amino-5-cyanophenyl)-4-pentynoic acid methyl ester

By following a procedure analogous to Preparation 5 starting from 4-amino-3-iodobenzonitrile, the expected product is obtained in the form of a colorless oil (yield=52%).
$^1$H NMR (DMSOd$_6$, 300 MHz) δ=2.65-2.75 (m, 4H), 3.63 (s, 3H), 6.27 (s, 2H), 6.73 (d, 1H), 7.38 (dd, 1H), 7.46 (d, 1 Hz, 1H).

Preparation 22

5-(2-Amino-5-benzoylphenyl)-4-pentynoic acid methyl ester

By following a procedure analogous to Preparation 5 starting from 4-amino-3-iodobenzophenone, the expected product is obtained in the form of a yellow oil (yield=54%).
$^1$H NMR (DMSOd$_6$, 300 MHz) δ=2.63-2.73 (m, 4H), 3.62 (s, 3H), 6.28 (s, 2H), 6.75 (d, 1H), 7.47-7.61 (m, 7H).

Preparation 23

5-(2-Amino-3,5-dichlorophenyl)-4-pentynoic acid methyl ester

By following a procedure analogous to Preparation 5 starting from 2,4-dichloro-6-iodoaniline, the expected product is obtained in the form of a dark-colored oil (yield=87%).
$^1$H NMR (DMSOd$_6$, 300 MHz) δ=2.6-2.8 (m, 4H), 3.64 (s, 3H), 5.55 (s, 2H), 7.13 (d, 1H), 7.33 (d, 1H).

Preparation 24

5-[2-[(Phenylsulfonyl)amino]phenyl]-4-pentynoic acid methyl ester

By following a procedure analogous to Preparation 3 starting from the compound obtained according to Preparation 12, the expected product is obtained in the form of a colorless oil (yield=82%).
$^1$H NMR (DMSOd$_6$, 300 MHz) δ=2.57 (s, 4H), 3.65 (s, 3H), 7.13 (m, 1H), 7.22-7.28 (m, 3H), 7.52-7.62 (m, 3H), 7.71 (dd, 2H), 9.49 (s, 1H).

Preparation 25

5-[5-Chloro-2-[[(4-methylphenyl)sulfonyl]amino]phenyl]-4-pentynoic acid methyl ester By following a procedure analogous to Preparation 3 starting from p-toluenesulfonyl chloride, the expected product is obtained in the form of a yellow oil (yield=85%).

¹H NMR (DMSOd₆, 250 MHz) δ=2.35 (s, 3H), 2.56 (s, 4H), 3.65 (s, 3H), 7.31 (m, 5H), 7.59 (d, 2H), 9.57 (s, 1H).

Preparation 26

5-[5-Chloro-2-[[(2,3-dichlorophenyl)sulfonyl]amino]phenyl]-4-pentynoic acid methyl ester By following a procedure analogous to Preparation 3 starting from 2,3-dichlorobenzenesulfonyl chloride, the expected product is obtained in the form of a yellow solid (yield=85%).
M.p.=64° C.

Preparation 27

5-[5-Chloro-2-[[(3-methylphenyl)sulfonyl]amino]phenyl]-4-pentynoic acid methyl ester By following a procedure analogous to Preparation 3 starting from m-toluenesulfonyl chloride, the expected product is obtained in the form of a beige solid (yield=82%).
M.p.=69° C.

Preparation 28

5-[5-Chloro-2-[[(2,4-dichlorophenyl)sulfonyl]amino]phenyl]-4-pentynoic acid methyl ester By following a procedure analogous to Preparation 3 starting from 2,4-dichlorobenzenesulfonyl chloride, the expected product is obtained in the form of a colorless oil (yield=96%).
¹H NMR (DMSOd₆, 300 MHz) δ=2.56 (s, 4H), 3.64 (s, 3H), 7.27 (dd, J=8.4, 0.78 Hz, 1H), 7.36 (m, 2H), 7.58 (dd, 1H), 7.84 (d, 1H), 7.89 (s, 1H), 10.06 (s, 1H).

Preparation 29

5-[5-Chloro-2-[[[4-(trifluoromethyl)phenyl]sulfonyl]amino]phenyl]-4-pentynoic acid methyl ester By following a procedure analogous to Preparation 3 starting from 4-(trifluoromethyl)benzenesulfonyl chloride, the expected product is obtained in the form of a pink solid (yield=50%).
M.p.=80° C.

Preparation 30

5-[5-Chloro-2-[[(4-methoxyphenyl)sulfonyl]amino]phenyl]-4-pentynoic acid methyl ester By following a procedure analogous to Preparation 3 starting from 4-methoxybenzenesulfonyl chloride, the expected product is obtained in the form of a yellow oil (yield=84%).
¹H NMR (DMSOd₆, 300 MHz) δ=2.58 (s, 4H), 3.65 (s, 3H), 3.80 (s, 3H), 7.05 (m, 2H), 7.29 (m, 2H), 7.36 (dd, 1H), 7.63 (m, 2H), 9.47 (s, 1H).

Preparation 31

5-[5-Chloro-2-[[(4-acetylphenyl)sulfonyl]amino]phenyl]-4-pentynoic acid methyl ester By following a procedure analogous to Preparation 3 starting from 4-acetylbenzenesulfonyl chloride, the expected product is obtained in the form of a beige solid (yield=59%).
M.p.=88° C.

Preparation 32

5-[2-[([1,1'-Biphenyl]-4-ylsulfonyl)amino]-5-chlorophenyl]-4-pentynoic acid methyl ester By following a procedure analogous to Preparation 3 starting from (1,1'-biphenyl)-4-ylsulfonyl chloride, the expected product is obtained in the form of a beige solid (yield=81%).
M.p.=93° C.

Preparation 33

5-[5-chloro-2-[[[2-(trifluoromethyl)phenyl]sulfonyl]amino]phenyl]-4-pentynoic acid methyl ester By following a procedure analogous to Preparation 3 starting from 2-(trifluoro-methyl)benzenesulfonyl chloride, the expected product is obtained in the form of an orange oil (yield=73%).
¹H NMR (DMSOd₆, 250 MHz) δ=2.56 (s, 4H), 3.63 (s, 3H), 7.27-7.42 (m, 3H), 7.83 (m, 2H), 7.96 (m, 2H), 9.95 (s, 1H).

Preparation 34

5-[5-Chloro-2-[[(3-methoxyphenyl)sulfonyl]amino]phenyl]-4-pentynoic acid methyl ester By following a procedure analogous to Preparation 3 starting from 3-methoxybenzenesulfonyl chloride, the expected product is obtained in the form of a yellow oil (yield=86%).
¹H NMR (DMSOd₆, 300 MHz) δ=2.56 (s, 4H), 3.65 (s, 3H), 3.76 (s, 3H), 7.12-7.31 (m, 4H), 7.37 (dd, 1H), 7.44 (m, 1H), 7.69 (s, 1H), 9.69 (s, 1H).

Preparation 35

5-[5-Chloro-2-[[(2,5-dimethoxyphenyl)sulfonyl]amino]phenyl]-4-pentynoic acid methyl ester By following a procedure analogous to Preparation 3 starting from 2,5-dimethoxy-benzenesulfonyl chloride, the expected product is obtained in the form of a yellow solid (yield=92%).
LC/MS: m/z=438; Tr=5.97 min.

Preparation 36

5-[5-Chloro-2-[[[4-(1,1-dimethylethyl)phenyl]sulfonyl]amino]phenyl]-4-pentynoic acid methyl ester By following a procedure analogous to Preparation 3 starting from 4-tert-butylbenzenesulfonyl chloride, the expected product is obtained in the form of a colorless oil (yield=88%).
LC/MS: m/z=434; Tr=6.89 min.

Preparation 37

5-[5-Chloro-2-[[(4-ethylphenyl)sulfonyl]amino]phenyl]-4-pentynoic acid methyl ester By following a procedure analogous to Preparation 3 starting from 4-ethylbenzenesulfonyl chloride, the expected product is obtained in the form of a yellow oil (yield=37%).
LC/MS: m/z=406; Tr=6.40 min.

Preparation 38

5-[5-Chloro-2-[[[4-(1-methylethyl)phenyl]sulfonyl]
amino]phenyl]-4-pentynoic acid methyl ester By following a procedure analogous to Preparation 3 starting from 4-isopropylbenzenesulfonyl chloride, the expected product is obtained in the form of an orange oil (yield=92%).
LC/MS: m/z=420; Tr=6.95 min.

Preparation 39

5-[5-Chloro-2-[[(4-propylphenyl)sulfonyl]amino]
phenyl]-4-pentynoic acid methyl ester By following a procedure analogous to Preparation 3 starting from 4-propylbenzenesulfonyl chloride, the expected product is obtained in the form of an orange oil (yield=22%).
LC/MS: m/z=420; Tr=6.92 min.

Preparation 40

5-[5-Chloro-2-[[(4-pentylphenyl)sulfonyl]amino]
phenyl]-4-pentynoic acid methyl ester By following a procedure analogous to Preparation 3 starting from 4-pentylbenzenesulfonyl chloride, the expected product is obtained in the form of an orange oil (yield=88%).
LC/MS: m/z=448; Tr=7.61 min.

Preparation 41

5-[5-Chloro-2-[[(3,5-dimethylphenyl)sulfonyl]
amino]phenyl]-4-pentynoic acid methyl ester By following a procedure analogous to Preparation 3 starting from 3,5-dimethyl-benzenesulfonyl chloride, the expected product is obtained in the form of an orange oil (yield=92%).
LC/MS: m/z=406; Tr=6.70 min.

Preparation 42

5-[5-chloro-2-[[(2,4,6-trimethylphenyl)sulfonyl]
amino]phenyl]-4-pentynoic acid methyl ester By following a procedure analogous to Preparation 3 starting from 2,4,6-trimethylbenzene-sulfonyl chloride, the expected product is obtained in the form of an orange oil (yield=23%).
LC/MS: m/z=420; Tr=6.66 min.

Preparation 43

5-[5-Chloro-2-[[(4-chlorophenyl)sulfonyl]amino]
phenyl]-4-pentynoic acid methyl ester By following a procedure analogous to Preparation 3 starting from 4-chlorobenzenesulfonyl chloride, the expected product is obtained in the form of an orange oil (yield=56%).
LC/MS: m/z=412; Tr=6.27 min.

Preparation 44

5-[5-Chloro-2-[[(4-fluorophenyl)sulfonyl]amino]
phenyl]-4-pentynoic acid methyl ester By following a procedure analogous to Preparation 3 starting from 4-fluorobenzenesulfonyl chloride, the expected product is obtained in the form of an orange oil (yield=28%).
LC/MS: m/z=396; Tr=5.99 min.

Preparation 45

5-[5-Chloro-2-[[(4-chloro-3-methylphenyl)sulfonyl]
amino]phenyl]-4-pentynoic acid methyl ester By following a procedure analogous to Preparation 3 starting from 4-chloro-3-methylbenzenesulfonyl chloride, the expected product is obtained in the form of a yellow oil (yield=59%).
LC/MS: m/z=426; Tr=6.80 min.

Preparation 46

5-[5-Chloro-2-[[[3-(trifluoromethyl)phenyl]sulfonyl]
amino]phenyl]-4-pentynoic acid methyl ester By following a procedure analogous to Preparation 3 starting from 3-(trifluoromethyl)benzenesulfonyl chloride, the expected product is obtained in the form of an orange oil (yield=50%).
LC/MS: m/z=446; Tr=6.58 min.

Preparation 47

5-[2-[[[4-(Acetylamino)phenyl]sulfonyl]amino]-5-
chlorophenyl]-4-pentynoic acid methyl ester By following a procedure analogous to Preparation 3 starting from 4-(acetylamino)-benzenesulfonyl chloride, the expected product is obtained in the form of an orange solid (yield=74%).
LC/MS: m/z=435; Tr=5.15 min.

Preparation 48

5-[5-Chloro-2-[[(4-cyanophenyl)sulfonyl]amino]
phenyl]-4-pentynoic acid methyl ester By following a procedure analogous to Preparation 3 starting from 4-cyanobenzenesulfonyl chloride, the expected product is obtained in the form of a yellow solid (yield=87%).
LC/MS: m/z=403; Tr=5.71 min.

Preparation 49

5-[5-Chloro-2-[[(4-phenoxyphenyl)sulfonyl]amino]
phenyl]-4-pentynoic acid methyl ester By following a procedure analogous to Preparation 3 starting from 4-phenoxybenzenesulfonyl chloride, the expected product is obtained in the form of a yellow solid (yield=71%).
LC/MS: m/z=470; Tr=6.67 min.

Preparation 50

5-[5-Chloro-2-[(1-naphthalenylsulfonyl)amino]phenyl]-4-pentynoic acid methyl ester By following a procedure analogous to Preparation 3 starting from 1-naphthalenesulfonyl chloride, the expected product is obtained in the form of a brown oil (yield=89%).

$^1$H NMR (DMSOd$_6$, 300 MHz) δ=2.15 (t, 2H), 2.44 (t, 2H), 3.63 (s, 3H), 7.18 (s, 1H), 7.34 (s, 2H), 7.62 (m, 3H), 8.01 (dd, 1H), 8.04 (d, 1H), 8.22 (d, 1H), 8.72 (d, 1H), 10.01 (s, 1H).

Preparation 51

5-[5-Chloro-2-[(2-naphthalenylsulfonyl)amino]phenyl]-4-pentynoic acid methyl ester By following a procedure analogous to Preparation 3 starting from 2-naphthalenesulfonyl chloride, the expected product is obtained in the form of a colorless oil (yield=22%).

LC/MS: m/z=428; Tr=6.63 min.

Preparation 52

5-[5-Chloro-2-[[(4-methyl-1-naphthalenyl)sulfonyl]amino]phenyl]-4-pentynoic acid methyl ester By following a procedure analogous to Preparation 3 starting from 4-methyl-1-naphthalenesulfonyl chloride, the expected product is obtained in the form of a yellow oil (yield=77%).

$^1$H NMR (DMSOd$_6$, 250 MHz) δ=2.24 (t, 2H), 2.37 (t, 2H), 2.70 (s, 3H), 3.64 (s, 3H), 7.25 (s, 1H), 7.33 (s, 2H), 7.45 (dd, 1H), 7.68 (m, 2H), 7.93 (d, 1H), 8.15 (m, 1H), 8.75 (m, 1H), 9.91 (s, 1H).

Preparation 53

5-[2-[[[5-(Acetylamino)-1-naphthalenyl]sulfonyl]amino]-5-chlorophenyl]-4-pentynoic acid methyl ester By following a procedure analogous to Preparation 3 starting from 5-(acetylamino)-1-naphthalenesulfonyl chloride, the expected product is obtained in the form of a colorless oil (yield=94%).

$^1$H NMR (DMSOd$_6$, 300 MHz) δ=2.18 (s, 3H), 2.23 (t, 2H), 2.41 (t, 2H), 3.62 (s, 3H), 7.18 (s, 1H), 7.32 (s, 2H), 7.62 (m, 2H), 7.76 (d, 1H), 8.04 (dd, 1H), 8.35 (d, 1H), 8.58 (d, 1H), 10.03 (s, 1H).

Preparation 54

5-[5-Chloro-2-[(8-quinolinylsulfonyl)amino]phenyl]-4-pentynoic acid methyl ester By following a procedure analogous to Preparation 3 starting from 8-quinolinesulfonyl chloride, the expected product is obtained in the form of a yellow oil (yield=76%).

LC/MS: m/z=429; Tr=5.96 min.

Preparation 55

6-[5-Chloro-2-[(phenylsulfonylamino)phenyl]-5-hexynoic acid methyl ester

By following a procedure analogous to Preparation 3 starting from the compound obtained according to Preparation 13, the expected product is obtained in the form of an orange solid (yield=66%).

M.p.=90° C.

Preparation 56

6-[5-Chloro-2-[[(2,3-dichlorophenyl)sulfonyl]amino]phenyl]-5-hexynoic acid methyl ester By following a procedure analogous to Preparation 55 starting from 2,3-dichloro-benzenesulfonyl chloride, the expected product is obtained in the form of a yellow oil (yield=87%).

$^1$H NMR (DMSOd$_6$, 250 MHz) δ=1.72 (m, 2H), 2.35 (t, 2H), 2.43 (t, 2H), 3.60 (s, 3H), 7.25-7.36 (m, 2H), 7.39 (s, 1H), 7.48 (t, 1H), 7.79 (d, 1H), 7.90 (d, 1H), 10.28 (s, 1H).

Preparation 57

6-[5-Chloro-2-[[(4-methoxyphenyl)sulfonyl]amino]phenyl]-5-hexynoic acid methyl ester By following a procedure analogous to Preparation 55 starting from 4-methoxybenzenesulfonyl chloride, the expected product is obtained in the form of a yellow oil (yield=43%).

$^1$H NMR (DMSOd$_6$, 250 MHz) δ=1.73 (m, 2H), 2.35-2.48 (m, 4H), 3.62 (s, 3H), 3.81 (s, 3H), 7.04 (d, 2H), 7.25-7.35 (m, 3H), 7.60 (d, 2H), 9.57 (s, 1H).

Preparation 58

6-[5-Chloro-2-[(8-quinolinylsulfonyl)amino]phenyl]-5-hexynoic acid methyl ester By following a procedure analogous to Preparation 55 starting from 8-quinolinesulfonyl chloride, the expected product is obtained in the form of a white powder (yield=48%).

$^1$H NMR (DMSOd$_6$, 300 MHz) δ=1.77 (m, 2H), 2.44 (m, 4H), 3.61 (s, 3H), 7.29 (s, 2H), 7.43 (d, 1H), 7.75 (m, 2H), 8.32 (d, 1H), 8.39 (d, 1H), 8.55 (d, 1H), 9.01 (s, 1H), 9.08 (d, 1H).

Preparation 59

6-[5-Chloro-2-[[[4-(1-methylethyl)phenyl]sulfonyl]amino]phenyl]-5-hexynoic acid methyl ester By following a procedure analogous to Preparation 55 starting from 4-isopropylbenzene-sulfonyl chloride, the expected product is obtained in the form of an orange oil (yield=86%).

$^1$H NMR (DMSOd$_6$, 300 MHz) δ=1.20 (d, 6H), 1.71 (m, 2H), 2.34 (t, 2H), 2.41 (t, 2H), 2.73 (m, 1H), 3.61 (s, 3H), 7.26-7.62 (m, 5H), 9.71 (s, 1H).

Preparation 60

6-[5-Chloro-2-[(2-naphthalenylsulfonyl)amino]phenyl]-5-hexynoic acid methyl ester By following a procedure analogous to Preparation 55 starting from 2-naphthalenesulfonyl chloride, the expected product is obtained in the form of a yellow oil (yield=69%).
$^1$H NMR (DMSOd$_6$, 300 MHz) δ=1.59 (m, 2H), 2.20 (t, J=7.1 Hz, 2H), 2.32 (t, J=7.4 Hz, 2H), 3.61 (s, 3H), 7.08-7.34 (m, 3H), 7.63-7.74 (m, 3H), 7.99-8.33 (m, 3H), 9.91 (s, 1H).

Preparation 61

6-[5-Chloro-2-[[(3,5-dimethylphenyl)sulfonyl]amino]phenyl]-5-hexynoic acid methyl ester By following a procedure analogous to Preparation 55 starting from 3,5-dimethylbenzene-sulfonyl chloride, the expected product is obtained in the form of a white powder (yield=71%).
M.p.=92-94° C.

Preparation 62

6-[5-Chloro-2-[[(3-methoxyphenyl)sulfonyl]amino]phenyl]-5-hexynoic acid methyl ester By following a procedure analogous to Preparation 55 starting from 3-methoxybenzenesulfonyl chloride, the expected product is obtained in the form of a yellow powder (yield=82%).
M.p.=71-76° C.

Preparation 63

6-[5-Chloro-2-[[(2,5-dimethoxyphenyl)sulfonyl]amino]phenyl]-5-hexynoic acid methyl ester By following a procedure analogous to Preparation 55 starting from 2,5-dimethoxybenzene-sulfonyl chloride, the expected product is obtained in the form of a white powder (yield=80%).
M.p.=115-117° C.

Preparation 64

6-[5-Chloro-2-[(1-naphthalenylsulfonyl)amino]phenyl]-5-hexynoic acid methyl ester By following a procedure analogous to Preparation 55 starting from 1-naphthalenesulfonyl chloride, the expected product is obtained in the form of a yellow powder (yield=81%).
M.p.=93-95° C.

Preparation 65

5-Fluoro-1H-indole-2-propanoic acid methyl ester

By following a procedure analogous to Preparation 6 starting from the compound obtained according to Preparation 15, the expected product is obtained in the form of a beige solid (yield=71%).

$^1$H NMR (DMSOd$_6$, 300 MHz) δ=2.75 (t, 2H), 2.98 (t, 2H), 3.61 (s, 3H), 6.14 (dd, 1H), 6.82 (ddd, 1H), 7.15 (dd, 1H), 7.25 (dd, 4.68 Hz, 1H), 11.02 (s, 1H).

Preparation 66

5,6-Dichloro-1H-indole-2-propanoic acid methyl ester

By following a procedure analogous to Preparation 6 starting from the compound obtained according to Preparation 16, the expected product is obtained in the form of a brown solid (yield=100%).
M.p.=142° C.

Preparation 67

4,5-Dichloro-1H-indole-2-propanoic acid methyl ester

By following a procedure analogous to Preparation 6 starting from the compound obtained according to Preparation 17, the expected product is obtained in the form of a brown solid (yield=90%).
$^1$H NMR (DMSOd$_6$, 300 MHz) δ=2.78 (t, 2H), 3.01 (t, 2H), 3.61 (s, 3H), 6.24 (s, 1H), 7.17 (d, 1H), 7.29 (d, 1H) 11.49 (s, 1H).

Preparation 68

6-(Trifluoromethyl)-1H-indole-2-propanoic acid methyl ester

By following a procedure analogous to Preparation 6 starting from the compound obtained according to Preparation 18, the expected product is obtained in the form of a beige solid (yield=91%).
M.p.=108-110° C.

Preparation 69

5-Acetyl-1H-indole-2-propanoic acid methyl ester

By following a procedure analogous to Preparation 6 starting from the compound obtained according to Preparation 19, the expected product is obtained in the form of a beige solid (yield=91%).
$^1$H NMR (DMSOd$_6$, 250 MHz) δ=2.57 (s, 3H), 2.77 (t, 2H), 3.01 (t, 2H), 3.61 (s, 3H), 6.32 (s, 1H), 7.34 (d, 1H), 7.66 (dd, 1H), 8.15 (d, 1H), 11.33 (s, 1H).

Preparation 70

6-Chloro-5-fluoro-1H-indole-2-propanoic acid methyl ester

By following a procedure analogous to Preparation 6 starting from the compound obtained according to Preparation 20, the expected product is obtained in the form of a gray solid (yield=92%).
M.p.=138-139° C.

Preparation 71

5,7-Dichloro-1H-indole-2-propanoic acid methyl ester

By following a procedure analogous to Preparation 6 starting from the compound obtained according to Preparation 23, the expected product is obtained in the form of a brown solid (yield=30%).

$^1$H NMR (DMSOd$_6$, 250 MHz) δ=2.77 (t, 2H), 3.02 (t, 2H), 3.61 (s, 3H), 6.26 (s, 1H), 7.15 (d, 1H), 7.47 (d, 1H), 11.47 (s, 1H).

Preparation 72

5-Cyano-1H-indole-2-propanoic acid methyl ester

By following a procedure analogous to Preparation 6 starting from the compound obtained according to Preparation 21, the expected product is obtained in the form of a beige solid (yield=72%).

$^1$H NMR (DMSOd$_6$, 250 MHz) δ=2.77 (t, 2H), 3.02 (t, 2H), 3.60 (s, 3H), 6.33 (s, 1H), 7.35 (dd, 1H), 7.35 (dd, 1.6 Hz, 1H), 7.4 (d, 1H), 7.93 (d, 1H), 11.56 (s, 1H).

Preparation 73

5-Benzoyl-1H-indole-2-propanoic acid methyl ester

By following a procedure analogous to Preparation 6 starting from the compound obtained according to Preparation 22, the expected product is obtained in the form of a brown solid (yield=44%).

$^1$H NMR (DMSOd$_6$, 250 MHz) δ=2.77 (t, 2H), 3.02 (t, 2H), 3.61 (s, 3H), 6.33 (s, 1H), 7.42 (d, 1H), 7.45-7.75 (m, 7H), 7.86 (d, 1H), 11.42 (s, 1H).

Preparation 74

7-[5-Chloro-2-[(phenylsulfonyl)amino]phenyl]-6-heptynoic acid methyl ester

By following a procedure analogous to Preparation 3 starting from the compound obtained according to Preparation 14, the expected product is obtained in the form of a colorless oil (yield=54%).

$^1$H NMR (DMSOd$_6$, 250 MHz) δ=1.55 (m, 4H), 2.33 (m, 4H), 3.60 (s, 3H), 7.22 (m, 3H), 7.61 (m, 5H), 9.75 (s, 1H).

Preparation 75

6-[5-Chloro-2-[[(3,4-dihydro-4-methyl-2H-1,4-benzoxazin-7-yl)sulfonyl]amino]phenyl]-5-hexynoic acid methyl ester By following a procedure analogous to Preparation 55 starting from 3,4-dihydro-4-methyl-2H-1,4-benzoxazine-7-sulfonyl chloride, the expected product is obtained in the form of a white powder (yield=88%).

M.p.=131-133° C.

Preparation 76

6-[5-Chloro-2-[[[1,2,3,4-tetrahydro-2-(trifluoroacetyl)-7-isoquinolinyl]sulfonyl]-amino]phenyl]-5-hexynoic acid methyl ester By following a procedure analogous to Preparation 55 starting from 1,2,3,4-tetrahydro-2-(trifluoroacetyl)-7-isoquinolinesulfonyl chloride, the expected product is obtained in the form of a yellow oil (yield=89%).

$^1$H NMR (DMSOd$_6$, 300 MHz) δ=1.70-1.75 (m, 2H), 2.35-2.45 (m, 4H), 3.0 (t, 2H), 3.85 (t, 2H), 4.80 (s, 2H), 7.30-7.35 (m, 4H), 7.60 (dd, 1H), 7.65 (d, 1H), 9.80 (s, 1H).

Preparation 77

6-[5-Chloro-2-[[(2,3-dihydro-1,4-benzodioxin-6-yl)sulfonyl]amino]phenyl]-5-hexynoic acid methyl ester By following a procedure analogous to Preparation 55 starting from 2,3-dihydro-1,4-benzodioxine-6-sulfonyl chloride, the expected product is obtained in the form of a yellow oil (yield=95%).

$^1$H NMR (DMSOd$_6$, 250 MHz) δ=1.70-1.81 (m, 2H), 2.37-2.51 (m, 4H), 3.61 (s, 3H), 4.25-4.32 (m, 4H), 6.59-7.37 (m, 6H), 9.63 (s, 1H).

Preparation 78

6-[5-Chloro-2-[[(6-benzothiazolyl)sulfonyl]amino]phenyl]-5-hexynoic acid methyl ester By following a procedure analogous to Preparation 55 starting from 6-benzothiazolesulfonyl chloride, the expected product is obtained in the form of a yellow oil (yield=63%).

$^1$H NMR (DMSOd$_6$, 300 MHz) δ=1.56-1.66 (m, 2H), 2.23 (t, 2H), 2.35 (t, 2H), 3.60 (s, 3H), 7.27-7.39 (m, 3H), 7.79 (d, 1H), 8.21 (d, 1H), 8.60 (s, 1H), 9.61 (s, 1H), 9.97 (s, 1H).

Preparation 79

6-[5-Chloro-2-[[[6-(4-morpholinyl)-3-pyridinyl]sulfonyl]amino]phenyl]-5-hexynoic acid methyl ester By following a procedure analogous to Preparation 55 starting from 6-(4-morpholinyl)-3-pyridinesulfonyl chloride, the expected product is obtained in the form of a yellow oil (yield=66%).

$^1$H NMR (DMSOd$_6$, 300 MHz) δ=1.69-1.79 (m, 2H), 2.36-2.51 (m, 4H), 3.55-3.58 (m, 4H), 3.60 (s, 3H), 3.64-3.68 (m, 4H), 6.87 (d, 1H), 7.29-7.39 (m, 3H), 7.64 (dd, 1H), 8.30 (d, 1H), 9.58 (s, 1H).

Preparation 80

6-[5-Chloro-2-[[(3,5-dimethyl-4-isoxazolyl)sulfonyl]amino]phenyl]-5-hexynoic acid methyl ester By following a procedure analogous to Preparation 55 starting from 3,5-dimethyl-4-isoxazolesulfonyl chloride, the expected product is obtained in the form of a yellow powder (yield=62%).

M.p.=107-109° C.

Preparation 81

6-[5-Chloro-2-[[(1,3,5-trimethyl-1H-pyrazol-4-yl)sulfonyl]amino]phenyl]-5-hexynoic acid methyl ester By following a procedure analogous to Preparation 55 starting from 1,3,5-trimethyl-1H-pyrazole-4-sulfonyl chloride, the expected product is obtained in the form of a yellow oil (yield=86%).

$^1$H NMR (DMSOd$_6$, 250 MHz) δ=1.73-1.81 (m, 2H), 2.05 (s, 3H), 2.15 (s, 3H), 2.36 (d, 2H), 2.42 (d, 2H), 3.61 (s, 3H), 3.62 (s, 3H), 7.31-7.41 (m, 3H), 9.38 (s, 1H).

Preparation 82

6-[5-Chloro-2-[[(1-methyl-1H-imidazol-4-yl)sulfonyl]amino]phenyl]-5-hexynoic acid methyl ester By following a procedure analogous to Preparation 55 starting from 1-methyl-1H-imidazole-4-sulfonyl chloride, the expected product is obtained in the form of a yellow powder (yield=89%).

M.p.=76-79° C.

Preparation 83

6-[2-[[(2,1,3-Benzothiadiazol-4-yl)sulfonyl]amino]-5-chlorophenyl]-5-hexynoic acid methyl ester By following a procedure analogous to Preparation 55 starting from 2,1,3-benzothiadiazole-4-sulfonyl chloride, the expected product is obtained in the form of a yellow oil (yield=87%).

$^1$H NMR (DMSOd$_6$, 300 MHz) δ=1.49-1.59 (m, 2H), 2.03 (t, 2H), 2.32 (t, 2H), 3.60 (s, 3H), 7.25-7.38 (m, 3H), 7.82 (dd, 1H), 8.13 (dd, 1H), 8.37 (dd, 1H), 9.83 (s, 1H).

Preparation 84

6-[2-[[(2,1,3-Benzothiadiazol-5-yl)sulfonyl]amino]-5-chlorophenyl]-5-hexynoic acid methyl ester By following a procedure analogous to Preparation 55 starting from 2,1,3-benzothiadiazole-5-sulfonyl chloride, the expected product is obtained in the form of a yellow oil (yield=22%).

$^1$H NMR (DMSOd$_6$, 300 MHz) δ=1.52-1.62 (m, 2H), 2.20 (t, 2H), 2.33 (t, 2H), 3.59 (s, 3H), 7.31-7.40 (m, 3H), 7.95 (dd, 1H), 8.31 (dd, 1H), 8.36 (dd, 1H), 10.3 (s, 1H).

Preparation 85

6-[5-Chloro-2-[[(3,4-dihydro-2,2-dimethyl-2H-1-benzopyran-6-yl)sulfonyl]amino]phenyl]-5-hexynoic acid methyl ester By following a procedure analogous to Preparation 55 starting from 3,4-dihydro-2,2-dimethyl-2H-1-benzopyran-6-sulfonyl chloride, the expected product is obtained in the form of a yellow oil (yield=88%).

$^1$H NMR (DMSOd$_6$, 300 MHz) δ=1.28 (s, 6H), 1.70-1.79 (m, 4H), 2.35-2.51 (m, 4H), 2.72 (t, 2H), 3.60 (s, 3H), 6.80 (d, 1H), 7.25-7.65 (m, 5H), 9.48 (s, 1H).

Preparation 86

6-[5-Chloro-2-[[(5,6,7,8-tetrahydro-5,5,8,8-tetramethyl-2-naphthalenyl)-sulfonyl]amino]phenyl]-5-hexynoic acid methyl ester By following a procedure analogous to Preparation 55 starting from 5,6,7,8-tetrahydro-5,5,8,8-tetramethyl-2-naphthalenesulfonyl chloride, the expected product is obtained in the form of a yellow powder (yield=65%).

M.p.=113-115° C.

Preparation 87

6-[2-[[(1-Acetyl-2,3-dihydro-1H-indol-5-yl)sulfonyl]amino]-5-chlorophenyl]-5-hexynoic acid methyl ester By following a procedure analogous to Preparation 55 starting from 1-acetyl-2,3-dihydro-1H-indole-5-sulfonyl chloride, the expected product is obtained in the form of a pasty solid (yield=88%).

$^1$H NMR (DMSOd$_6$, 250 MHz) δ=1.68-1.80 (m, 2H), 2.17 (s, 3H), 2.39 (t, 2H), 2.43 (t, 2H), 3.14 (t, 2H), 3.61 (s, 3H), 4.14 (t, 2H), 7.25 (dd, 1H), 7.32-7.37 (m, 2H), 7.48 (d, 1H), 7.52 (d, 1H), 8.07 (d, 1H), 9.59 (s, 1H).

Preparation 88

6-[5-Chloro-2-[[(2-methyl-6-benzothiazolyl)sulfonyl]amino]phenyl]-5-hexynoic acid methyl ester By following a procedure analogous to Preparation 55 starting from 2-methyl-6-benzothiazolesulfonyl chloride, the expected product is obtained in the form of a yellow solid (yield=68%).

M.p.=103-106° C.

Preparation 89

6-[2-[[[2-(Acetylamino)-6-benzothiazolyl]sulfonyl]amino]-5-chlorophenyl]-5-hexynoic acid methyl ester By following a procedure analogous to Preparation 55 starting from 2-(acetylamino)-6-benzothiazolesulfonyl chloride, the expected product is obtained in the form of a white powder (yield=80%).

M.p.=138-140° C.

Preparation 90

6-[2-[[(2-Amino-6-benzothiazolyl)sulfonyl]amino]-5-chlorophenyl]-5-hexynoic acid methyl ester By following a procedure analogous to Preparation 55 starting from 2-amino-6-benzothiazolesulfonyl chloride, the expected product is obtained in the form of an orange solid (yield=96%).

M.p.=61-65° C.

Preparation 91

6-[5-Chloro-2-[[(2-methyl-6-benzoxazolyl)sulfonyl]amino]phenyl]-5-hexynoic acid methyl ester By following a procedure analogous to Preparation 55 starting from 2-methyl-6-benzoxazolesulfonyl chloride, the expected product is obtained in the form of an orange oil (yield=93%).

$^1$H NMR (DMSOd$_6$, 250 MHz) δ=1.65 (m, 2H), 2.15 (t, 2H), 2.39 (t, 2H), 2.65 (s, 3H), 3.61 (s, 3H), 7.26-7.39 (m, 3H), 7.65 (dd, 1H), 7.81 (d, 1H), 7.95 (s, 1H), 9.93 (s, 1H).

Preparation 92

6-[5-Chloro-2-[[(2,3-dihydro-5-benzofuranyl)sulfonyl]amino]phenyl]-5-hexynoic acid methyl ester By following a procedure analogous to Preparation 55 starting from 2,3-dihydro-5-benzofuransulfonyl chloride, the expected product is obtained in the form of an orange oil (yield=99%).

$^1$H NMR (DMSOd$_6$, 300 MHz) δ=1.76 (m, 2H), 2.40-2.49 (m, 4H), 3.23 (t, 2H), 3.85 (s, 3H), 4.62 (t, 2H), 6.85 (d, 1H), 7.25-7.45 (m, 4H), 7.77 (s, 1H), 9.51 (s, 1H).

Preparation 93

6-[5-Chloro-2-[[(2-methyl-5-benzothiazolyl)sulfonyl]amino]phenyl]-5-hexynoic acid methyl ester By following a procedure analogous to Preparation 55 starting from 2-methyl-5-benzothiazolesulfonyl chloride, the expected product is obtained in the form of a yellow solid (yield=42%).

M.p.=68-72° C.

Preparation 94

6-[2-[[(2-Amino-6-benzoxazolyl)sulfonyl]amino]-5-chlorophenyl]-5-hexynoic acid methyl ester By following a procedure analogous to Preparation 55 starting from 2-amino-6-benzoxazolesulfonyl chloride, the expected product is obtained is the form of a white solid (yield=9%).

M.p.=135° C.

Preparation 95

6-[2-[[[2-(Acetylamino)-4-methyl-5-thiazolyl]sulfonyl]amino]-5-chlorophenyl]-5-hexynoic acid methyl ester By following a procedure analogous to Preparation 55 starting from 2-(acetylamino)-4-methyl-5-thiazolesulfonyl chloride, the expected product is obtained in the form of a white powder (yield=62%).

M.p.=147-149° C.

Preparation 96

6-[5-Chloro-2-[[(1,2,3,4-tetrahydro-2-oxo-6-quinolinyl)sulfonyl]amino]phenyl]-5-hexynoic acid methyl ester By following a procedure analogous to Preparation 55 starting from 1,2,3,4-tetrahydro-2-oxo-6-quinolinesulfonyl chloride, the expected product is obtained in the form of a yellow powder (yield=27%).

M.p.=53-57° C.

Preparation 97

5-[2-[[(6-Benzothiazolyl)sulfonyl]amino]-5-chlorophenyl]-4-pentynoic acid methyl ester By following a procedure analogous to Preparation 3 starting from 6-benzothiazolesulfonyl chloride, the expected product is obtained in the form of a yellow oil (yield=92%).

$^1$H NMR (DMSOd$_6$, 300 MHz) δ=2.44 (s, 4H), 3.63 (s, 3H), 7.26-7.39 (m, 3H), 7.25-7.65 (m, 5H), 7.80 (dd, 1H), 8.21 (dd, 1H), 8.62 (d, 1H), 9.62 (s, 1H), 9.88 (s, 1H).

Preparation 98

5-[2-[[[2-(Acetylamino)-6-benzothiazolyl]sulfonyl]amino]-5-chlorophenyl]-4-pentynoic acid methyl ester By following a procedure analogous to Preparation 3 starting from 2-(acetylamino)-6-benzothiazolesulfonyl chloride, the expected product is obtained in the form of a beige solid (yield=99%).

M.p.=85° C.

Preparation 99

5-[2-[[(1-Acetyl-2,3-dihydro-1H-indol-5-yl)sulfonyl]amino]-5-chlorophenyl]-4-pentynoic acid methyl ester By following a procedure analogous to Preparation 3 starting from 1-acetyl-2,3-dihydro-1H-indole-5-sulfonyl chloride, the expected product is obtained in the form of a beige solid (yield=84%).

M.p.=154° C.

Preparation 100

5-[2-[[(1,3-Benzodioxol-5-yl)sulfonyl]amino]-5-chlorophenyl]-4-pentynoic acid methyl ester By following a procedure analogous to Preparation 3 starting from 1,3-benzodioxole-5-sulfonyl chloride, the expected product is obtained in the form of a brown oil (yield=98%).

$^1$H NMR (DMSOd$_6$, 300 MHz) δ=2.60 (s, 4H), 3.65 (s, 3H), 6.15 (s, 2H), 7.01 (d, J=8.73 Hz, 1H), 7.20 (dd, 2H), 7.27 (s, H), 7.30-7.38 (m, 2H).

Preparation 101

6-[2-[[(1,3-Benzodioxol-5-yl)sulfonyl]amino]-5-chlorophenyl]-5-hexynoic acid methyl ester By following a procedure analogous to Preparation 55 starting from 1,3-benzodioxole-5-sulfonyl chloride, the expected product is obtained in the form of a brown oil (yield=89%).

¹H NMR (DMSOd₆, 300 MHz) δ=1.76 (m, 2H), 2.37-2.45 (m, 4H), 3.61 (s, 3H), 6.14 (s, 2H), 7.0 (d, 1H), 7.38-7.71 (m, 5H), 9.68 (s, 1H).

Preparation 102

6-[5-Chloro-2-[[[4-(4-morpholinylsulfonyl)phenyl]sulfonyl]amino]phenyl]-5-hexynoic acid methyl ester By following a procedure analogous to Preparation 55 starting from 4-(4-morpholinylsulfonyl)benzenesulfonyl chloride, the expected product is obtained in the form of a white solid (yield=66%).
M.p.=135-139° C.

Preparation 103

6-[2-Amino-5-(trifluoromethyl)phenyl]-5-hexynoic acid methyl ester

By following a procedure analogous to Preparation 5 starting from the methyl ester of 5-hexynoic acid, the expected product is obtained in the form of a brown oil (yield=84%).
¹H NMR (DMSOd₆, 250 MHz) δ=1.86 (q, 2H), 2.45-2.54 (m, 4H), 3.6 (s, 3H), 5.96 (s, NH₂), 6.78 (d, 1H), 7.30 (dd, 1H), 7.36 (d, 1H).

Preparation 104

5-[2-[[(6-Benzothiazolyl)sulfonyl]amino]-5-(trifluoromethyl)phenyl]-4-pentynoic acid methyl ester By following a procedure analogous to Preparation 97 starting from the methyl ester of 5-[2-amino-5-(trifluoromethyl)phenyl]-4-pentynoic acid (Preparation 5), the expected product is obtained in the form of an orange oil (yield=83%).
¹H NMR (DMSOd₆, 500 MHz) δ=2.53 (d, 2H), 2.55 (d, 2H), 3.65 (s, 3H), 6.80 (d, 1H), 7.54-7.66 (m, 3H), 7.90 (dd, J1H), 8.22 (d, 1H), 8.73 (d, 1H), 9.63 (s, 1H), 10.13 (s, 1H).

Preparation 105

6-[2-[[(2-Methyl-6-benzoxazolyl)sulfonyl]amino]-5-(trifluoromethyl)phenyl]-5-hexynoic acid methyl ester By following a procedure analogous to Preparation 91 starting from the methyl ester of 6-[2-amino-5-(trifluoromethyl)phenyl]-5-hexynoic acid (preparation 103) and 2-methyl-6-benzoxazolesulfonyl chloride, the expected product is obtained in the form of an orange oil (yield=54%).
¹H NMR (DMSOd₆, 300 MHz) δ=1.65-1.75 (m, 2H), 2.33-2.43 (m, 4H), 2.65 (s, 3H), 3.60 (s, 3H), 7.49 (d, 1H), 7.62 (s, 1H), 7.63 (d, 1H), 7.74 (dd, 1H), 7.82 (d, 1H), 8.07 (s, 1H), 10.16 (s, 1H).

Preparation 106

6-[2-[[(1-Acetyl-2,3-dihydro-1H-indol-5-yl)sulfonyl]amino]-5-(trifluoromethyl)phenyl]-5-hexynoic acid methyl ester By following a procedure analogous to Preparation 105 starting from 1-acetyl-2,3-dihydro-1H-indole-5-sulfonyl chloride, the expected product is obtained in the form of a pasty solid (yield=56%).

¹H NMR (DMSOd₆, 300 MHz) δ=1.74-1.83 (m, 2H), 2.16 (s, 3H), 2.43-2.48 (m, 4H), 3.15 (t, 2H), 3.61 (s, 3H), 4.13 (t, 2H), 7.44-7.47 (m, 1H), 7.58-7.61 (m, 4H), 8.07-8.10 (m, 1H), 9.86 (s, 1H).

Preparation 107

6-[2-[[(2,3-Dihydro-5-benzofuranyl)sulfonyl]amino]-5-(trifluoromethyl)phenyl]-5-hexynoic acid methyl ester By following a procedure analogous to Preparation 105 starting from 2,3-dihydro-5-benzofuransulfonyl chloride, the expected product is obtained in the form of a yellow paste (yield=19%).
¹H NMR (DMSOd₆, 250 MHz) δ=1.80 (t, 2H), 2.43-2.51 (m, 4H), 3.21 (t, 2H), 3.61 (s, 3H), 4.62 (t, 2H), 6.87 (d, 1H), 7.48 (d, 1H), 7.55 (dd, 1H), 7.60-7.67 (m, 3H), 9.77 (s, 1H).

Preparation 108

6-[2-[[(2-Methyl-5-benzothiazolyl)sulfonyl]amino]-5-(trifluoromethyl)phenyl]-5-hexynoic acid methyl ester By following a procedure analogous to Preparation 105 starting from 2-methyl-5-benzothiazolesulfonyl chloride, the expected product is obtained in the form of a yellow paste (yield=17%).
¹H NMR (DMSOd₆, 250 MHz) δ=1.61-1.73 (m, 2H), 2.32 (t, 2H), 2.38 (t, 2H), 2.83 (s, 3H), 3.60 (s, 3H), 7.52 (d, 1H), 7.60-7.66 (m, 3H), 7.72 (dd, 1H), 8.23 (d, 1H), 8.25 (s, 1H), 10.19 (s, 1H).

Preparation 109

5-[2-[[(2-Amino-6-benzothiazolyl)sulfonyl]amino]-5-(trifluoromethyl)phenyl]-4-pentynoic acid methyl ester By following a procedure analogous to Preparation 104 starting from 2-amino-6-benzothiazolesulfonyl chloride, the expected product is obtained in the form of a yellow oil (yield=69%).
¹H NMR (DMSOd₆, 250 MHz) δ=2.65 (m, 4H), 3.68 (s, 3H), 7.40 (d, 1H), 7.54-7.66 (m, 4H), 7.99 (s, 2H), 8.19 (d, 1H), 9.71 (s, 1H).

Preparation 110

5-[2-[[(2-Methyl-6-benzothiazolyl)sulfonyl]amino]-5-(trifluoromethyl)phenyl]-4-pentynoic acid methyl ester By following a procedure analogous to Preparation 104 starting from 2-methyl-6-benzothiazolesulfonyl chloride, the expected product is obtained in the form of a yellow oil (yield=24%).
¹H NMR (DMSOd₆, 300 MHz) δ=2.54 (m, 4H), 2.84 (s, 3H), 3.65 (s, 3H), 7.53 (m, 2H), 7.56 (m, 1H), 7.65 (dd, 1H), 7.83 (dd, 1H), 8.05 (dd, 1H), 8.57 (d, 1H), 10.05 (s, 1H).

Preparation 111

5-[2-[[(2-Methyl-5-benzothiazolyl)sulfonyl]amino]-5-(trifluoromethyl)phenyl]-4-pentynoic acid methyl ester By following a procedure analogous to Preparation 104 starting from 2-methyl-5-benzothiazolesulfonyl chloride, the expected product is obtained in the form of a yellow oil (yield=46%).
$^1$H NMR (DMSOd$_6$, 250 MHz) δ=2.55 (m, 4H), 2.83 (s, 3H), 3.65 (s, 3H), 7.55 (m, 2H), 7.66 (dd, 1H), 7.72 (dd, 1H), 8.24 (d, 1H), 8.30 (d, 1H), 10.09 (s, 1H).

Preparation 112

5-[2-[[(2-Methyl-6-benzoxazolyl)sulfonyl]amino]-5-(trifluoromethyl)phenyl]-4-pentynoic acid methyl ester By following a procedure analogous to Preparation 104 starting from 2-methyl-6-benzoxazolesulfonyl chloride, the expected product is obtained in the form of a white powder (yield=41%).
$^1$H NMR (DMSOd$_6$, 250 MHz) δ=2.56 (m, 4H), 2.66 (s, 3H), 3.65 (s, 3H), 7.55 (m, 2H), 7.62 (d, 1H), 7.75 (dd, 1H), 7.83 (dd, 1H), 8.12 (dd, 1H), 10.04 (s, 1H).

Preparation 113

5-[2-[[(2-Methyl-7-benzothiazolyl)sulfonyl]amino]-5-(trifluoromethyl)phenyl]-4-pentynoic acid methyl ester By following a procedure analogous to Preparation 104 starting from 2-methyl-7-benzothiazolesulfonyl chloride, the expected product is obtained in the form of an orange oil (yield=32%).
$^1$H NMR (DMSOd$_6$, 250 MHz) δ=2.40 (m, 4H), 2.78 (s, 3H), 3.64 (s, 3H), 7.68 (m, 3H), 8.17 (dd, 1H), 10.40 (s, 1H).

Preparation 114

5-[2-[[(1-Acetyl-2,3-dihydro-1H-indol-5-yl)sulfonyl]amino]-5-(trifluoromethyl)phenyl]-4-pentynoic acid methyl ester By following a procedure analogous to Preparation 104 starting from 1-acetyl-2,3-dihydro-1H-indol-5-sulfonyl chloride, the expected product is obtained in the form of a yellow solid (yield=32%).
$^1$H NMR (DMSOd$_6$, 300 MHz) δ=2.63 (m, 4H), 3.16 (t, 2H), 3.66 (s, 3H), 4.13 (t, 2H), 7.50 (d, 1H), 7.62 (m, 4H), 8.10 (d, 1H), 9.74 (s, 1H).

Preparation 115

5-[2-[[(2,3-Dihydro-5-benzofuranyl)sulfonyl]amino]-5-(trifluoromethyl)phenyl]-4-pentynoic acid methyl ester By following a procedure analogous to Preparation 104 starting from 2,3-dihydro-5-benzofuransulfonyl chloride, the expected product is obtained in form of a yellow oil (yield=53%).

$^1$H NMR (DMSOd$_6$, 250 MHz) δ=2.66 (m, 4H), 3.20 (t, 2H), 3.66 (s, 3H), 4.63 (t, 2H), 6.88 (d, 1H), 7.59 (m, 5H), 9.65 (s, 1H).

Preparation 116

5-[2-[[[4-(4-Morpholinylsulfonyl)phenyl]sulfonyl]amino]-5-(trifluoromethyl)phenyl]-4-pentynoic acid methyl ester By following a procedure analogous to Preparation 104 starting from 4-(4-morpholinylsulfonyl)benzenesulfonyl chloride, the expected product is obtained in the form of a yellow oil (yield=56%).
$^1$H NMR (DMSOd$_6$, 250 MHz) δ=2.60 (s, 4H), 2.88 (t, 4H), 3.60 (t, 4H), 3.65 (s, 3H), 7.53 (s, 1H), 7.58 (d, 1H), 7.92 (dd, 1H), 7.99 (dd, 2H), 10.37 (s, 1H).

Preparation 117

N-(4-chloro-2-iodophenyl)-2-pyridinesulfonamide

A solution of 1 g (3.95 mM) of 4-chloro-2-iodoaniline and 0.65 ml of pyridine in 10 ml of dichloromethane is prepared and 1.68 g (9.5 mM) of 2-pyridinesulfonyl chloride are added at 0° C., with stirring. The reaction mixture is subsequently stirred at room temperature for 16 hours and then concentrated under reduced pressure. The residual oil is purified by chromatography on silica gel using a cyclohexane/ethyl acetate mixture (8/2; v/v) as the eluent to give 0.74 g of the expected product in the form of a white solid (yield=48%).
M.p.=112-124° C.

Preparation 118

6-[2-[[(6-Benzothiazolyl)sulfonyl]amino]-5-(trifluoromethyl)phenyl]-5-hexynoic acid methyl ester By following a procedure analogous to Preparation 105 starting from 6-benzothiazolesulfonyl chloride, the expected product is obtained in the form of an orange paste (yield=59%).
$^1$H NMR (DMSOd$_6$, 250 MHz) δ=1.62-1.73 (m, 2H), 2.32 (t, 2H), 2.39 (t, 2H), 3.60 (s, 3H), 7.51 (d, 1H), 7.61-7.65 (m, 2H), 7.89 (dd, 1H), 8.23 (d, 1H), 8.69 (s, 1H), 9.62 (s, 1H), 10.22 (s, 1H).

Preparation 119

5-(Trifluoromethyl)-1H-indole-2-butanoic acid methyl ester

By following a procedure analogous to Preparation 6 starting from the ester obtained according to Preparation 103, the expected product is obtained in the form of a beige solid (yield=36%).
M.p.=115° C.

Preparation 120

N-(4-chloro-2-iodophenyl)benzenesulfonamide

A solution of 2 g (7.89 mM) of 4-chloro-2-iodoaniline in 30 ml of pyridine is prepared and 1.21 ml (9.5 mM) of benzenesulfonyl chloride are added at 0° C., with stirring. The reaction mixture is subsequently stirred at room temperature for 16 hours and then concentrated under reduced pressure.

The residual oil is taken up with 50 ml of ethyl acetate and the solution obtained is washed with water and then dried over magnesium sulfate and concentrated under reduced pressure. Analysis of the crude product shows the presence of about 12% of N-(4-chloro-2-iodophenyl)-N-(phenylsulfonyl)benzenesulfonamide. The crude product is therefore taken up in solution in 60 ml of dioxane and treated with 19 ml of 3 M potassium hydroxide solution under gentle reflux for 8 hours. The solvent is driven off under reduced pressure and the residue is taken up with water and acidified to pH 2 with dilute hydrochloric acid solution. The precipitate formed is filtered off, washed with water on the filter and dried to give 2.79 g of the expected product in the form of a white solid (yield=90%).

M.p.=126-128° C.

Preparation 121

N-[2-iodo-4-(trifluoromethyl)phenyl]benzenesulfonamide

By following a procedure analogous to Preparation 120 starting from 2-iodo-4-(trifluoro-methyl)aniline, the expected product is obtained in the form of a white solid (yield=74%).

M.p.=84-86° C.

Preparation 122

2-[[3-(2-Amino-5-chlorophenyl)-2-propynyl]oxy]-2-methylpropanoic acid methyl ester A mixture of 2 g (7.89 mM) of 4-chloro-2-iodoaniline, 75 mg (0.395 mM) of cuprous iodide, 277 mg (0.39 mM) of bis(triphenylphosphine)dichloropalladium, 221 mg (0.79 mM) of tri-(cyclohexyl)phosphine, 3.08 g (19.7 mM) of the methyl ester of 2-methyl-2-(2-propynyloxy)-propanoic acid and 15 ml of tert-butylamine is prepared. The reaction mixture is refluxed gently for 16 hours and then cooled, hydrolyzed in 60 ml of water and extracted with 3×40 ml of dichloromethane. The combined organic phases are washed with water and then dried over magnesium sulfate and concentrated under reduced pressure. The residual oil is purified by chromatography on silica gel using a dichloromethane/ethyl acetate mixture (98/2; v/v) as the eluent to give 1.84 g of the expected product in the form of an orange oil (yield=83%).

$^1$H NMR (DMSOd$_6$, 250 MHz) δ=1.41 (s, 6H), 3.66 (s, 3H), 4.40 (s, 2H), 5.22 (broad s, 2H), 6.69 (d, 1H), 7.07 (dd, 1H), 7.13 (d, 1H).

Preparation 123

2-[[3-[2-[[(6-Benzothiazolyl)sulfonyl]amino]-5-chlorophenyl]-2-propynyl]oxy]-2-methylpropanoic acid methyl ester By following a procedure analogous to Preparation 117 starting from the compound obtained according to Preparation 122 and 6-benzothiazolesulfonyl chloride, the expected product is obtained in the form of a yellow oil (yield=53%).

$^1$H NMR (DMSOd$_6$, 300 MHz) δ=1.63 (s, 6H), 3.67 (s, 3H), 4.14 (s, 2H), 7.30 (d, 1H), 7.38 (d, 1H), 7.41 (dd, 1H), 7.85 (dd, 1H), 8.23 (d, 1H), 8.62 (d, 1H), 9.61 (s, 1H), 10.05 (s, 1H).

Preparation 124

2-[[3-[2-Amino-5-(trifluoromethyl)phenyl]-2-propynyl]oxy]-2-methyl-propanoic acid methyl ester By following a procedure analogous to Preparation 122 starting from 2-iodo-5-(trifluoro-methyl)aniline, the expected product is obtained in the form of an orange oil (yield=80%).

$^1$H NMR (DMSOd$_6$, 300 MHz) δ=1.42 (s, 6H), 3.65 (s, 3H), 4.41 (s, 2H), 6.08 (s, 2H), 6.79 (d, 1H), 7.34 (d, 1H), 7.39 (s, 1H).

Preparation 125

2-[[3-[2-[[(6-Benzothiazolyl)sulfonyl]amino]-5-(trifluoromethyl)phenyl]-2-propynyl]oxy]-2-methylpropanoic acid methyl ester By following a procedure analogous to Preparation 123 starting from the compound obtained according to Preparation 124 and 6-benzothiazolesulfonyl chloride, the expected product is obtained in the form of a yellow paste (yield=23%).

$^1$H NMR (DMSOd$_6$, 300 MHz) δ=1.38 (s, 6H), 3.67 (s, 3H), 4.25 (s, 2H), 7.52 (d, 1H), 7.66 (d, 2H), 7.94 (dd, 1H), 8.24 (dd, 1H), 8.72 (d, 1H), 9.63 (s, 1H), 10.33 (s, 1H).

Preparation 126

2-[[3-[2-[[(2-Methyl-6-benzothiazolyl)sulfonyl]amino]-5-chlorophenyl]-2-propynyl]oxy]-2-methyl-propanoic acid methyl ester By following a procedure analogous to Preparation 117 starting from the compound obtained according to Preparation 122 and 2-methyl-6-benzothiazolesulfonyl chloride, the expected product is obtained in the form of a yellow paste (yield=58%).

$^1$H NMR (DMSOd$_6$, 250 MHz) δ=1.36 (s, 6H), 2.84 (s, 3H), 3.68 (s, 3H), 4.14 (s, 2H), 7.28 (d, 1H), 7.36 (d, 1H), 7.40 (dd, 1H), 7.78 (dd, 1H), 8.03 (d, 1H), 8.46 (d, 1H), 9.96 (s, 1H).

Preparation 127

2-[[3-[2-[[(2-Methyl-5-benzothiazolyl)sulfonyl]amino]-5-chlorophenyl]-2-propynyl]oxy]-2-methylpropanoic acid methyl ester By following a procedure analogous to Preparation 117 starting from the compound obtained according to Preparation 122 and 2-methyl-5-benzothiazolesulfonyl chloride, the expected product is obtained in the form of a yellow oil (yield=45%).

$^1$H NMR (DMSOd$_6$, 300 MHz) δ=1.36 (s, 6H), 2.83 (s, 3H), 3.67 (s, 3H), 4.11 (s, 2H), 7.30 (d, 1H), 7.36 (d, 1H), 7.41 (dd, 1H), 7.66 (dd, 1H), 8.18 (d, 1H), 8.21 (d, 1H), 10.01 (s, 1H).

Preparation 128

2-[[3-(2-Amino-5-chlorophenyl)-2-propynyl]oxy] propanoic acid ethyl ester

By following a procedure analogous to Preparation 122 starting from the ethyl ester of 2-(2-propynyloxy)propanoic acid, the expected product is obtained in the form of an orange oil (yield=69%).

¹H NMR (DMSOd₆, 300 MHz) δ=1.19 (t, 3H), 1.31 (d, 3H), 4.13 (q, 2H), 4.25 (q, 1H), 4.42 (d, 1H), 4.53 (d, 1H), 5.56 (s, 2H), 6.69 (d, 1H), 7.08 (dd, 1H), 7.14 (d, 1H).

Preparation 129

2-[[3-[2-[[(6-Benzothiazolyl)sulfonyl]amino]-5-chlorophenyl]-2-propynyl]oxy]propanoic acid ethyl ester By following a procedure analogous to Preparation 123 starting from the compound obtained according to Preparation 128 and 6-benzothiazolesulfonyl chloride, the expected product is obtained in the form of a white solid (yield=82%).
M.p.=166-168° C.

Preparation 130

6-[2-[[(1,3-Benzodioxol-5-yl)sulfonyl]amino]-5-(trifluoromethyl)phenyl]-5-hexynoic acid methyl ester By following a procedure analogous to Preparation 118 starting from 1,3-benzodioxole-5-sulfonyl chloride, the expected product is obtained in the form of a brown oil, which is used in the next step without further purification (yield=73%).

Preparation 131

5-[2-[[[2-(Acetylamino)-6-benzothiazolyl]sulfonyl]amino]-5-(trifluoromethyl)phenyl]-4-pentynoic acid methyl ester By following a procedure analogous to Preparation 104 starting from 2-(acetylamino)-6-benzothiazolesulfonyl chloride, the expected product is obtained in the form of a brown oil, which is used in the next step without further purification (yield=66%).

Preparation 132

2-[[3-[2-[[(2-Methyl-5-benzothiazolyl)sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 2-methyl-5-benzothiazolesulfonyl chloride, the expected product is obtained in the form of an orange oil (yield=16%).
¹H NMR (DMSOd₆, 300 MHz) δ=10.30 (s, 1H), 8.27 (m, 2H), 7.76 (dd, 1H), 7.69 (m, 2H), 7.53 (d, 1H), 4.22 (s, 2H), 3.67 (s, 3H), 2.83 (s, 3H), 1.39 (s, 6H).

Preparation 133

2-[[3-[2-[(1,3-Benzodioxol-5-ylsulfonyl)amino]-5-(trifluoromethyl)phenyl]-2-propynyl]oxy]-2-methylpropanoic acid methyl ester By following a procedure analogous to Example 3 starting from the compound obtained according to Preparation 124 and 1,3-benzodioxole-5-sulfonyl chloride, the expected product is obtained in the form of a yellow oil (yield=21%).
¹H NMR (DMSOd₆, 250 MHz) δ=9.99 (s, 1H), 7.69 (m, 2H), 7.47 (d, 1H), 7.34 (m, 2H), 7.04 (d, 1H), 6.15 (s, 2H), 4.37 (s, 2H), 3.68 (s, 3H), 1.43 (s, 6H).

Preparation 134

2-[[3-[2-[[[2-(Acetylamino)-6-benzothiazolyl]sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 2-(acetylamino)-6-benzothiazolesulfonyl chloride, the expected product is obtained in the form of a white solid (yield=63%).
M.p.=104-106° C.

Preparation 135

2-[[3-[2-[(2,3-Dihydrobenzofuran-5-ylsulfonyl)amino]-5-(trifluoromethyl)phenyl]-2-propynyl]oxy]-2-methylpropanoic acid methyl ester By following a procedure analogous to Example 3 starting from the compound obtained according to Preparation 124 and 2,3-dihydro-5-benzofuransulfonyl chloride, the expected product is obtained in the form of a yellow oil (yield=87%).
¹H NMR (DMSOd₆, 250 MHz) δ=9.88 (s, 1H), 7.68 (m, 3H), 7.61 (m, 1H), 7.49 (dd, 1H), 6.88 (d, 1H), 4.63 (t, 2H), 4.38 (s, 2H), 3.68 (s, 3H), 3.22 (t, 2H), 1.43 (s, 6H).

Preparation 136

2-[[3-[2-[[(2-Methyl-7-benzothiazolyl)sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 2-methyl-7-benzothiazolesulfonyl chloride, the expected product is obtained in the form of a yellow oil (yield=44%).
¹H NMR (DMSOd₆, 250 MHz) δ=10.57 (s, 1H), 8.15 (d, 1H), 7.75 (m, 1H), 7.64 (m, 3H), 7.46 (d, 1H), 4.06 (s, 2H), 3.68 (s, 3H), 2.79 (s, 3H), 1.37 (s, 6H).

Preparation 137

2-[[3-[2-[[(2,3-Dihydro-1,4-benzodioxin-6-yl)sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 2,3-dihydro-1,4-benzodioxin-6-sulfonyl chloride, the expected product is obtained in the form of a beige paste (yield=79%).
¹H NMR (DMSOd₆, 250 MHz) δ=9.98 (s, 1H), 7.68 (m, 2H), 7.48 (d, 1H), 7.31 (m, 2H), 7.02 (d, 1H), 4.37 (s, 2H), 4.29 (m, 4H), 3.68 (s, 3H), 1.43 (s, 6H).

Preparation 138

2-[[3-[2-[[(3,4-Dihydro-4-methyl-2H-1,4-benzoxazin-7-yl)sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 3,4-dihydro-4-methyl-2H-1,4-benzoxazine-7-sulfonyl chloride, the expected product is obtained in the form of a beige solid (yield=69%).
M.p.=98-100° C.

Preparation 139

2-[[3-[2-[[(1-Acetyl-2,3-dihydro-1H-indol-5-yl)sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 1-acetyl-2,3-dihydro-1H-indole-5-sulfonyl chloride, the expected product is obtained in the form of a beige solid (yield=44%).
M.p.=134-136° C.

Preparation 140

2-[[3-[2-[[(3,5-Dimethylphenyl)sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 3,5-dimethylbenzenesulfonyl chloride, the expected product is obtained in the form of a beige solid (yield=70%).
M.p.=128-130° C.

Preparation 141

2-[[3-[2-[[(2,5-Dimethoxyphenyl)sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 2,5-dimethoxybenzenesulfonyl chloride, the expected product is obtained in the form of a yellow oil (yield=76%).
$^1$H NMR (DMSOd$_6$, 300 MHz) δ=9.13 (s, 1H), 7.13 (s, 1H), 7.66 (d, 1H), 7.56 (d, 1H), 7.32 (d, 1H), 7.20 (dd, 1H), 7.15 (d, 1H), 4.42 (s, 2H), 3.76 (s, 3H), 3.74 (s, 3H), 3.68 (s, 3H), 1.42 (s, 6H).

Preparation 142

2-[[3-[2-[[[4-(1-Methylethyl)phenyl]sulfonyl]amino]-5-(trifluoromethyl)phenyl]-2-propynyl]oxy]-2-methylpropanoic acid methyl ester By following a procedure analogous to Example 3 starting from the compound obtained according to Preparation 124 and 4-(1-methylethyl)benzenesulfonyl chloride, the expected product is obtained in the form of a yellow oil (yield=77%).
$^1$H NMR (DMSOd$_6$, 250 MHz) δ=10.08 (s, 1H), 8.23 (d, 1H), 8.03 (s, 1H), 7.92 (dd, 1H), 7.76 (d, 2H), 7.67 (m, 2H), 7.46 (m, 4H), 4.33 (s, 2H), 3.67 (s, 3H), 2.96 (hep, 1H), 1.42 (s, 6H), 1.19 (d, 6H).

Preparation 143

2-[[3-[2-[(1,3-Benzodioxol-5-ylsulfonyl)amino]-5-chlorophenyl]-2-propynyl]oxy]-2-methylpropanoic acid methyl ester By following a procedure analogous to Example 3 starting from the compound obtained according to Preparation 122 and 1,3-benzodioxole-5-sulfonyl chloride, the expected product is obtained in the form of a yellow oil (yield=55%).
$^1$H NMR (DMSOd$_6$, 250 MHz) δ=9.71 (s, 1H), 7.39 (m, 2H), 7.23 (m, 3H), 7.02 (d, 1H), 6.15 (s, 2H), 4.30 (s, 2H), 3.67 (s, 3H), 1.42 (s, 6H).

Preparation 144

2-[[3-[2-[[[2-(Acetylamino)-6-benzothiazolyl]sulfonyl]amino]-5-chlorophenyl]-2-propynyl]oxy]-2-methylpropanoic acid methyl ester By following a procedure analogous to Example 3 starting from the compound obtained according to Preparation 122 and 2-(acetylamino)-6-benzothiazolesulfonyl chloride, the expected product is obtained in the form of a yellow solid (yield=50%).
M.p.=80° C.

Preparation 145

2-[[3-[2-[[(1-Acetyl-2,3-dihydro-1H-indol-5-yl)sulfonyl]amino]-5-chlorophenyl]-2-propynyl]oxy]-2-methylpropanoic acid methyl ester By following a procedure analogous to Example 3 starting from the compound obtained according to Preparation 122 and 1-acetyl-2,3-dihydro-1H-indole-5-sulfonyl chloride, the expected product is obtained in the form of a yellow paste (yield=44%).
$^1$H NMR (DMSOd$_6$, 300 MHz) δ=9.68 (s, 1H), 8.08 (d, 1H), 7.54 (m, 2H), 7.38 (m, 2H), 7.27 (dd, 1H), 4.30 (s, 2H), 4.13 (t, 2H), 3.67 (s, 3H), 2.17 (s, 3H), 1.41 (s, 6H).

Preparation 146

2-[[3-[5-Chloro-2-[(2,3-dihydrobenzofuran-5-ylsulfonyl)amino]phenyl]-2-propynyl]oxy]-2-methylpropanoic acid methyl ester By following a procedure analogous to Example 3 starting from the compound obtained according to Preparation 122 and 2,3-dihydro-5-benzofuransulfonyl chloride, the expected product is obtained in the form of a yellow oil (yield=49%).
$^1$H NMR (DMSOd$_6$, 300 MHz) δ=9.59 (s, 1H), 7.61 (d, 1H), 7.48 (dd, 1H), 7.39 (m, 2H), 7.27 (d, 1H), 6.85 (d, 1H), 4.62 (t, 2H), 4.28 (s, 2H), 3.64 (s, 3H), 3.21 (t, 2H), 1.42 (s, 6H).

Preparation 147

2-[[3-[5-Chloro-2-[[(2-methyl-7-benzothiazolyl)sulfonyl]amino]phenyl]-2-propynyl]oxy]-2-methylpropanoic acid methyl ester By following a procedure analogous to Example 3 starting from the compound obtained according to Preparation 122 and 2-methyl-7-benzothiazolesulfonyl chloride, the expected product is obtained in the form of a yellow oil (yield=33%).
$^1$H NMR (DMSOd$_6$, 300 MHz) δ=10.30 (s, 1H), 8.14 (dd, 1H), 7.64 (m, 2H), 7.41 (dd, 1H), 7.32 (d, 1H), 7.26 (d, 1H), 3.91 (s, 2H), 3.67 (s, 3H), 2.79 (s, 3H), 1.34 (s, 6H).

Preparation 148

2-[[3-[5-Chloro-2-[[(2,3-dihydro-1,4-benzodioxin-6-yl)sulfonyl]amino]phenyl]-2-propynyl]oxy]-2-methylpropanoic acid methyl ester By following a procedure analogous to Example 3 starting from the compound obtained according to Preparation 122 and 2,3-dihydro-1,4-benzodioxin-6-sulfonyl chloride, the expected product is obtained in the form of a yellow oil (yield=94%).

$^1$H NMR (DMSOd$_6$, 250 MHz) δ=9.70 (s, 1H), 7.40 (m, 2H), 7.24 (m, 3H), 6.97 (d, 1H), 4.28 (m, 6H), 3.67 (s, 3H), 1.41 (s, 6H).

Preparation 149

2-[[3-[5-Chloro-2-[[(3,4-dihydro-4-methyl-2H-1,4-benzoxazin-7-yl)sulfonyl]-amino]phenyl]-2-propynyl]oxy]-2-methylpropanoic acid methyl ester By following a procedure analogous to Example 3 starting from the compound obtained according to Preparation 122 and 3,4-dihydro-4-methyl-2H-1,4-benzoxazin-7-sulfonyl chloride, the expected product is obtained in the form of a beige solid (yield=69%).

M.p.=98-100° C.

Preparation 150

2-[[3-[5-Chloro-2-[[[4-(1-methylethyl)phenyl]sulfonyl]amino]phenyl]-2-propynyl]oxy]-2-methylpropanoic acid methyl ester By following a procedure analogous to Example 3 starting from the compound obtained according to Preparation 122 and 4-(1-methylethyl)benzenesulfonyl chloride, the expected product is obtained in the form of a beige solid (yield=86%).

M.p.=65-67° C.

Preparation 151

2-[[3-[5-Chloro-2-[[(3,5-dimethylphenyl)sulfonyl]amino]phenyl]-2-propynyl]oxy]-2-methylpropanoic acid methyl ester By following a procedure analogous to Example 3 starting from the compound obtained according to Preparation 122 and 3,5-dimethylbenzenesulfonyl chloride, the expected product is obtained in the form of a white solid (yield=62%).

M.p.=78-80° C.

Preparation 152

2-[[3-[5-Chloro-2-[[(2,5-dimethoxyphenyl)sulfonyl]amino]phenyl]-2-propynyl]oxy]-2-methylpropanoic acid methyl ester By following a procedure analogous to Example 3 starting from the compound obtained according to Preparation 122 and 2,5-dimethoxybenzenesulfonyl chloride, the expected product is obtained in the form of a yellow oil (yield=90%).

$^1$H NMR (DMSOd$_6$, 250 MHz) δ=8.93 (s, 1H), 7.43 (d, 1H), 7.35 (m, 2H), 7.25 (d, 1H), 7.17 (m, 2H), 4.36 (s, 2H), 3.77 (s, 3H), 3.73 (s, 3H), 3.68 (s, 3H), 1.41 (s, 6H).

Preparation 153

2-[[3-[5-Chloro-2-[[(4-methoxyphenyl)sulfonyl]amino]phenyl]-2-propynyl]oxy]-2-methylpropanoic acid methyl ester By following a procedure analogous to Example 3 starting from the compound obtained according to Preparation 122 and 4-methoxybenzenesulfonyl chloride, the expected product is obtained in the form of a beige solid (yield=83%).

M.p.=98-100° C.

Preparation 154

2-[[3-[5-Chloro-2-[[(2-methyl-6-benzothiazolyl)sulfonyl]amino]phenyl]-2-propynyl]oxy]propanoic acid ethyl ester By following a procedure analogous to Example 3 starting from the compound obtained according to Preparation 128 and 2-methyl-6-benzothiazolesulfonyl chloride, the expected product is obtained in the form of a yellow paste (yield=49%).

$^1$H NMR (DMSOd$_6$, 300 MHz) δ=10.04 (s, 1H), 8.45 (d, 1H), 8.03 (d, 1H), 7.78 (dd, 1H), 7.41 (m, 2H), 7.27 (dd, 1H), 4.34 (d, 1H), 4.16 (m, 4H), 2.83 (s, 3H), 1.29 (d, 3H), 1.19 (t, 3H).

Preparation 155

2-[[3-[5-Chloro-2-[[(2,3-dihydro-1,4-benzodioxin-6-yl)sulfonyl]amino]phenyl]-2-propynyl]oxy]propanoic acid ethyl ester By following a procedure analogous to Example 3 starting from the compound obtained according to Preparation 128 and 2,3-dihydro-1,4-benzodioxin-6-sulfonyl chloride, the expected product is obtained in the form of a yellow oil (yield=65%).

$^1$H NMR (DMSOd$_6$, 300 MHz) δ=9.78 (s, 1H), 7.43 (dd, 2H), 7.25 (d, 1H), 7.19 (m, 2H), 6.97 (d, 1H), 4.45 (d, 1H), 4.29 (m, 6H), 4.14 (m, 2H), 1.33 (d, 3H), 1.21 (t, 3H).

Preparation 156

2-[[3-[5-Chloro-2-[[(3,4-dihydro-4-methyl-2H-1,4-benzoxazin-7-yl)sulfonyl]-amino]phenyl]-2-propynyl]oxy]propanoic acid ethyl ester By following a procedure analogous to Example 3 starting from the compound obtained according to Preparation 128 and 3,4-dihydro-4-methyl-2H-1,4-benzoxazine-7-sulfonyl chloride, the expected product is obtained in the form of a yellow oil (yield=63%).

$^1$H NMR (DMSOd$_6$, 300 MHz) δ=9.57 (s, 1H), 7.41 (m, 2H), 7.26 (d, 1H), 6.93 (m, 2H), 6.74 (d, 1H), 4.45 (d, 1H), 4.26 (m, 4H), 4.15 (m, 2H), 3.26 (m, 2H), 2.79 (s, 3H), 1.32 (d, 3H), 1.21 (t, 3H).

Preparation 157

2-[[3-[5-Chloro-2-[[(3,5-dimethyl-4-isoxazolyl)sulfonyl]amino]phenyl]-2-propynyl]oxy]propanoic acid ethyl ester By following a procedure analogous to Example 3 starting from the compound obtained according to Preparation 128 and 3,5-dimethyl-4-isoxazolesulfonyl chloride, the expected product is obtained in the form of a yellow oil (yield=30%).

$^1$H NMR (DMSOd$_6$, 300 MHz) δ=10.29 (s, 1H), 7.52 (m, 2H), 7.37 (d, 1H), 4.43 (d, 1H), 4.26 (m, 2H), 4.15 (m, 2H), 2.27 (s, 3H), 2.16 (s, 3H), 1.32 (d, 3H), 1.22 (t, 3H).

Preparation 158

2-[[3-[5-Chloro-2-[[(2,5-dimethoxyphenyl)sulfonyl] amino]phenyl]-2-propynyl]-oxy]propanoic acid ethyl ester By following a procedure analogous to Example 3 starting from the compound obtained according to Preparation 128 and 2,5-dimethoxybenzenesulfonyl chloride, the expected product is obtained in the form of a yellow oil (yield=62%).

$^1$H NMR (DMSOd$_6$, 300 MHz) δ=9.11 (s, 1H), 7.46 (d, 1H), 7.37 (d, 1H), 7.29 (m, 1H), 7.24 (m, 1H), 7.16 (m, 2H), 4.49 (d, 1H), 4.36 (d, 1H), 4.24 (q, 1H), 4.16 (m, 2H), 3.75 (s, 3H), 3.72 (s, 3H), 1.31 (d, 3H), 1.21 (t, 3H).

Preparation 159

2-[[3-[2-Amino-5-(trifluoromethyl)phenyl]-2-propynyl]oxy]propanoic acid ethyl ester By following a procedure analogous to Preparation 122 starting from the compound obtained according to Preparation 4 and the ethyl ester of 2-(2-propynyloxy)propanoic acid, the expected product is obtained in the form of an orange oil (yield=82%).

$^1$H NMR (DMSOd$_6$, 300 MHz) δ=7.42 (d, 1H), 7.35 (dd, 1H), 6.80 (d, 1H), 6.11 (s, 2H), 4.54 (d, 1H), 4.43 (d, 1H), 4.27 (q, 1H), 4.11 (m, 2H), 1.32 (d, 3H), 1.20 (t, 3H).

Preparation 160

2-[[3-[2-[[(2-Methyl-6-benzothiazolyl)sulfonyl] amino]-5-(trifluoromethyl)phenyl]-2-propynyl]oxy] propanoic acid ethyl ester By following a procedure analogous to Example 3 starting from the compound obtained according to Preparation 159 and 2-methyl-6-benzothiazolesulfonyl chloride, the expected product is obtained in the form of a yellow oil (yield=44%).

$^1$H NMR (DMSOd$_6$, 300 MHz) δ=10.33 (s, 1H), 8.55 (d, 1H), 8.06 (d, 1H), 7.87 (dd, 1H), 6.68 (m, 2H), 7.50 (d, 1H), 4.43 (d, 1H), 4.26 (m, 2H), 4.15 (m, 2H), 2.84 (s, 3H), 1.31 (d, 3H), 1.20 (t, 3H).

Preparation 161

2-[[3-[2-[[(6-Benzothiazolyl)sulfonyl]amino]-5-(trifluoromethyl)phenyl]-2-propynyl]oxy]propanoic acid ethyl ester By following a procedure analogous to Example 3 starting from the compound obtained according to Preparation 159 and 6-benzothiazolesulfonyl chloride, the expected product is obtained in the form of a pale yellow solid (yield=28%).

M.p.=112-114° C.

Preparation 162

2-[[3-[2-[[(2,3-Dihydro-1,4-benzodioxin-6-yl)sulfonyl]amino]-5-(trifluoromethyl)phenyl]-2-propynyl] oxy]propanoic acid ethyl ester By following a procedure analogous to Example 3 starting from the compound obtained according to Preparation 159 and 2,3-dihydro-1,4-benzodioxin-6-sulfonyl chloride, the expected product is obtained in the form of a yellow oil (yield=68%).

$^1$H NMR (DMSOd$_6$, 300 MHz) δ=10.07 (s, 1H), 7.70 (m, 2H), 7.48 (d, 1H), 7.29 (m, 2H), 7.00 (d, 1H), 4.51 (d, 1H), 4.38 (d, 1H), 4.31 (m, 5H), 4.16 (m, 2H), 1.34 (d, 3H), 1.20 (t, 3H).

Preparation 163

2-[[3-[2-[[(3,4-Dihydro-4-methyl-2H-1,4-benzoxazin-7-yl)sulfonyl]amino]-5-(trifluoromethyl)phenyl]-2-propynyl]oxy]propanoic acid ethyl ester By following a procedure analogous to Example 3 starting from the compound obtained according to Preparation 159 and 3,4-dihydro-4-methyl-2H-1,4-benzoxazine-7-sulfonyl chloride, the expected product is obtained in the form of a yellow oil (yield=57%).

$^1$H NMR (DMSOd$_6$, 300 MHz) δ=9.88 (s, 1H), 7.69 (m, 2H), 7.49 (d, 1H), 7.02 (m, 2H), 7.78 (d, 1H), 4.51 (d, 1H), 4.37 (d, 1H), 4.28 (m, 3H), 4.15 (m, 2H), 3.27 (m, 2H), 2.80 (s, 3H), 1.33 (d, 3H), 1.20 (t, 3H).

Preparation 164

2-[[3-[2-[[(2,5-Dimethoxyphenyl)sulfonyl]amino]-5-(trifluoromethyl)phenyl]-2-propynyl]oxy]propanoic acid ethyl ester By following a procedure analogous to Example 3 starting from the compound obtained according to Preparation 159 and 2,5-dimethoxybenzenesulfonyl chloride, the expected product is obtained in the form of a yellow oil (yield=65%).

$^1$H NMR (DMSOd$_6$, 250 MHz) δ=9.29 (s, 1H), 7.74 (s, 1H), 7.67 (d, 1H), 7.56 (d, 1H), 7.31 (d, 1H), 7.18 (m, 2H), 4.55 (d, 1H), 4.41 (d, 1H), 4.25 (q, 1H), 4.13 (m, 2H), 3.74 (s, 6H), 1.32 (d, 3H), 1.20 (t, 3H).

Preparation 165

(2S)-2-[[3-[2-amino-5-chlorophenyl]-2-propynyl] oxy]propanoic acid ethyl ester a)—Ethyl ester of (2S)-2-(2-propynyloxy)propanoic acid: This compound is obtained with a yield of 24% by reacting propargyl bromide with the ethyl ester of (S)-(−)-lactic acid which has been treated beforehand with sodium hydride in tetrahydrofuran (b.p.=70-73° C. under 13 hPa).

b)—By following a procedure analogous to Preparation 122 starting from the ethyl ester of (2S)-2-(2-propynyloxy)propanoic acid, the expected product is obtained in the form of a yellow oil (yield=99%).

$^1$H NMR (DMSOd$_6$, 300 MHz) δ=7.14 (d, 1H), 7.08 (dd, 1H), 6.69 (d, 1H), 5.56 (s, 2H), 4.53 (d, 1H), 4.42 (d, 1H), 4.25 (q, 1H), 4.13 (m, 2H), 1.30 (d, 3H), 1.21 (t, 3H).

Preparation 166

(2S)-2-[[3-[5-chloro-2-[[(6-benzothiazolyl)sulfonyl] amino]phenyl]-2-propynyl]-oxy]propanoic acid ethyl ester By following a procedure analogous to Example 3 starting from the compound obtained according to Preparation 165 and 6-benzothiazolesulfonyl chloride, the expected product is obtained in the form of a white solid (yield=43%).

¹H NMR (DMSOd₆, 300 MHz) δ=10.11 (s, 1H), 9.61 (s, 1H), 8.60 (d, 1H), 8.22 (d, 1H), 7.84 (dd, 1H), 7.40 (m, 2H), 7.30 (d, 1H), 4.32 (d, 1H), 4.15 (m, 4H), 1.28 (d, 3H), 1.21 (t, 3H).

Preparation 167

(2R)-2-[[3-[2-amino-5-chlorophenyl]-2-propynyl]oxy]propanoic acid methyl ester a)—Methyl ester of (2R)-2-(2-propynyloxy)propanoic acid: This compound is obtained with a yield of 9.5% by reacting propargyl bromide with the methyl ester of (R)-(+)-lactic acid which has been treated beforehand with sodium hydride in tetrahydrofuran (b.p.=81-88° C. at atmospheric pressure).
b)—By following a procedure analogous to Preparation 122 starting from the methyl ester of (2R)-2-(2-propynyloxy)propanoic acid, the expected product is obtained in the form of a yellow oil (yield=89%).
¹H NMR (DMSOd₆, 300 MHz) δ=7.14 (d, 1H), 7.08 (dd, 1H), 6.69 (d, 1H), 5.57 (s, 2H), 4.53 (d, 1H), 4.41 (d, 1H), 4.25 (q, 1H), 3.66 (s, 3H), 1.31 (d, 3H).

Preparation 168

(2R)-2-[[3-[5-chloro-2-[[(6-benzothiazolyl)sulfonyl]amino]phenyl]-2-propynyl]-oxy]propanoic acid methyl ester By following a procedure analogous to Example 3 starting from the compound obtained according to Preparation 167 and 6-benzothiazolesulfonyl chloride, the expected product is obtained in the form of a white solid (yield=65%).
M.p.=136° C.

Preparation 169

6-[5-Chloro-2-[[(2-methyl-7-benzothiazolyl)sulfonyl]amino]phenyl]-5-hexynoic acid methyl ester By following a procedure analogous to Preparation 55 starting from 2-methyl-7-benzothiazolesulfonyl chloride, the expected product is obtained in the form of a brown oil (yield=97%).
¹H NMR (DMSOd₆, 300 MHz) δ=10.21 (s, 1H), 8.13 (m, 1H), 7.60 (m, 2H), 7.38 (dd, 1H), 7.28 (m, 2H), 3.61 (s, 3H), 2.78 (s, 3H), 2.33 (t, 2H), 2.04 (t, 2H), 1.55 (quin, 2H).

Preparation 170

6-[2-[[(1-Acetyl-1H-indol-5-yl)sulfonyl]amino]-5-chlorophenyl]-5-hexynoic acid methyl ester By following a procedure analogous to Preparation 55 starting from 1-acetyl-1H-indole-5-sulfonyl chloride, the expected product is obtained in the form of a brown oil (yield=79%).
¹H NMR (DMSOd₆, 300 MHz) δ=9.72 (s, 1H), 8.42 (d, 1H), 8.00 (d, 1H), 7.99 (d, 1H), 7.62 (dd, 1H), 7.33 (m, 3H), 6.87 (d, 1H), 3.59 (s, 3H), 2.67 (s, 3H), 2.35 (t, 2H), 2.27 (y, 2H), 1.64 (quin, 2H).

Preparation 171

5-[5-Chloro-2-[[(2-methyl-7-benzothiazolyl)sulfonyl]amino]phenyl]-4-pentynoic acid methyl ester By following a procedure analogous to Example 3 starting from the compound obtained according to Preparation 2 and 2-methyl-7-benzothiazolesulfonyl chloride, the expected product is obtained in the form of an amorphous solid (yield=45%).
¹H NMR (DMSOd₆, 300 MHz) δ=10.15 (s, 1H), 8.15 (m, 1H), 7.60 (m, 2H), 7.40 (dd, 1H), 7.31 (d, 1H), 7.23 (d, 1H), 3.63 (s, 3H), 2.79 (s, 3H), 2.37 (m, 2H), 2.25 (m, 2H).

Preparation 172

5-[2-[[(2-Amino-6-benzoxazolyl)sulfonyl]amino]-5-chlorophenyl]-4-pentynoic acid methyl ester By following a procedure analogous to Example 3 starting from the compound obtained according to Preparation 2 and 2-amino-6-benzoxazolesulfonyl chloride, the expected product is obtained in the form of a white solid (yield=9%).
M.p.=170-171° C.

Preparation 173

5-[5-Chloro-2-[[(2,3-dihydro-5-benzofuranyl)sulfonyl]amino]phenyl]-4-pentynoic acid methyl ester By following a procedure analogous to Example 3 starting from the compound obtained according to Preparation 2 and 2,3-dihydro-5-benzofuransulfonyl chloride, the expected product is obtained in the form of an amorphous solid (yield=98%).
¹H NMR (DMSOd₆, 300 MHz) δ=9.39 (s, 1H), 7.60 (d, 1H), 7.44 (dd, 1H), 7.31 (m, 3H), 6.85 (d, 1H), 4.62 (t, 2H), 3.65 (s, 3H), 3.21 (t, 2H), 2.60 (m, 4H).

Preparation 174

5-[2-[[(2-Amino-6-benzothiazolyl)sulfonyl]amino]-5-chlorophenyl]-4-pentynoic acid methyl ester By following a procedure analogous to Example 3 starting from the compound obtained according to Preparation 2 and 2-amino-6-benzothiazolesulfonyl chloride, the expected product is obtained in the form of a white solid (yield=93%).
M.p.=175° C.

Preparation 175

N-(2-bromo-4-methylphenyl)-6-benzothiazolesulfonamide

By following a procedure analogous to Example 3 starting from 2-bromo-4-methylaniline and 6-benzothiazolesulfonyl chloride, the expected product is obtained in the form of an orange solid (yield=76%).
M.p.=171-174° C.

Preparation 176

N-(2-bromo-4-methylphenyl)benzenesulfonamide

By following a procedure analogous to Preparation 120 starting from 2-bromo-4-methylaniline, the expected product is obtained in the form of a beige solid (yield=95%).

$^1$H NMR (DMSOd$_6$, 250 MHz) δ=9.75 (s, 1H), 7.69 (m, 3H), 7.63 (m, 2H), 7.40 (s, 1H), 7.09 (d, 1H), 7.02 (d, 1H), 2.23 (s, 3H).

Preparation 177

N-(4-chloro-2-iodophenyl)-6-benzothiazolesulfonamide

By following a procedure analogous to Preparation 120 starting from 6-benzothiazolesulfonyl chloride and using tetrabutylammonium fluoride in reaction in THF to remove the dicondensed compound, the expected product is obtained in the form of a yellow solid (yield=91%).

M.p.=162° C.

Preparation 178

6-[5-Chloro-2-[[(4-fluoro-3-nitrophenyl)sulfonyl]amino]phenyl]-5-hexynoic acid methyl ester By following a procedure analogous to Preparation 55 starting from 4-fluoro-3-nitrobenzenesulfonyl chloride and using triethylamine as a basic agent, the expected product is obtained in the form of an orange oil (yield=98%).

$^1$H NMR (DMSOd$_6$, 300 MHz) δ=10.31 (s, 1H), 8.38 (dd, 1H), 8.00 (m, 1H), 7.81 (dd, 1H), 7.41 (s, 1H), 7.38 (m, 1H), 7.23 (m, 1H), 3.60 (s, 3H), 2.41 (t, 2H), 2.34 (t, 2H), 1.68 (quin, 2H).

Example 9

1-(Phenylsulfonyl)-1H-indole-2-propanoic acid methyl ester

By following a procedure analogous to Example 1 starting from the compound obtained according to Preparation 24, the expected product is obtained in the form of a white solid (yield=75%).

M.p.=95-99° C.

Example 10

1-(Phenylsulfonyl)-1H-indole-2-propanoic acid

By following a procedure analogous to Example 2 starting from the compound obtained according to Example 9, the expected product is obtained in the form of a white solid (yield=99%).

M.p.=180-185° C.

Example 11

5-Chloro-1-[(4-methylphenyl)sulfonyl]-1H-indole-2-propanoic acid methyl ester

By following a procedure analogous to Example 1 starting from the compound obtained according to Preparation 25, the expected product is obtained in the form of a beige solid (yield=89%).

M.p.=100-103° C.

Example 12

5-Chloro-1-[(4-methylphenyl)sulfonyl]-1H-indole-2-propanoic acid

By following a procedure analogous to Example 2 starting from the compound obtained according to Example 11, the expected product is obtained in the form of a beige solid (yield=93%).

M.p.=165-168° C.

Example 13

5-Chloro-1-[(2,3-dichlorophenyl)sulfonyl]-1H-indole-2-propanoic acid methyl ester By following a procedure analogous to Example 1 starting from the compound obtained according to Preparation 26, the expected product is obtained in the form of a yellow oil (yield=96%).

$^1$H NMR (DMSOd$_6$, 300 MHz) δ=2.77 (t, 2H), 3.15 (t, 2H), 3.59 (s, 3H), 6.65 (s, 1H), 7.26 (dd, 1H), 7.67 (m, 3H), 7.84 (dd, 1H), 8.04 (dd, 1H).

Example 14

5-Chloro-1-[(2,3-dichlorophenyl)sulfonyl]-1H-indole-2-propanoic acid

By following a procedure analogous to Example 2 starting from the compound obtained according to Example 13, the expected product is obtained in the form of a white solid (yield=76%).

M.p.=163-166° C.

Example 15

5-Chloro-1-[(3-methylphenyl)sulfonyl]-1H-indole-2-propanoic acid methyl ester

By following a procedure analogous to Example 1 starting from the compound obtained according to Preparation 27, the expected product is obtained in the form of a beige solid (yield=68%).

M.p.=105-108° C.

Example 16

5-Chloro-1-[(3-methylphenyl)sulfonyl]-1H-indole-2-propanoic acid

By following a procedure analogous to Example 2 starting from the compound obtained according to Example 15, the expected product is obtained in the form of a white solid (yield=92%).

M.p.=161-165° C.

Example 17

5-Chloro-1-[(2,4-dichlorophenyl)sulfonyl]-1H-indole-2-propanoic acid methyl ester By following a procedure analogous to Example 1 starting from the compound obtained according to Preparation 28, the expected product is obtained in the form of a yellow oil (yield=83%).

¹H NMR (DMSOd₆, 300 MHz) δ=2.76 (t, 2H), 3.15 (t, 2H), 3.59 (s, 3H), 6.63 (s, 1H), 7.26 (dd, 1H), 7.71 (m, 3H), 7.94 (m, 2H).

Example 18

5-Chloro-1-[(2,4-dichlorophenyl)sulfonyl]-1H-indole-2-propanoic acid

By following a procedure analogous to Example 2 starting from the compound obtained according to Example 17, the expected product is obtained in the form of a white solid (yield 76%).
M.p.=179-181° C.

Example 19

5-Chloro-1-[[4-(trifluoromethyl)phenyl]sulfonyl]-1H-indole-2-propanoic acid methyl ester By following a procedure analogous to Example 1 starting from the compound obtained according to Preparation 29, the expected product is obtained in the form of a yellow solid (yield=97%).
M.p.=82-86° C.

Example 20

5-Chloro-1-[[4-(trifluoromethyl)phenyl]sulfonyl]-1H-indole-2-propanoic acid

By following a procedure analogous to Example 2 starting from the compound obtained according to Example 19, the expected product is obtained in the form of a beige solid (yield=78%).
M.p.=179-182° C.

Example 21

5-Chloro-1-[(4-methoxyphenyl)sulfonyl]-1H-indole-2-propanoic acid methyl ester

By following a procedure analogous to Example 1 starting from the compound obtained according to Preparation 30, the expected product is obtained in the form of a yellow solid (yield=68%).
M.p.=98-99° C.

Example 22

5-Chloro-1-[(4-methoxyphenyl)sulfonyl]-1H-indole-2-propanoic acid

By following a procedure analogous to Example 2 starting from the compound obtained according to Example 21, the expected product is obtained in the form of a white solid (yield=86%).
M.p.=95-98° C.

Example 23

1-[(4-Acetylphenyl)sulfonyl]-5-chloro-1H-indole-2-propanoic acid methyl ester

By following a procedure analogous to Example 1 starting from the compound obtained according to Preparation 31, the expected product is obtained in the form of a yellow solid (yield=93%).
M.p.=83-87° C.

Example 24

1-[(4-Acetylphenyl)sulfonyl]-5-chloro-1H-indole-2-propanoic acid

By following a procedure analogous to Example 2 starting from the compound obtained according to Example 23, the expected product is obtained in the form of a yellow solid (yield=70%).
M.p.=159-161° C.

Example 25

5-Chloro-1-[(4-phenylphenyl)sulfonyl]-1H-indole-2-propanoic acid methyl ester

By following a procedure analogous to Example 1 starting from the compound obtained according to Preparation 32, the expected product is obtained in the form of a yellow oil (yield=58%).
¹H NMR (DMSOd₆, 250 MHz) δ=2.84 (t, 2H), 3.37 (t, 2H), 3.62 (s, 3H), 6.62 (s, 1H), 7.34 (dd, 1H), 7.47 (m, 3H), 7.61 (s, 1H), 7.68 (dd, 2H), 7.88 (d, 4H), 8.07 (d, 1H).

Example 26

5-Chloro-1-[(4-phenylphenyl)sulfonyl]-1H-indole-2-propanoic acid

By following a procedure analogous to Example 2 starting from the compound obtained according to Example 25, the expected product is obtained in the form of a white solid (yield=78%).
M.p.=160-162° C.

Example 27

5-Chloro-1-[(3-methoxyphenyl)sulfonyl]-1H-indole-2-propanoic acid methyl ester

By following a procedure analogous to Example 1 starting from the compound obtained according to Preparation 34, the expected product is obtained in the form of a yellow solid (yield=63%).
M.p.=106-109° C.

Example 28

5-Chloro-1-[(3-methoxyphenyl)sulfonyl]-1H-indole-2-propanoic acid

By following a procedure analogous to Example 2 starting from the compound obtained according to Example 27, the expected product is obtained in the form of a white solid (yield=62%).
M.p.=182-184° C.

Example 29

5-Chloro-1-[(2,5-dimethoxyphenyl)sulfonyl]-1H-indole-2-propanoic acid methyl ester By following a procedure analogous to Example 1 starting from the compound obtained according to Preparation 35, the expected product is obtained in the form of a yellow solid (yield=85%).
M.p.=120-124° C.

Example 30

5-Chloro-1-[(2,5-dimethoxyphenyl)sulfonyl]-1H-indole-2-propanoic acid

By following a procedure analogous to Example 2 starting from the compound obtained according to Example 29, the expected product is obtained in the form of a white solid (yield=88%).
M.p.=185-189° C.

Example 31

5-Chloro-1-[[4-(1,1-dimethylethyl)phenyl]sulfonyl]-1H-indole-2-propanoic acid methyl ester By following a procedure analogous to Example 1 starting from the compound obtained according to Preparation 36, the expected product is obtained in the form of a beige solid (yield=87%).
M.p.=130-133° C.

Example 32

5-Chloro-1-[[4-(1,1-dimethylethyl)phenyl]sulfonyl]-1H-indole-2-propanoic acid By following a procedure analogous to Example 2 starting from the compound obtained according to Example 31, the expected product is obtained in the form of a white solid (yield=98%).
M.p.=169-171° C.

Example 33

5-Chloro-1-[(4-ethylphenyl)sulfonyl]-1H-indole-2-propanoic acid methyl ester By following a procedure analogous to Example 1 starting from the compound obtained according to Preparation 37, the expected product is obtained in the form of a yellow oil (yield=86%).
$^1$H NMR (DMSOd$_6$, 300 MHz) δ=1.12 (t, J=7.56 Hz, 3H), 2.63 (q, 2H), 2.81 (t, J=7.62 Hz, 2H), 3.28 (t, J=4.08 Hz, 2H), 3.61 (s, 3H), 6.57 (s, 1H), 7.31 (dd, J=8.9 Hz, 2.22 Hz, 1H), 7.45 (d, J=12.8 Hz, 2H), 7.59 (s, 1H), 7.74 (d, J=12.78 Hz, 2H), 8.02 (d, J=8.91, 1H).

Example 34

5-Chloro-1-[(4-ethylphenyl)sulfonyl]-1H-indole-2-propanoic acid

By following a procedure analogous to Example 2 starting from the compound obtained according to Example 33, the expected product is obtained in the form of a white solid (yield=70%).
M.p.=130-133° C.

Example 35

5-Chloro-1-[[4-(1-methylethyl)phenyl]sulfonyl]-1H-indole-2-propanoic acid methyl ester By following a procedure analogous to Example 1 starting from the compound obtained according to Preparation 38, the expected product is obtained in the form of a white solid (yield=58%).
M.p.=90-94° C.

Example 36

5-Chloro-1-[[4-(1-methylethyl)phenyl]sulfonyl]-1H-indole-2-propanoic acid

By following a procedure analogous to Example 2 starting from the compound obtained according to Example 35, the expected product is obtained in the form of a white solid (yield=70%).
M.p.=150-154° C.

Example 37

5-Chloro-1-[(4-propylphenyl)sulfonyl]-1H-indole-2-propanoic acid methyl ester By following a procedure analogous to Example 1 starting from the compound obtained according to Preparation 39, the expected product is obtained in the form of a white solid (yield=87%).
M.p.=85-88° C.

Example 38

5-Chloro-1-[(4-propylphenyl)sulfonyl]-1H-indole-2-propanoic acid

By following a procedure analogous to Example 2 starting from the compound obtained according to Example 37, the expected product is obtained in the form of a yellow solid (yield=92%).
M.p.=144-148° C.

Example 39

5-Chloro-1-[(4-pentylphenyl)sulfonyl]-1H-indole-2-propanoic acid methyl ester By following a procedure analogous to Example 1 starting from the compound obtained according to Preparation 40, the expected product is obtained in the form of a yellow oil (yield=76%).
$^1$H NMR (DMSOd$_6$, 300 MHz) δ=0.81 (t, 3H), 1.22 (m, 4H), 1.50 (m, 2H), 2.58 (t, 2H), 2.81 (t, 2H), 3.28 (t, 2H), 3.61 (s, 3H), 6.58 (s, 1H), 7.31 (dd, 1H), 7.39 (d, 2H), 7.59 (d, 1H), 7.72 (d, 2H), 8.02 (d, 1H).

Example 40

5-Chloro-1-[(4-pentylphenyl)sulfonyl]-1H-indole-2-propanoic acid

By following a procedure analogous to Example 2 starting from the compound obtained according to Example 39, the expected product is obtained in the form of a white solid (yield=79%).
M.p.=131-134° C.

Example 41

5-Chloro-1-[(3,5-dimethylphenyl)sulfonyl]-1H-indole-2-propanoic acid methyl ester By following a procedure analogous to Example 1 starting from the compound obtained according to Preparation 41, the expected product is obtained in the form of a white solid (yield=90%).
M.p.=146-150° C.

Example 42

5-Chloro-1-[(3,5-dimethylphenyl)sulfonyl]-1H-indole-2-propanoic acid

By following a procedure analogous to Example 2 starting from the compound obtained according to Example 41, the expected product is obtained in the form of a white solid (yield=88%).
M.p.=189-193° C.

Example 43

5-Chloro-1-[(2,4,6-trimethylphenyl)sulfonyl]-1H-indole-2-propanoic acid methyl ester By following a procedure analogous to Example 1 starting from the compound obtained according to Preparation 42, the expected product is obtained in the form of a white solid (yield=75%).
M.p.=145-148° C.

Example 44

5-Chloro-1-[(2,4,6-trimethylphenyl)sulfonyl]-1H-indole-2-propanoic acid

By following a procedure analogous to Example 2 starting from the compound obtained according to Example 43, the expected product is obtained in the form of a white solid (yield 50%).
M.p.=132-134° C.

Example 45

5-Chloro-1-[(4-chlorophenyl)sulfonyl]-1H-indole-2-propanoic acid methyl ester By following a procedure analogous to Example 1 starting from the compound obtained according to Preparation 43, the expected product is obtained in the form of a white solid (yield=98%).
M.p.=89-92° C.

Example 46

5-Chloro-1-[(4-chlorophenyl)sulfonyl]-1H-indole-2-propanoic acid

By following a procedure analogous to Example 2 starting from the compound obtained according to Example 45, the expected product is obtained in the form of a white solid (yield=81%).
M.p.=158-160° C.

Example 47

5-Chloro-1-[(4-fluorophenyl)sulfonyl]-1H-indole-2-propanoic acid methyl ester By following a procedure analogous to Example 1 starting from the compound obtained according to Preparation 44, the expected product is obtained in the form of a white solid (yield=79%).
M.p.=129-131° C.

Example 48

5-Chloro-1-[(4-fluorophenyl)sulfonyl]-1H-indole-2-propanoic acid

By following a procedure analogous to Example 2 starting from the compound obtained according to Example 47, the expected product is obtained in the form of a white solid (yield=78%).
M.p.=145-148° C.

Example 49

5-Chloro-1-[(4-chloro-3-methylphenyl)sulfonyl]-1H-indole-2-propanoic acid methyl ester By following a procedure analogous to Example 1 starting from the compound obtained according to Preparation 45, the expected product is obtained in the form of a yellow oil (yield=59%).
$^1$H NMR (DMSOd$_6$, 300 MHz) δ=2.35 (s, 3H), 2.82 (t, 2H), 3.27 (t, 2H), 3.60 (s, 3H), 6.61 (s, 1H), 7.31 (dd, 1H), 7.62 (m, 3H), 7.90 (s, 1H), 8.00 (d, J=9.48, 1H).

Example 50

5-Chloro-1-[(4-chloro-3-methylphenyl)sulfonyl]-1H-indole-2-propanoic acid

By following a procedure analogous to Example 2 starting from the compound obtained according to Example 49, the expected product is obtained in the form of a white solid (yield=81%).
M.p.=160-164° C.

Example 51

5-Chloro-1-[[3-(trifluoromethyl)phenyl]sulfonyl]-1H-indole-2-propanoic acid methyl ester By following a procedure analogous to Example 1 starting from the compound obtained according to Preparation 46, the expected product is obtained in the form of a white solid (yield=39%).
M.p.=98-100° C.

Example 52

5-Chloro-1-[[3-(trifluoromethyl)phenyl]sulfonyl]-1H-indole-2-propanoic acid

By following a procedure analogous to Example 2 starting from the compound obtained according to Example 51, the expected product is obtained in the form of a white solid (yield=81%).
M.p.=203-206° C.

Example 53

1-[[4-(Acetylamino)phenyl]sulfonyl]-5-chloro-1H-indole-2-propanoic acid methyl ester By following a procedure analogous to Example 1 starting from the compound obtained according to Preparation 47, the expected product is obtained in the form of a beige solid (yield=71%).
M.p.=154-157° C.

Example 54

5-Chloro-1-[(4-cyanophenyl)sulfonyl]-1H-indole-2-propanoic acid methyl ester By following a procedure analogous to Example 1 starting from the compound obtained according to Preparation 48, the expected product is obtained in the form of a beige solid (yield=72%).
M.p.=155-159° C.

Example 55

5-Chloro-1-[(4-phenoxyphenyl)sulfonyl]-1H-indole-2-propanoic acid methyl ester By following a procedure analogous to Example 1 starting from the compound obtained according to Preparation 49, the expected product is obtained in the form of a yellow oil (yield=80%).
$^1$H NMR (DMSOd$_6$, 300 MHz) δ=2.81 (t, 2H), 3.27 (t, 2H), 3.61 (s, 3H), 6.59 (s, 1H), 7.02-7.13 (m, 4H), 7.30 (m, 2H), 7.45 (m, 2H), 7.60 (s, 1H), 7.83 (d, 2H), 8.01 (d, 1H).

Example 56

5-Chloro-1-[(4-phenoxyphenyl)sulfonyl]-1H-indole-2-propanoic acid

By following a procedure analogous to Example 2 starting from the compound obtained according to Example 55, the expected product is obtained in the form of a white solid (yield 93%).
M.p.=70-75° C.

Example 57

5-Chloro-1-[(1-naphthalenyl)sulfonyl]-1H-indole-2-propanoic acid methyl ester By following a procedure analogous to Example 1 starting from the compound obtained according to Preparation 50, the expected product is obtained in the form of a yellow solid (yield=80%).
M.p.=88-93° C.

Example 58

5-Chloro-1-[(1-naphthalenyl)sulfonyl]-1H-indole-2-propanoic acid

By following a procedure analogous to Example 2 starting from the compound obtained according to Example 57, the expected product is obtained in the form of a white solid (yield=98%).
M.p.=165-175° C.

Example 59

5-Chloro-1-[(2-naphthalenyl)sulfonyl]-1H-indole-2-propanoic acid methyl ester By following a procedure analogous to Example 1 starting from the compound obtained according to Preparation 51, the expected product is obtained in the form of a yellow oil (yield=90%).
$^1$H NMR (DMSOd$_6$, 300 MHz) δ=2.84 (t, 2H), 3.35 (t, 2H), 3.60 (s, 3H), 6.59 (s, 1H), 7.31 (dd, 1H), 7.57 (s, 1H), 7.69 (m, 3H), 7.99-8.2 (m, 4H), 8.72 (s, 1H).

Example 60

5-Chloro-1-[(2-naphthalenyl)sulfonyl]-1H-indole-2-propanoic acid

By following a procedure analogous to Example 2 starting from the compound obtained according to Example 59, the expected product is obtained in the form of a white solid (yield=48%).
M.p.=160° C.

Example 61

5-Chloro-1-[(4-methyl-1-naphthalenyl)sulfonyl]-1H-indole-2-propanoic acid methyl ester By following a procedure analogous to Example 1 starting from the compound obtained according to Preparation 52, the expected product is obtained in the form of a yellow oil (yield=94%).
$^1$H NMR (DMSOd$_6$, 300 MHz) δ=2.72 (t, 5H), 3.14 (t, 2H), 3.57 (s, 3H), 6.64 (s, 1H), 7.30 (dd, 1H), 7.53 (m, 2H), 7.69 (m, 3H), 7.92 (d, 1H), 8.21 (m, 1H), 8.37 (m, 1H).

Example 62

5-Chloro-1-[(4-methyl-1-naphthalenyl)sulfonyl]-1H-indole-2-propanoic acid

By following a procedure analogous to Example 2 starting from the compound obtained according to Example 61, the expected product is obtained in the form of a white solid (yield=95%).
M.p.=190-196° C.

Example 63

5-Chloro-1-[[5-(aminoacetyl)-1-naphthalenyl]sulfonyl]-1H-indole-2-propanoic acid methyl ester By following a procedure analogous to Example 1 starting from the compound obtained according to Preparation 53, the expected product is obtained in the form of a yellow solid (yield=66%).
M.p.=206-210° C.

Example 64

5-Chloro-1-[[5-(aminoacetyl)-1-naphthalenyl]sulfonyl]-1H-indole-2-propanoic acid By following a procedure analogous to Example 2 starting from the compound obtained according to Example 63, the expected product is obtained in the form of a white solid (yield=96%).
M.p.=130-135° C.

Example 65

5-Chloro-1-[(8-quinolinyl)sulfonyl]-1H-indole-2-propanoic acid methyl ester

By following a procedure analogous to Example 1 starting from the compound obtained according to Preparation 54, the expected product is obtained in the form of a brown solid (yield=78%).
M.p.=157-161° C.

Example 66

5-Chloro-1-[(8-quinolinyl)sulfonyl]-1H-indole-2-propanoic acid

By following a procedure analogous to Example 2 starting from the compound obtained according to Example 65, the expected product is obtained in the form of a brown solid (yield=80%).
M.p.=215-222° C.

Example 67

5-Chloro-1-(phenylsulfonyl)-1H-indole-2-butanoic acid methyl ester

By following a procedure analogous to Example 1 starting from the compound obtained according to Preparation 55, the expected product is obtained in the form of a white solid (yield=81%).
M.p.=109-112° C.

Example 68

5-Chloro-1-(phenylsulfonyl)-1H-indole-2-butanoic acid

By following a procedure analogous to Example 2 starting from the compound obtained according to Example 67, the expected product is obtained in the form of a pale pink solid (yield=92%).
M.p.=198-202° C.

Example 69

5-Chloro-1-[(2,3-dichlorophenyl)sulfonyl]-1H-indole-2-butanoic acid methyl ester By following a procedure analogous to Example 1 starting from the compound obtained according to Preparation 56, the expected product is obtained in the form of a pink powder (yield=72%).
M.p.=115-117° C.

Example 70

5-Chloro-1-[(2,3-dichlorophenyl)sulfonyl]-1H-indole-2-butanoic acid

By following a procedure analogous to Example 2 starting from the compound obtained according to Example 69, the expected product is obtained in the form of a white powder (yield=93%).
M.p.=195-197° C.

Example 71

5-Chloro-1-[(4-methoxyphenyl)sulfonyl]-1H-indole-2-butanoic acid methyl ester

By following a procedure analogous to Example 1 starting from the compound obtained according to Preparation 57, the expected product is obtained in the form of a yellow powder (yield=98%).
M.p.=97-98° C.

Example 72

5-Chloro-1-[(4-methoxyphenyl)sulfonyl]-1H-indole-2-butanoic acid

By following a procedure analogous to Example 2 starting from the compound obtained according to Example 71, the expected product is obtained in the form of a pink powder (yield=96%).
M.p.=138-142° C.

Example 73

5-Chloro-1-[(8-quinolinyl)sulfonyl]-1H-indole-2-butanoic acid methyl ester

By following a procedure analogous to Example 1 starting from the compound obtained according to Preparation 58, the expected product is obtained in the form of a pink powder (yield=93%).
M.p.=120-124° C.

Example 74

5-Chloro-1-[(8-quinolinyl)sulfonyl]-1H-indole-2-butanoic acid

By following a procedure analogous to Example 2 starting from the compound obtained according to Example 73, the expected product is obtained in the form of a white powder (yield=64%).
M.p.=217-219° C.

Example 75

5-Chloro-1-[[4-(1-methylethyl)phenyl]sulfonyl]-1H-indole-2-butanoic acid methyl ester By following a procedure analogous to Example 1 starting from the compound obtained according to Preparation 59, the expected product is obtained in the form of a pink powder (yield=81%).
M.p.=95-97° C.

Example 76

5-Chloro-1-[[4-(1-methylethyl)phenyl]sulfonyl]-1H-indole-2-butanoic acid

By following a procedure analogous to Example 2 starting from the compound obtained according to Example 75, the expected product is obtained in the form of a white powder (yield=95%).
M.p.=148° C.

Example 77

5-Chloro-1-[(2-naphthalenyl)sulfonyl]-1H-indole-2-butanoic acid methyl ester

By following a procedure analogous to Example 1 starting from the compound obtained according to Preparation 60, the expected product is obtained in the form of a white powder (yield=71%).
M.p.=116-118° C.

Example 78

5-Chloro-1-[(2-naphthalenyl)sulfonyl]-1H-indole-2-butanoic acid

By following a procedure analogous to Example 2 starting from the compound obtained according to Example 77, the expected product is obtained in the form of a white powder (yield=90%).
M.p.=166° C.

Example 79

5-Chloro-1-[(3,5-dimethylphenyl)sulfonyl]-1H-indole-2-butanoic acid methyl ester By following a procedure analogous to Example 1 starting from the compound obtained according to Preparation 61, the expected product is obtained in the form of a white powder (yield=81%).
M.p.=140-143° C.

Example 80

5-Chloro-1-[(3,5-dimethylphenyl)sulfonyl]-1H-indole-2-butanoic acid

By following a procedure analogous to Example 2 starting from the compound obtained according to Example 79, the expected product is obtained in the form of a white powder (yield=91%).
M.p.=204-206° C.

Example 81

5-Chloro-1-[(3-methoxyphenyl)sulfonyl]-1H-indole-2-butanoic acid methyl ester

By following a procedure analogous to Example 1 starting from the compound obtained according to Preparation 62, the expected product is obtained in the form of a white powder (yield=87%).
M.p.=107-109° C.

Example 82

5-Chloro-1-[(3-methoxyphenyl)sulfonyl]-1H-indole-2-butanoic acid

By following a procedure analogous to Example 2 starting from the compound obtained according to Example 81, the expected product is obtained in the form of a white powder (yield=79%).
M.p.=170-172° C.

Example 83

5-Chloro-1-[(2,5-dimethoxyphenyl)sulfonyl]-1H-indole-2-butanoic acid methyl ester By following a procedure analogous to Example 1 starting from the compound obtained according to Preparation 63, the expected product is obtained in the form of a white powder (yield=92%).
M.p.=152-154° C.

Example 84

5-Chloro-1-[(2,5-dimethoxyphenyl)sulfonyl]-1H-indole-2-butanoic acid

By following a procedure analogous to Example 2 starting from the compound obtained according to Example 83, the expected product is obtained in the form of a white powder (yield=92%).
M.p.=201-209° C.

Example 85

5-Chloro-1-[(1-naphthalenyl)sulfonyl]-1H-indole-2-butanoic acid methyl ester

By following a procedure analogous to Example 1 starting from the compound obtained according to Preparation 64, the expected product is obtained in the form of a cream-colored powder (yield=44%).
M.p.=94-97° C.

Example 86

5-Chloro-1-[(1-naphthalenyl)sulfonyl]-1H-indole-2-butanoic acid

By following a procedure analogous to Example 2 starting from the compound obtained according to Example 85, the expected product is obtained in the form of a white powder (yield=89%).
M.p.=206-210° C.

Example 87

5-Fluoro-1-(phenylsulfonyl)-1H-indole-2-propanoic acid methyl ester

By following a procedure analogous to Example 3 starting from the compound obtained according to Preparation 65, the expected product is obtained in the form of beige crystals (yield=58%).
M.p.=79-80° C.

Example 88

5,6-Dichloro-1-(phenylsulfonyl)-1H-indole-2-propanoic acid methyl ester

By following a procedure analogous to Example 3 starting from the compound obtained according to Preparation 66, the expected product is obtained in the form of a white solid (yield=23%).
M.p.=280° C.

Example 89

5,6-Dichloro-1-(phenylsulfonyl)-1H-indole-2-propanoic acid

By following a procedure analogous to Example 2 starting from the compound obtained according to Example 88, the expected product is obtained in the form of a fine pink powder (yield=61%).
M.p.=192-198° C.

Example 90

4,5-Dichloro-1-(phenylsulfonyl)-1H-indole-2-propanoic acid methyl ester

By following a procedure analogous to Example 3 starting from the compound obtained according to Preparation 67, the expected product is obtained in the form of a yellow solid (yield=68%).
M.p.=142° C.

Example 91

4,5-Dichloro-1-(phenylsulfonyl)-1H-indole-2-propanoic acid

By following a procedure analogous to Example 2 starting from the compound obtained according to Example 90, the expected product is obtained in the form of a white powder (yield=52%).
M.p.=220° C.

Example 92

1-(Phenylsulfonyl)-6-(trifluoromethyl)-1H-indole-2-propanoic acid methyl ester By following a procedure analogous to Example 3 starting from the compound obtained according to Preparation 68, the expected product is obtained in the form of white crystals (yield=38%).
M.p.=112-114° C.

Example 93

1-(Phenylsulfonyl)-6-(trifluoromethyl)-1H-indole-2-propanoic acid

By following a procedure analogous to Example 2 starting from the compound obtained according to Example 92, the expected product is obtained in the form of white crystals (yield=72%).
M.p.=168-169° C.

Example 94

5-Acetyl-1-(phenylsulfonyl)-1H-indole-2-propanoic acid methyl ester

By following a procedure analogous to Example 3 starting from the compound obtained according to Preparation 69, the expected product is obtained in the form of a white solid (yield=41%).
M.p.=122-127° C.

Example 95

5-Acetyl-1-(phenylsulfonyl)-1H-indole-2-propanoic acid

By following a procedure analogous to Example 2 starting from the compound obtained according to Example 94, the expected product is obtained in the form of a white powder (yield=83%).
M.p.=175-181° C.

Example 96

6-Chloro-5-fluoro-1-(phenylsulfonyl)-1H-indole-2-propanoic acid methyl ester By following a procedure analogous to Example 3 starting from the compound obtained according to Preparation 70, the expected product is obtained in the form of a beige solid (yield=51%).
M.p.=127-130° C.

Example 97

6-Chloro-5-fluoro-1-(phenylsulfonyl)-1H-indole-2-propanoic acid

By following a procedure analogous to Example 2 starting from the compound obtained according to Example 96, the expected product is obtained in the form of a brown solid (yield=94%).
M.p.=199-204° C.

Example 98

5,7-Dichloro-1-(phenylsulfonyl)-1H-indole-2-propanoic acid methyl ester

By following a procedure analogous to Example 3 starting from the compound obtained according to Preparation 71, the expected product is obtained in the form of a yellow oil (yield=74%).
$^1$H NMR (DMSOd$_6$, 250 MHz) δ=2.77 (t, 2H), 3.24 (t, 2H), 3.61 (s, 3H), 6.73 (s, 1H), 7.40 (d, 1H), 7.55-7.65 (m, 3H), 7.65-7.8 (m, 3H).

Example 99

5,7-Dichloro-1-(phenylsulfonyl)-1H-indole-2-propanoic acid

By following a procedure analogous to Example 2 starting from the compound obtained according to Example 98, the expected product is obtained in the form of a yellow oil (yield=73%).
$^1$H NMR (DMSOd$_6$, 250 MHz) δ=2.63 (t, 2H), 3.19 (t, 2H), 6.71 (s, 1H), 7.40 (d, 1H), 7.55-7.85 (m, 6H).

Example 100

5-Cyano-1-(phenylsulfonyl)-1H-indole-2-propanoic acid methyl ester

By following a procedure analogous to Example 3 starting from the compound obtained according to Preparation 72, the expected product is obtained in the form of a yellow oil (yield=12%).
$^1$H NMR (DMSOd$_6$, 250 MHz) δ=2.84 (t, 2H), 3.31 (t, 2H), 3.61 (s, 3H), 6.72 (s, 1H), 7.55-7.9 (m, 6H), 8.07 (d, 1H), 8.20 (d, 1H).

Example 101

5-Cyano-1-(phenylsulfonyl)-1H-indole-2-propanoic acid

By following a procedure analogous to Example 2 starting from the compound obtained according to Example 100, the expected product is obtained in the form of a white solid (yield=67%).
M.p.=187-190° C.

Example 102

5-Benzoyl-1-(phenylsulfonyl)-1H-indole-2-propanoic acid methyl ester

By following a procedure analogous to Example 3 starting from the compound obtained according to Preparation 73, the expected product is obtained in the form of a yellow solid (yield=43%).
M.p.=37-51° C.

Example 103

5-Benzoyl-1-(phenylsulfonyl)-1H-indole-2-propanoic acid

By following a procedure analogous to Example 2 starting from the compound obtained according to Example 102, the expected product is obtained in the form of a yellow solid (yield=83%).
M.p.=138° C.

Example 104

5-Chloro-1-(phenylsulfonyl)-1H-indole-2-pentanoic acid methyl ester

By following a procedure analogous to Example 1 starting from the compound obtained according to Preparation 74, the expected product is obtained in the form of a beige solid (yield=75%).
M.p.=95-98° C.

Example 105

5-Chloro-1-(phenylsulfonyl)-1H-indole-2-pentanoic acid

By following a procedure analogous to Example 2 starting from the compound obtained according to Example 104, the expected product is obtained in the form of a white solid (yield=79%).
M.p.=144-148° C.

Example 106

1-(Phenylsulfonyl)-5-(trifluoromethoxy)-1H-indole-2-propanoic acid methyl ester

By following a procedure analogous to Preparations 1, 2 and 3 and Example 1 starting from 2-iodo-4-(trifluoromethoxy)-1-nitrobenzene, the expected product is obtained in the form of a yellow oil (yield of the final step=64%).
$^1$H NMR (DMSOd$_6$, 300 MHz) δ=2.82 (t, 2H), 3.30 (t, 2H), 3.62 (s, 3H), 6.66 (s, 1H), 7.28 (ddd, 1H), 7.53-7.57 (m, 1H), 7.57-7.64 (m, 1H), 7.68-7.75 (m, 1H), 7.83-7.88 (m, 1H), 8.11 (d, J=9.1 Hz, 1H).

Example 107

1-(Phenylsulfonyl)-5-(trifluoromethoxy)-1H-indole-2-propanoic acid

By following a procedure analogous to Example 2 starting from the compound obtained according to Example 106, the expected product is obtained in the form of a beige solid (yield=98%).
M.p.=138-146° C.

Example 108

5-Chloro-1-(phenylsulfonyl)-1H-indole-2-propanoic acid 1-methylethyl ester

A mixture of 130 mg (0.34 mM) of the methyl ester obtained according to Example 1, 3 ml of isopropanol (1-methylethanol) and 8.6 mg (0.34 mM) of dibutyltin oxide is refluxed for 40 hours. The reaction medium is then concentrated under reduced pressure and the residual oil is taken up in 10 ml of ethyl acetate. The organic phase obtained is washed with sodium bicarbonate solution and then with water and finally dried over magnesium sulfate and concentrated under reduced pressure. The product obtained is purified by chromatography on silica gel using a toluene/ethyl acetate mixture (9/1; v/v) as the eluent to give 96 mg of the expected ester in the form of a yellow oil (yield=69%).
$^1$H NMR (DMSOd$_6$, 300 MHz) δ=1.14 (d, 6H), 2.75 (t, 2H), 3.26 (t, 2H), 4.89 (m, 1H), 6.57 (s, 1H), 7.31 (dd, 1H), 7.58 (m, 3H), 7.69 (d, 1H), 7.82 (d, 2H), 8.02 (d, 1H).

Example 109

5-Chloro-1-[(3,4-dihydro-4-methyl-2H-1,4-benzoxazin-7-yl)sulfonyl]-1H-indole-2-butanoic acid methyl ester By following a procedure analogous to Preparation 6 starting from the compound obtained according to Preparation 75, the expected product is obtained in the form of a white powder (yield=90%).
M.p.=139-140° C.

Example 110

5-Chloro-1-[(3,4-dihydro-4-methyl-2H-1,4-benzoxazin-7-yl)sulfonyl]-1H-indole-2-butanoic acid By following a procedure analogous to Example 2 starting from the compound obtained according to Example 109, the expected product is obtained in the form of a white powder (yield=94%).
M.p.=164-166° C.

Example 111

5-Chloro-1-[[1,2,3,4-tetrahydro-2-(trifluoroacetyl)-7-isoquinolinyl]sulfonyl]-1H-indole-2-butanoic acid methyl ester By following a procedure analogous to Preparation 6 starting from the compound obtained according to Preparation 76, the expected product is obtained in the form of a pink powder (yield=89%).
M.p.=111-114° C.

Example 112

5-Chloro-1-[[1,2,3,4-tetrahydro-7-isoquinolinyl]sulfonyl]-1H-indole-2-butanoic acid methyl ester By following a procedure analogous to Example 2 starting from the compound obtained according to Example 111, the expected product is obtained in the form of a white powder (yield=74%).
M.p.=176-182° C.

Example 113

5-Chloro-1-[[1,2,3,4-tetrahydro-7-isoquinolinyl]sulfonyl]-1H-indole-2-butanoic acid By following a procedure analogous to Example 2 using 1.6 equivalents of lithium hydroxide and starting from the compound obtained according to Example 112, the expected product is obtained in the form of a white powder (yield=63%).

M.p.>250° C.

Example 114

5-Chloro-1-[(2,3-dihydro-1,4-benzodioxin-6-yl)sulfonyl]-1H-indole-2-butanoic acid methyl ester By following a procedure analogous to Preparation 6 starting from the compound obtained according to Preparation 77, the expected product is obtained in the form of a pink solid (yield=87%).

M.p.=101-104° C.

Example 115

5-Chloro-1-[(2,3-dihydro-1,4-benzodioxin-6-yl)sulfonyl]-1H-indole-2-butanoic acid By following a procedure analogous to Example 2 starting from the compound obtained according to Example 114, the expected product is obtained in the form of a white powder (yield=95%).

M.p.=131-134° C.

Example 116

5-Chloro-1-[(6-benzothiazolyl)sulfonyl]-1H-indole-2-butanoic acid methyl ester By following a procedure analogous to Preparation 6 starting from the compound obtained according to Preparation 78, the expected product is obtained in the form of a yellow powder (yield=61%).

M.p.=121-123° C.

Example 117

5-Chloro-1-[(6-benzothiazolyl)sulfonyl]-1H-indole-2-butanoic acid

By following a procedure analogous to Example 2 starting from the compound obtained according to Example 116, the expected product is obtained in the form of a pale yellow powder (yield=83%).

M.p.=74-80° C.

Example 118

5-chloro-1-[[6-(4-morpholinyl)-3-pyridinyl]sulfonyl]-1H-indole-2-butanoic acid methyl ester By following a procedure analogous to Preparation 6 starting from the compound obtained according to Preparation 79, the expected product is obtained in the form of a white powder (yield=89%).

M.p.=130-132° C.

Example 119

5-Chloro-1-[[6-(4-morpholinyl)-3-pyridinyl]sulfonyl]-1H-indole-2-butanoic acid By following a procedure analogous to Example 2 starting from the compound obtained according to Example 118, the expected product is obtained in the form of a white powder (yield=99%).

M.p.=78-82° C.

Example 120

5-Chloro-1-[(3,5-dimethyl-4-isoxazolyl)sulfonyl]-1H-indole-2-butanoic acid methyl ester By following a procedure analogous to Preparation 6 starting from the compound obtained according to Preparation 80, the expected product is obtained in the form of a yellow powder (yield=91%).

M.p.=96-98° C.

Example 121

5-Chloro-1-[(3,5-dimethyl-4-isoxazolyl)sulfonyl]-1H-indole-2-butanoic acid

By following a procedure analogous to Example 2 starting from the compound obtained according to Example 120, the expected product is obtained in the form of a white powder (yield=98%).

M.p.=150-154° C.

Example 122

5-Chloro-1-[(1,3,5-trimethyl-1H-pyrazol-4-yl)sulfonyl]-1H-indole-2-butanoic acid methyl ester By following a procedure analogous to Preparation 6 starting from the compound obtained according to Preparation 81, the expected product is obtained in the form of a white powder (yield=73%).

M.p.=125-127° C.

Example 123

5-Chloro-1-[(1,3,5-trimethyl-1H-pyrazol-4-yl)sulfonyl]-1H-indole-2-butanoic acid By following a procedure analogous to Example 2 starting from the compound obtained according to Example 122, the expected product is obtained in the form of a pinkish powder (yield=98%).

M.p.=142-145° C.

Example 124

5-Chloro-1-[(1-methyl-1H-imidazol-4-yl)sulfonyl]-1H-indole-2-butanoic acid methyl ester By following a procedure analogous to Preparation 6 starting from the compound obtained according to Preparation 82, the expected product is obtained in the form of a beige powder (yield=42%).
M.p.=163-165° C.

Example 125

5-Chloro-1-[(1-methyl-1H-imidazol-4-yl)sulfonyl]-1H-indole-2-butanoic acid

By following a procedure analogous to Example 2 starting from the compound obtained according to Example 124, the expected product is obtained in the form of a beige powder (yield=87%).
M.p.=222-225° C.

Example 126

5-Chloro-1-[(2,1,3-benzothiadiazol-4-yl)sulfonyl]-1H-indole-2-butanoic acid methyl ester By following a procedure analogous to Preparation 6 starting from the compound obtained according to Preparation 83, the expected product is obtained in the form of a yellow powder (yield=89%).
M.p.=123-126° C.

Example 127

5-Chloro-1-[(2,1,3-benzothiadiazol-4-yl)sulfonyl]-1H-indole-2-butanoic acid

By following a procedure analogous to Example 2 starting from the compound obtained according to Example 126, the expected product is obtained in the form of a yellow powder (yield=89%).

Example 128

5-Chloro-1-[(2,1,3-benzothiadiazol-5-yl)sulfonyl]-1H-indole-2-butanoic acid methyl ester By following a procedure analogous to Preparation 6 starting from the compound obtained according to Preparation 84, the expected product is obtained in the form of a yellow powder (yield=83%).
M.p.=103-106° C.

Example 129

5-Chloro-1-[(2,1,3-benzothiadiazol-5-yl)sulfonyl]-1H-indole-2-butanoic acid

By following a procedure analogous to Example 2 starting from the compound obtained according to Example 128, the expected product is obtained in the form of a brown powder (yield=92%).
M.p.=172-175° C.

Example 130

5-Chloro-1-[(3,4-dihydro-2,2-dimethyl-2H-1-benzopyran-6-yl)sulfonyl]-1H-indole-2-butanoic acid methyl ester By following a procedure analogous to Preparation 6 starting from the compound obtained according to Preparation 85, the expected product is obtained in the form of a pink powder (yield=94%).
M.p.=126-129° C.

Example 131

5-Chloro-[(3,4-dihydro-2,2-dimethyl-2H-1-benzopyran-6-yl)sulfonyl]-1H-indole-2-butanoic acid By following a procedure analogous to Example 2 starting from the compound obtained according to Example 130, the expected product is obtained in the form of a white powder (yield=88%).
M.p.=166-169° C.

Example 132

5-Chloro-1-[(5,6,7,8-tetrahydro-5,5,8,8-tetramethyl-2-naphthalenyl)sulfonyl]-1H-indole-2-butanoic acid methyl ester By following a procedure analogous to Preparation 6 starting from the compound obtained according to Preparation 86, the expected product is obtained in the form of an oil (yield=89%).
$^1$H NMR (DMSOd$_6$, 300 MHz) δ=1.12 (s, 6H), 1.17 (s, 6H), 1.58 (s, 4H), 1.90-2.00 (m, 2H), 2.41 (t, 2H), 3.00 (t, 2H), 3.58 (s, 3H), 6.61 (s, 1H), 7.33 (dd, 1H), 7.46-7.62 (m, 4H), 8.09 (d, 1H).

Example 133

5-Chloro-1-[(5,6,7,8-tetrahydro-5,5,8,8-tetramethyl-2-naphthalenyl)sulfonyl]-1H-indole-2-butanoic acid By following a procedure analogous to Example 2 starting from the compound obtained according to Example 132, the expected product is obtained in the form of a white powder (yield=95%).
M.p.=64-66° C.

Example 134

1-[(1-Acetyl-2,3-dihydro-1H-indol-5-yl)sulfonyl]-5-chloro-1H-indole-2-butanoic acid methyl ester By following a procedure analogous to Preparation 6 starting from the compound obtained according to Preparation 87, the expected product is obtained in the form of a white powder (yield=82%).
M.p.=162-165° C.

Example 135

1-[(1-Acetyl-2,3-dihydro-1H-indol-5-yl)sulfonyl]-5-chloro-1H-indole-2-butanoic acid By following a procedure analogous to Example 2 starting from the compound obtained according to Example 134, the expected product is obtained in the form of a white powder (yield=94%).
M.p.=115-117° C.

Example 136

5-Chloro-1-[(2-methyl-6-benzothiazolyl)sulfonyl]-1H-indole-2-butanoic acid methyl ester By following a procedure analogous to Preparation 6 starting from the compound obtained according to Preparation 88, the expected product is obtained in the form of a white powder (yield=74%).
M.p.=151-153° C.

Example 137

5-Chloro-1-[(2-methyl-6-benzothiazolyl)sulfonyl]-1H-indole-2-butanoic acid

By following a procedure analogous to Example 2 starting from the compound obtained according to Example 136, the expected product is obtained in the form of a white powder (yield=85%).
M.p.=163-165° C.

Example 138

1-[[2-(Acetylamino)-6-benzothiazolyl]sulfonyl]-5-chloro-1H-indole-2-butanoic acid methyl ester By following a procedure analogous to Preparation 6 starting from the compound obtained according to Preparation 89, the expected product is obtained in the form of a beige powder (yield=63%).
M.p.=120° C.

Example 139

1-[[2-(Acetylamino)-6-benzothiazolyl]sulfonyl]-5-chloro-1H-indole-2-butanoic acid By following a procedure analogous to Example 2 starting from the compound obtained according to Example 138, the expected product is obtained in the form of a white solid (yield=70%).
M.p.>250° C.

Example 140

5-Chloro-1-[(2-methyl-6-benzoxazolyl)sulfonyl]-1H-indole-2-butanoic acid methyl ester By following a procedure analogous to Preparation 6 starting from the compound obtained according to Preparation 91, the expected product is obtained in the form of a white solid (yield=83%).
M.p.=100-110° C.

Example 141

5-Chloro-1-[(2,3-dihydro-5-benzofuranyl)sulfonyl]-1H-indole-2-butanoic acid methyl ester By following a procedure analogous to Preparation 6 starting from the compound obtained according to Preparation 92, the expected product is obtained in the form of a white solid (yield=85%).
M.p.=132-137° C.

Example 142

5-Chloro-1-[(2,3-dihydro-5-benzofuranyl)sulfonyl]-1H-indole-2-butanoic acid

By following a procedure analogous to Example 2 starting from the compound obtained according to Example 141, the expected product is obtained in the form of a white solid (yield=98%).
M.p.=174-179° C.

Example 143

5-Chloro-1-[(2-methyl-5-benzothiazolyl)sulfonyl]-1H-indole-2-butanoic acid methyl ester By following a procedure analogous to Preparation 6 starting from the compound obtained according to Preparation 93, the expected product is obtained in the form of a yellow powder (yield=77%).
M.p.=136-138° C.

Example 144

5-Chloro-1-[(2-methyl-5-benzothiazolyl)sulfonyl]-1H-indole-2-butanoic acid

By following a procedure analogous to Example 2 starting from the compound obtained according to Example 143, the expected product is obtained in the form of a white powder (yield=98%).
M.p.=164° C.

Example 145

1-[(2-Amino-6-benzoxazolyl)sulfonyl]-5-chloro-1H-indole-2-butanoic acid methyl ester By following a procedure analogous to Preparation 6 starting from the compound obtained according to Preparation 94, the expected product is obtained in the form of a yellow powder (yield=46%).
M.p.=238° C.

Example 146

1-[(2-Amino-6-benzoxazolyl)sulfonyl]-5-chloro-1H-indole-2-butanoic acid

By following a procedure analogous to Example 2 starting from the compound obtained according to Example 145, the expected product is obtained in the form of a yellow powder (yield=76%).
M.p.=220° C.

Example 147

1-[[2-(Acetylamino)-4-methyl-5-thiazolyl]sulfonyl]-5-chloro-1H-indole-2-butanoic acid methyl ester By following a procedure analogous to Preparation 6 starting from the compound obtained according to Preparation 95, the expected product is obtained in the form of a yellow powder (yield=36%).
M.p.=156-160° C.

Example 148

1-[[2-(Acetylamino)-4-methyl-5-thiazolyl]sulfonyl]-5-chloro-1H-indole-2-butanoic acid By following a procedure analogous to Example 2 starting from the compound obtained according to Example 147, the expected product is obtained in the form of a white powder (yield=74%).
M.p.=231-233° C.

Example 149

5-Chloro-1-[(1,2,3,4-tetrahydro-2-oxo-6-quinolinyl)sulfonyl]-1H-indole-2-butanoic acid methyl ester By following a procedure analogous to Preparation 6 starting from the compound obtained according to Preparation 96, the expected product is obtained in the form of a white powder (yield=19%).
M.p.=198-205° C.

Example 150

1-[(2-Acetyl-1,2,3,4-tetrahydro-7-isoquinolinyl)sulfonyl]-5-chloro-1H-indole-2-butanoic acid methyl ester A solution of 1.25 g (2.8 mM) of the compound obtained according to Example 112 in 12 ml of dichloromethane is prepared and 0.860 ml (6.17 mM) of triethylamine is added, followed by the dropwise addition of 0.2 ml of acetyl chloride. The reaction mixture is stirred at room temperature for 2 hours and then poured into 15 ml of iced water. The mixture is decanted, the aqueous phase is extracted with 20 ml of dichloromethane and the combined organic phases are washed with water and then dried over magnesium sulfate and concentrated under reduced pressure. The residual oil is purified by chromatography on silica gel using a dichloromethane/methanol mixture (99/1; v/v) as the eluent. This gives 0.93 g of the expected compound in the form of a white powder (yield=67%).
M.p.=50-52° C.

Example 151

1-[(2-acetyl-1,2,3,4-tetrahydro-7-isoquinolinyl)sulfonyl]-5-chloro-1H-indole-2-butanoic acid By following a procedure analogous to Example 2 starting from the compound obtained according to Example 150, the expected product is obtained in the form of a white powder (yield=98%).
M.p.=95-97° C.

Example 152

5-Chloro-1-[(2-pyridinyl)sulfonyl]-1H-indole-2-butanoic acid methyl ester

A solution of 350 mg (0.89 mM) of N-(4-chloro-2-iodophenyl)-2-pyridinesulfonamide (Preparation 117) in 6 ml of dimethylformamide is prepared and 10 ml of diethylamine, 8 mg (0.042 mM) of cuprous iodide, 16 mg (0.02 mM) of bis(triphenylphosphine)dichloropalladium and, finally, 134 mg (1.06 mM) of the methyl ester of 5-hexynoic acid are added. The mixture is stirred at the reflux temperature of the solvents for 1 hour and then at room temperature overnight. After hydrolysis in 20 ml of water, the mixture is extracted with 40 ml of ethyl acetate. The organic phase obtained is washed with N hydrochloric acid solution and then with sodium chloride solution, dried over magnesium sulfate and concentrated under reduced pressure. The oily residue is purified by chromatography on silica gel using a cyclohexane/ethyl acetate mixture (80/20; v/v) as the eluent to give 0.23 g of the expected compound in the form of a brown solid (yield=84%).
M.p.=94° C.

Example 153

5-Chloro-1-[(2-pyridinyl)sulfonyl]-1H-indole-2-butanoic acid

By following a procedure analogous to Example 2 starting from the compound obtained according to Example 152, the expected product is obtained in the form of a white powder (yield=97%).
M.p.=192° C.

Example 154

1-[(6-Benzothiazolyl)sulfonyl]-5-chloro-1H-indole-2-propanoic acid methyl ester

By following a procedure analogous to Preparation 6 starting from the compound obtained according to Preparation 97, the expected product is obtained in the form of a yellow powder (yield=73%).
M.p.=134-138° C.

Example 155

1-[(6-Benzothiazolyl)sulfonyl]-5-chloro-1H-indole-2-propanoic acid

By following a procedure analogous to Example 2 starting from the compound obtained according to Example 154, the expected product is obtained in the form of a white powder (yield=96%).
M.p.=96-100° C.

Example 156

1-[[2-(acetylamino)-6-benzothiazolyl]sulfonyl]-5-chloro-1H-indole-2-propanoic acid methyl ester By following a procedure analogous to Preparation 6 starting from the compound obtained according to Preparation 98, the expected product is obtained in the form of a beige powder (yield 60%).
M.p.=217-221° C.

Example 157

1-[[2-(Acetylamino)-6-benzothiazolyl]sulfonyl]-5-chloro-1H-indole-2-propanoic acid By following a procedure analogous to Example 2 starting from the compound obtained according to Example 156, the expected product is obtained in the form of a white powder (yield=88%).
M.p.>250° C.

Example 158

1-[(1-Acetyl-2,3-dihydro-1H-indol-5-yl)sulfonyl]-5-chloro-1H-indole-2-propanoic acid methyl ester By following a procedure analogous to Preparation 6 starting from the compound obtained according to Preparation 99, the expected product is obtained in the form of a beige powder (yield=89%).
M.p.=129° C.

Example 159

1-[(1-Acetyl-2,3-dihydro-1H-indol-5-yl)sulfonyl]-5-chloro-1H-indole-2-propanoic acid By following a procedure analogous to Example 2 starting from the compound obtained according to Example 158, the expected product is obtained in the form of a white powder (yield=94%).
M.p.=220-223° C.

Example 160

1-[(1,3-Benzodioxol-5-yl)sulfonyl]-5-chloro-1H-indole-2-propanoic acid methyl ester By following a procedure analogous to Preparation 6 starting from the compound obtained according to Preparation 100, the expected product is obtained in the form of a beige powder (yield=90%).
M.p.=122-129° C.

Example 161

1-[(1,3-Benzodioxol-5-yl)sulfonyl]-5-chloro-1H-indole-2-propanoic acid

By following a procedure analogous to Example 2 starting from the compound obtained according to Example 160, the expected product is obtained in the form of a white powder (yield=98%).
M.p.=207° C.

Example 162

1-[(1,3-Benzodioxol-5-yl)sulfonyl]-5-chloro-1H-indole-2-butanoic acid methyl ester By following a procedure analogous to Preparation 6 starting from the compound obtained according to Preparation 101, the expected product is obtained in the form of a beige powder (yield=97%).
M.p.=98-103° C.

Example 163

1-[(1,3-Benzodioxol-5-yl)sulfonyl]-5-chloro-1H-indole-2-butanoic acid

By following a procedure analogous to Example 2 starting from the compound obtained according to Example 162, the expected product is obtained in the form of a white powder (yield=96%).
M.p.=154-156° C.

Example 164

5-Chloro-1-[[4-(4-morpholinylsulfonyl)phenyl]sulfonyl]-1H-indole-2-butanoic acid methyl ester By following a procedure analogous to Preparation 6 starting from the compound obtained according to Preparation 102, the expected product is obtained in the form of a yellow powder (yield=94%).
M.p.=54° C.

Example 165

5-Chloro-1-[[4-(4-morpholinylsulfonyl)phenyl]sulfonyl]-1H-indole-2-butanoic acid By following a procedure analogous to Example 2 starting from the compound obtained according to Example 164, the expected product is obtained in the form of a white powder (yield=93%).
M.p.=181° C.

Example 166

5-Chloro-1-[(2-pyridinyl)sulfonyl]-1H-indole-2-propanoic acid methyl ester

By following a procedure analogous to Example 152 starting from the methyl ester of 4-pentynoic acid, the expected product is obtained in the form of an orange solid (yield=72%).
M.p.=121° C.

Example 167

5-Chloro-1-[(2-pyridinyl)sulfonyl]-1H-indole-2-propanoic acid

By following a procedure analogous to Example 2 starting from the compound obtained according to Example 166, the expected product is obtained in the form of a white powder (yield=90%).
M.p.=189° C.

Example 168

1-[(6-Benzothiazolyl)sulfonyl]-5-(trifluoromethyl)-1H-indole-2-butanoic acid methyl ester By following a procedure analogous to Preparation 6 starting from the compound obtained according to Preparation 118, the expected product is obtained in the form of a yellow powder (yield=49%).
M.p.=117-121° C.

Example 169

1-[(6-Benzothiazolyl)sulfonyl]-5-(trifluoromethyl)-1H-indole-2-butanoic acid

By following a procedure analogous to Example 2 starting from the compound obtained according to Example 168, the expected product is obtained in the form of a beige powder (yield=97%).
M.p.=175-181° C.

Example 170

1-[(6-Benzothiazolyl)sulfonyl]-5-(trifluoromethyl)-1H-indole-2-propanoic acid methyl ester By following a procedure analogous to Preparation 6 starting from the compound obtained according to Preparation 104, the expected product is obtained in the form of a yellow powder (yield=64%).
M.p.=130-132° C.

Example 171

1-[(6-Benzothiazolyl)sulfonyl]-5-(trifluoromethyl)-1H-indole-2-propanoic acid

By following a procedure analogous to Example 2 starting from the compound obtained according to Example 170, the expected product is obtained in the form of a yellow powder (yield=97%).

Example 172

1-[(2-methyl-6-benzoxazolyl)sulfonyl]-5-(trifluoromethyl)-1H-indole-2-butanoic acid methyl ester By following a procedure analogous to Preparation 6 starting from the compound obtained according to Preparation 105, the expected product is obtained in the form of a beige powder (yield=90%).
M.p.=78-82° C.

Example 173

1-[(2-Methyl-6-benzoxazolyl)sulfonyl]-5-(trifluoromethyl)-1H-indole-2-butanoic acid By following a procedure analogous to Example 2 starting from the compound obtained according to Example 172, the expected product is obtained in the form of a beige powder (yield=31%).
M.p.=214-220° C.

Example 174

1-[(1-Acetyl-2,3-dihydro-1H-indol-5-yl)sulfonyl]-5-(trifluoromethyl)-1H-indole-2-butanoic acid methyl ester By following a procedure analogous to Preparation 6 starting from the compound obtained according to Preparation 106, the expected product is obtained in the form of a beige powder (yield=70%).
M.p.=135-139° C.

Example 175

1-[(1-Acetyl-2,3-dihydro-1H-indol-5-yl)sulfonyl]-5-(trifluoromethyl)-1H-indole-2-butanoic acid By following a procedure analogous to Example 2 starting from the compound obtained according to Example 174, the expected product is obtained in the form of a white solid (yield=45%).
M.p.=183° C.

Example 176

1-[(2,3-dihydro-5-benzofuranyl)sulfonyl]-5-(trifluoromethyl)-1H-indole-2-butanoic acid methyl ester By following a procedure analogous to Preparation 6 starting from the compound obtained according to Preparation 107, the expected product is obtained in the form of a colorless paste (yield=47%).
$^1$H NMR (DMSOd$_6$, 300 MHz) δ=1.95-2.03 (m, 2H), 2.45 (t, 2H), 3.06 (t, 2H), 3.16 (t, 2H), 3.59 (s, 3H), 4.60 (t, 2H), 6.74 (s, 1H), 6.90 (d, 1H), 7.60 (dd, 1H), 7.66 (dd, 1H), 7.75 (s, 1H), 7.92 (s, 1H), 8.23 (d, 1H).

Example 177

1-[(2,3-Dihydro-5-benzofuranyl)sulfonyl]-5-(trifluoromethyl)-1H-indole-2-butanoic acid By following a procedure analogous to Example 2 starting from the compound obtained according to Example 176, the expected product is obtained in the form of a white solid (yield=98%).
M.p.=144-149° C.

Example 178

1-[(2-Methyl-5-benzothiazolyl)sulfonyl]-5-(trifluoromethyl)-1H-indole-2-butanoic acid methyl ester By following a procedure analogous to Preparation 6 starting from the compound obtained according to Preparation 108, the expected product is obtained in the form of a brown paste (yield=70%).
$^1$H NMR (DMSOd$_6$, 300 MHz) δ=1.99 (t, 2H), 2.46 (t, 2H), 2.81 (s, 3H), 3.11 (t, 2H), 3.58 (s, 3H), 6.77 (s, 1H), 7.63 (dd, 1H), 7.80 (dd, 1H), 7.92 (s, 1H), 8.27 (d, 1H), 8.31 (d, 1H), 8.34 (s, 1H).

Example 179

1-[(2-Methyl-5-benzothiazolyl)sulfonyl]-5-(trifluoromethyl)-1H-indole-2-butanoic acid By following a procedure analogous to Example 2 starting from the compound obtained according to Example 178, the expected product is obtained in the form of a beige powder (yield=98%).
M.p.=171-178° C.

Example 180

1-[(2-amino-6-benzothiazolyl)sulfonyl]-5-(trifluoromethyl)-1H-indole-2-propanoic acid methyl ester By following a procedure analogous to Preparation 6 starting from the compound obtained according to Preparation 109, the expected product is obtained in the form of a yellow powder (yield=62%).
M.p.=135-136° C.

Example 181

1-[(2-Amino-6-benzothiazolyl)sulfonyl]-5-(trifluoromethyl)-1H-indole-2-propanoic acid By following a procedure analogous to Example 2 starting from the compound obtained according to Example 180, the expected product is obtained in the form of a white powder (yield=19%).
M.p.>250° C.

Example 182

1-[(2-Methyl-6-benzothiazolyl)sulfonyl]-5-(trifluoromethyl)-1H-indole-2-propanoic acid methyl ester By following a procedure analogous to Preparation 6 starting from the compound obtained according to Preparation 110, the expected product is obtained in the form of a white powder (yield=44%).
M.p.=214-215° C.

Example 183

1-[(2-Methyl-6-benzothiazolyl)sulfonyl]-5-(trifluoromethyl)-1H-indole-2-propanoic acid By following a procedure analogous to Example 2 starting from the compound obtained according to Example 182, the expected product is obtained in the form of a pale yellow powder (yield=62%).
M.p.=186-187° C.

Example 184

1-[(2-Methyl-5-benzothiazolyl)sulfonyl]-5-(trifluoromethyl)-1H-indole-2-propanoic acid methyl ester By following a procedure analogous to Preparation 6 starting from the compound obtained according to Preparation 111, the expected product is obtained in the form of a beige powder (yield=53%).
$^1$H NMR (DMSOd$_6$, 300 MHz) δ=2.81 (s, 3H), 2.85 (d, 2H), 3.32 (d, 2H), 3.61 (s, 3H), 6.74 (s, 1H), 7.63 (dd, 1H), 7.81 (dd, 1H), 7.93 (s, 1H), 8.27-8.31 (m, 2H), 8.35 (d, 1H).

Example 185

1-[(2-Methyl-5-benzothiazolyl)sulfonyl]-5-(trifluoromethyl)-1H-indole-2-propanoic acid By following a procedure analogous to Example 2 starting from the compound obtained according to Example 184, the expected product is obtained in the form of a white powder (yield=80%).
M.p.=235-236° C.

Example 186

1-[(2-Methyl-6-benzoxazolyl)sulfonyl]-5-(trifluoromethyl)-1H-indole-2-propanoic acid methyl ester By following a procedure analogous to Preparation 6 starting from the compound obtained according to Preparation 112, the expected product is obtained in the form of a yellow oil (yield=56%).
$^1$H NMR (DMSOd$_6$, 300 MHz) δ=2.63 (s, 3H), 2.84 (d, 2H), 3.33 (d, 2H), 353 (s, 3H), 6.73 (s, 1H), 7.61 (dd, 1H), 7.78-7.93 (m, 3H), 8.29 (d, 1H), 8.35 (s, 1H).

Example 187

1-[(2-Methyl-7-benzothiazolyl)sulfonyl]-5-(trifluoromethyl)-1H-indole-2-propanoic acid methyl ester By following a procedure analogous to Preparation 6 starting from the compound obtained according to Preparation 113, the expected product is obtained in the form of a yellow powder (yield=83%).
M.p.=106-108° C.

Example 188

1-[(1-Acetyl-2,3-dihydro-1H-indol-5-yl)sulfonyl]-5-(trifluoromethyl)-1H-indole-2-propanoic acid methyl ester By following a procedure analogous to Preparation 6 starting from the compound obtained according to Preparation 114, the expected product is obtained in the form of an oil (yield=66%).
$^1$H NMR (DMSOd$_6$, 300 MHz) δ=2.1 (s, 3H), 2.8 (t, 2H), 3.1 (t, 2H), 3.3 (t, 2H), 3.61 (s, 3H), 4.1 (t, 2H), 6.7 (s, 1H), 7.6 (dd, 1H), 7.7 (s, 1H), 7.7 (dd, 1H), 7.9 (d, 1H), 8.2 (d, 1H).

Example 189

1-[(1-Acetyl-2,3-dihydro-1H-indol-5-yl)sulfonyl]-5-(trifluoromethyl)-1H-indole-2-propanoic acid By following a procedure analogous to Example 2 starting from the compound obtained according to Example 188, the expected product is obtained in the form of a white powder (yield=40%).
M.p.=205-207° C.

Example 190

1-[(2,3-Dihydro-5-benzofuranyl)sulfonyl]-5-(trifluoromethyl)-1H-indole-2-propanoic acid methyl ester By following a procedure analogous to Preparation 6 starting from the compound obtained according to Preparation 115, the expected product is obtained in the form of a colorless paste (yield=79%).
$^1$H NMR (DMSOd$_6$, 300 MHz) δ=2.83 (t, 2H), 3.19 (t, 2H), 3.32 (t, 2H), 3.62 (s, 3H), 4.61 (t, 2H), 6.71 (d, 1H), 6.90 (d, 1H), 7.60 (dd, 1H), 7.68 (dd, 1H), 7.76 (d, 1H), 7.93 (d, 1H), 8.23 (dd, 1H).

Example 191

1-[(2,3-Dihydro-5-benzofuranyl)sulfonyl]-5-(trifluoromethyl)-1H-indole-2-propanoic acid By following a procedure analogous to Example 2 starting from the compound obtained according to Example 190, the expected product is obtained in the form of a beige powder (yield=34%).
M.p.=161-164° C.

Example 192

1-[[4-(4-Morpholinylsulfonyl)phenyl]sulfonyl]-5-(trifluoromethyl)-1H-indole-2-propanoic acid methyl ester By following a procedure analogous to Preparation 6 starting from the compound obtained according to Preparation 116, the expected product is obtained in the form of a white solid (yield=78%).
M.p.=186-187° C.

Example 193

1-[[4-(4-Morpholinylsulfonyl)phenyl]sulfonyl]-5-(trifluoromethyl)-1H-indole-2-propanoic acid By following a procedure analogous to Example 2 starting from the compound obtained according to Example 192, the expected product is obtained in the form of a white powder (yield=36%).
M.p.=238-239° C.

Example 194

1-[(2-Amino-6-benzothiazolyl)sulfonyl]-5-chloro-1H-indole-2-butanoic acid methyl ester By following a procedure analogous to Preparation 6 starting from the compound obtained according to Preparation 90, the expected product is obtained in the form of a yellow solid (yield=44%).
M.p.=235-239° C.

Example 195

1-[(2-Amino-6-benzothiazolyl)sulfonyl]-5-chloro-1H-indole-2-butanoic acid

By following a procedure analogous to Example 2 starting from the compound obtained according to Example 194, the expected product is obtained in the form of a beige powder (yield=49%).
M.p.=155-162° C.

Example 196

1-[(2,3-Dihydro-1H-indol-5-yl)sulfonyl]-5-(trifluoromethyl)-1H-indole-2-butanoic acid By following a procedure analogous to Example 2 (except that 4 equivalents of lithium hydroxide are used) starting from the compound obtained according to Example 174, the expected product is obtained in the form of a beige solid (yield=36%).
M.p.=175° C.

Example 197

1-[[2-(Acetylamino)-6-benzothiazolyl]sulfonyl]-5-(trifluoromethyl)-1H-indole-2-butanoic acid methyl ester By following a procedure analogous to Example 3 starting from the compound obtained according to Preparation 119 and 2-(acetylamino)-6-benzothiazolesulfonyl chloride, the expected product is obtained in the form of a yellow solid (yield=14%).
M.p.=215° C.

Example 198

1-[[2-(Acetylamino)-6-benzothiazolyl]sulfonyl]-5-(trifluoromethyl)-1H-indole-2-butanoic acid By following a procedure analogous to Example 2 starting from the compound obtained according to Example 197, the expected product is obtained in the form of a white powder (yield=57%).
M.p.>250° C.

Example 199

1-[(2-Methyl-6-benzothiazolyl)sulfonyl]-5-(trifluoromethyl)-1H-indole-2-butanoic acid methyl ester By following a procedure analogous to Example 197 starting from 2-methyl-6-benzothiazolesulfonyl chloride, the expected product is obtained in the form of a beige solid (yield=12%).
M.p.=163-168° C.

Example 200

1-[(2-Methyl-6-benzothiazolyl)sulfonyl]-5-(trifluoromethyl)-1H-indole-2-butanoic acid By following a procedure analogous to Example 2 starting from the compound obtained according to Example 199, the expected product is obtained in the form of a beige solid (yield=87%).
M.p.=184-187° C.

Example 201

2-[[5-Chloro-1-(phenylsulfonyl)-1H-indol-2-yl]methoxy]propanoic acid ethyl ester A mixture of 600 mg (1.52 mM) of N-(4-chloro-2-iodophenyl)benzenesulfonamide (Preparation 120) and 0.5 ml of dimethylformamide is prepared in a microwave reaction tube and 14 mg (0.076 mM) of cuprous iodide, 27 mg (0.038 mM) of bis(triphenylphosphine)dichloropalladium, 357 mg (2.3 mM) of the ethyl ester of 2-(2-propynyloxy)propanoic acid and, finally, 0.5 ml of diethylamine are added. The mixture is heated by microwaves at 130° C. for 15 min and then cooled and hydrolyzed with 10 ml of water. The mixture is extracted three times with 15 ml of ethyl acetate and the combined organic phases are washed with water and then dried over magnesium sulfate and concentrated under reduced pressure. The residue is purified by chromatography on silica gel using a cyclohexane/ethyl acetate mixture (95/5; v/v) as the eluent to give 0.44 g of the expected compound in the form of a yellow oil (yield=69%).

¹H NMR (DMSOd₆, 300 MHz) δ=1.17 (t, 3H), 1.32 (d, 3H), 4.13 (q, 2H), 4.22 (q, 1H), 4.87 (d, 1H), 4.99 (d, 1H), 6.85 (s, 1H), 7.36 (dd, 1H), 7.58 (t, 2H), 7.68 (d, 1H), 7.70 (t, 1H), 7.96 (d, 2H), 7.99 (d, 1H).

Example 202

2-[[5-Chloro-1-(phenylsulfonyl)-1H-indol-2-yl]methoxy]propanoic acid

By following a procedure analogous to Example 2 starting from the compound obtained according to Example 201, the expected product is obtained in the form of a pasty white solid (yield=85%).
¹H NMR (DMSOd₆, 300 MHz) δ=1.31 (d, 3H), 4.14 (q, 1H), 4.84 (d, 1H), 5.02 (d, 1H), 6.85 (d, 1H), 7.35 (dd, 1H), 7.57 (t, 2H), 7.67 (d, 1H), 7.70 (tt, 1H), 7.96 (dt, 2H), 7.99 (d, 1H), 12.80 (broad m, 1H).

Example 203

[[5-Chloro-1-(phenylsulfonyl)-1H-indol-2-yl]methoxy]acetic acid methyl ester

By following a procedure analogous to Example 201 starting from the methyl ester of (2-propynyloxy)acetic acid, the expected compound is obtained in the form of a pale yellow solid (yield=71%).
M.p.=98-100° C.

Example 204

[[5-Chloro-1-(phenylsulfonyl)-1H-indol-2-yl]methoxy]acetic acid

By following a procedure analogous to Example 2 starting from the compound obtained according to Example 203, the expected product is obtained in the form of a white solid (yield=98%).
M.p.=140-142° C.

Example 205

2-[[5-chloro-1-(phenylsulfonyl)-1H-indol-2-yl]methoxy]-2-methylpropanoic acid ethyl ester By following a procedure analogous to Example 201 starting from the methyl ester of 2-methyl-2-(2-propynyloxy)propanoic acid, the expected compound is obtained in the form of a yellow oil (yield=59%).
¹H NMR (DMSOd₆, 300 MHz) δ=1.45 (s, 6H), 3.66 (s, 3H), 4.83 (s, 2H), 6.82 (s, 1H), 7.35 (dd, 1H), 7.61 (t, 2H), 7.68 (m, 2H), 7.96 (dt, 2H), 8.01 (d, 1H).

Example 206

2-[[5-Chloro-1-(phenylsulfonyl)-1H-indol-2-yl]methoxy]-2-methylpropanoic acid

By following a procedure analogous to Example 2 starting from the compound obtained according to Example 205, the expected product is obtained in the form of a pasty white solid (yield=83%).
¹H NMR (DMSOd₆, 300 MHz) δ=1.43 (s, 6H), 4.86 (s, 2H), 6.81 (s, 1H), 7.33 (dd, 1H), 7.58 (t, 2H), 7.67 (m, 2H), 7.94 (dt, 2H), 7.99 (d, 1H), 12.80 (broad m, 1H).

Example 207

[[1-(Phenylsulfonyl)-5-(trifluoromethyl)-1H-indol-2-yl]methoxy]acetic acid methyl ester By following a procedure analogous to Example 203 starting from the sulfonamide obtained according to Preparation 121, the expected compound is obtained in the form of a yellow solid (yield=50%).
M.p.=90-92° C.

Example 208

[[1-(Phenylsulfonyl)-5-(trifluoromethyl)-1H-indol-2-yl]methoxy]acetic acid

By following a procedure analogous to Example 2 starting from the compound obtained according to Example 207, the expected product is obtained in the form of a yellow solid (yield=85%).
M.p.=158-160° C.

Example 209

2-[[1-(Phenylsulfonyl)-5-(trifluoromethyl)-1H-indol-2-yl]methoxy]propanoic acid ethyl ester By following a procedure analogous to Example 201 starting from the sulfonamide obtained according to Preparation 121, the expected compound is obtained in the form of a yellow oil (yield=74%).
¹H NMR (DMSOd₆, 300 MHz) δ=1.19 (t, 3H), 1.32 (d, 3H), 4.13 (q, 2H), 4.24 (d, 1H), 4.91 (d, 1H), 5.03 (d, 1H), 7.01 (s, 1H), 7.60 (t, 2H), 7.69 (dd, 1H), 7.72 (t, 1H), 8.01 (dt, 2H), 8.21 (d, 1H).

Example 210

2-[[1-(Phenylsulfonyl)-5-(trifluoromethyl)-1H-indol-2-yl]methoxy]propanoic acid

By following a procedure analogous to Example 2 starting from the compound obtained according to Example 209, the expected product is obtained in the form of a white solid (yield=50%).
M.p.=72-74° C.

Example 211

2-Methyl-2-[[1-(phenylsulfonyl)-5-(trifluoromethyl)-1H-indol-2-yl]methoxy]propanoic acid ethyl ester By following a procedure analogous to Example 205 starting from the sulfonamide obtained according to Preparation 121, the expected compound is obtained in the form of a beige solid (yield=46%).
M.p.=62-64° C.

Example 212

2-Methyl-2-[[1-(phenylsulfonyl)-5-(trifluoromethyl)-1H-indol-2-yl]methoxy]propanoic acid By following a procedure analogous to Example 2 starting from the compound obtained according to Example 211, the expected product is obtained in the form of a white solid (yield=50%).
M.p.=134-136° C.

Example 213

[2-[5-Chloro-1-(phenylsulfonyl)-1H-indol-2-yl]ethoxy]acetic acid ethyl ester

By following a procedure analogous to Example 201 starting from the ethyl ester of (3-butynyloxy)acetic acid, the expected compound is obtained in the form of an orange solid (yield=79%).
M.p.=60-62° C.

Example 214

[2-[5-Chloro-1-(phenylsulfonyl)-1H-indol-2-yl]ethoxy]acetic acid

By following a procedure analogous to Example 2 starting from the compound obtained according to Example 213, the expected product is obtained in the form of a white solid (yield=97%).
M.p.=135-137° C.

Example 215

2-Methyl-2-[[1-[(6-benzothiazolyl)sulfonyl]-5-chloro-1H-indol-2-yl]methoxy]propanoic acid methyl ester A mixture of 126 mg (0.26 mM) of the ester obtained according to Preparation 123 and 1 ml of 1,2-dichloroethane is prepared in a microwave reaction tube and 48 mg (0.26 mM) of copper (cupric) acetate are added. The mixture is heated by microwaves at 150° C. for 15 minutes and then cooled, diluted with 6 ml of dichloromethane and filtered on Whatman paper. The filtrate is concentrated under reduced pressure and the crude product is purified by chromatography on silica gel using a dichloromethane/ethyl acetate mixture (97/3; v/v) as the eluent to give 79 mg of the expected compound in the form of a pasty yellow solid (yield=63%).
$^1$H NMR (DMSOd$_6$, 300 MHz) δ=1.46 (s, 6H), 3.65 (s, 3H), 4.88 (s, 2H), 6.83 (s, 1H), 7.35 (dd, 1H), 7.66 (d, 1H), 8.02 (dd, 1H), 8.07 (d, 1H), 8.23 (d, 1H), 9.07 (d, 1H), 9.66 (s, 1H).

Example 216

2-Methyl-2-[[1-[(6-benzothiazolyl)sulfonyl]-5-chloro-1H-indol-2-yl]methoxy]propanoic acid By following a procedure analogous to Example 2 starting from the compound obtained according to Example 215, the expected product is obtained in the form of a white solid (yield=94%).
M.p.=74° C.

Example 217

2-Methyl-2-[[1-[(6-benzothiazolyl)sulfonyl]-5-(trifluoromethyl)-1H-indol-2-yl]-methoxy]propanoic acid methyl ester By following a procedure analogous to Example 215 starting from the compound obtained according to Preparation 125, the expected product is obtained in the form of a yellow oil (yield=72%).
$^1$H NMR (DMSOd$_6$, 250 MHz) δ=1.46 (s, 6H), 3.65 (s, 3H), 4.92 (s, 2H), 6.98 (s, 1H), 7.65 (dd, 1H), 8.02 (s, 1H), 8.07 (dd, 1H), 8.26 (t, 2H), 9.12 (d, 1H), 9.66 (s, 1H).

Example 218

2-Methyl-2-[[1-[(6-benzothiazolyl)sulfonyl]-5-(trifluoromethyl)-1H-indol-2-yl]-methoxy]propanoic acid By following a procedure analogous to Example 2 starting from the compound obtained according to Example 217, the expected product is obtained in the form of a white solid (yield=98%).
M.p.=98-100° C.

Example 219

2-Methyl-2-[[1-[(2-methyl-6-benzothiazolyl)sulfonyl]-5-chloro-1H-indol-2-yl]-methoxy]propanoic acid methyl ester By following a procedure analogous to Example 215 starting from the compound obtained according to Preparation 126, the expected product is obtained in the form of a white paste (yield=73%).
$^1$H NMR (DMSOd$_6$, 250 MHz) δ=1.46 (s, 6H), 2.83 (s, 3H), 3.66 (s, 3H), 4.87 (s, 2H), 6.82 (s, 1H), 7.35 (dd, 1H), 7.66 (d, 1H), 7.96 (dd, 1H), 8.03 (d, 1H), 8.06 (d, 1H), 8.92 (d, 1H).

Example 220

2-Methyl-2-[1-[[(2-methyl-6-benzothiazolyl)sulfonyl]-5-chloro-1H-indol-2-yl]-methoxy]propanoic acid By following a procedure analogous to Example 2 starting from the compound obtained according to Example 219, the expected product is obtained in the form of a white solid (yield=86%).
M.p.=172-174° C.

Example 221

2-Methyl-2-[[1-[(2-methyl-5-benzothiazolyl)sulfonyl]-5-chloro-1H-indol-2-yl]-methoxy]propanoic acid methyl ester By following a procedure analogous to Example 215 starting from the compound obtained according to Preparation 127, the expected product is obtained in the form of a white solid (yield=71%).
M.p.=132-134° C.

Example 222

2-Methyl-2-[[1-[(2-methyl-5-benzothiazolyl)sulfonyl]-5-chloro-1H-indol-2-yl]-methoxy]propanoic acid By following a procedure analogous to Example 2 starting from the compound obtained according to Example 221, the expected product is obtained in the form of a white solid (yield=86%).
M.p.=134-136° C.

Example 223

2-[[1-[(6-Benzothiazolyl)sulfonyl]-5-chloro-1H-indol-2-yl]methoxy]propanoic acid ethyl ester By following a procedure analogous to Example 215 starting from the compound obtained according to Preparation 129, the expected product is obtained in the form of yellow oil (yield=89%).

$^1$H NMR (DMSOd$_6$, 250 MHz) δ=1.17 (t, 3H), 1.32 (d, 3H), 4.11 (q, 2H), 4.22 (q, 1H), 4.92 (d, 1H), 5.03 (d, 1H), 6.86 (s, 1H), 7.36 (dd, 1H), 7.67 (d, 1H), 8.04 (dd, 1H), 8.08 (d, 1H), 8.21 (d, 1H), 9.08 (d, 1H), 9.66 (s, 1H).

Example 224

2-[[1-[(6-Benzothiazolyl)sulfonyl]-5-chloro-1H-indol-2-yl]methoxy]propanoic acid By following a procedure analogous to Example 2 starting from the compound obtained according to Example 223, the expected product is obtained in the form of a white solid (yield=98%).

M.p.=102-104° C.

Example 225

1-[(1,3-Benzodioxol-5-yl)sulfonyl]-5-(trifluoromethyl)-1H-indole-2-butanoic acid methyl ester By following a procedure analogous to Preparation 6 starting from the compound obtained according to Preparation 130, the expected product is obtained in the form of a beige paste (yield=43%).

$^1$H NMR (DMSOd$_6$, 250 MHz) δ=1.95-2.03 (m, 2H), 2.4 (t, 2H), 3.06 (t, 2H), 3.59 (s, 3H), 6.14 (s, 2H), 6.75 (s, 1H), 7.05 (d, 1H), 7.33 (s, 1H), 7.48 (dd, 1H), 7.59 (dd, 1H), 7.93 (s, 1H), 8.23 (d, 1H).

Example 226

1-[(1,3-Benzodioxol-5-yl)sulfonyl]-5-(trifluoromethyl)-1H-indole-2-butanoic acid By following a procedure analogous to Example 2 starting from the compound obtained according to Example 225, the expected product is obtained in the form of a pink powder (yield=59%).

M.p.=171-175° C.

Example 227

1-[[2-(Acetylamino)-6-benzothiazolyl]sulfonyl]-5-(trifluoromethyl)-1H-indole-2-propanoic acid methyl ester By following a procedure analogous to Preparation 6 starting from the compound obtained according to Preparation 131, the expected product is obtained in the form of a yellow powder (yield=20%).

$^1$H NMR (DMSOd$_6$, 500 MHz) δ=2.24 (s, 3H), 2.87 (t, 2H), 3.40 (t, 2H), 3.64 (s, 3H), 6.75 (s, 1H), 7.64 (d, 1H), 7.85 (s, 2H), 7.95 (s, 1H), 8.29 (d, 1H), 8.80 (s, 1H), 12.68 (s, 1H).

Example 228

1-[[2-(Acetylamino)-6-benzothiazolyl]sulfonyl]-5-(trifluoromethyl)-1H-indole-2-propanoic acid By following a procedure analogous to Example 2 starting from the compound obtained according to Example 227, the expected product is obtained in the form of a yellow powder (yield=73%).

M.p.>290-292° C.

Example 229

2-Methyl-2-[[1-[(2-methyl-5-benzothiazolyl)sulfonyl]-5-(trifluoromethyl)-1H-indol-2-yl]methoxy]propanoic acid methyl ester By following a procedure analogous to Example 215 starting from the compound obtained according to Preparation 132, the expected product is obtained in the form of a white solid (yield=57%).

M.p.=164-166° C.

Example 230

2-Methyl-2-[[1-[(2-methyl-5-benzothiazolyl)sulfonyl]-5-(trifluoromethyl)-1H-indol-2-yl]methoxy]propanoic acid By following a procedure analogous to Example 2 starting from the compound obtained according to Example 229, the expected product is obtained in the form of a white solid (yield=97%).

M.p.=188-190° C.

Example 231

2-[[1-(1,3-Benzodioxol-5-ylsulfonyl)-5-(trifluoromethyl)-1H-indol-2-yl]methoxy]-2-methylpropanoic acid methyl ester By following a procedure analogous to Example 215 starting from the compound obtained according to Preparation 133, the expected product is obtained in the form of a colorless oil (yield=71%).

$^1$H NMR (DMSOd$_6$, 250 MHz) δ=8.19 (d, 1H), 8.02 (d, 1H), 7.64 (m, 2H), 7.57 (d, 1H), 7.08 (d, 1H), 6.97 (d, 1H), 6.14 (s, 2H), 4.85 (s, 2H), 3.68 (s, 3H), 1.49 (s, 6H).

Example 232

2-[[1-(1,3-Benzodioxol-5-ylsulfonyl)-5-(trifluoromethyl)-1H-indol-2-yl]methoxy]-2-methylpropanoic acid By following a procedure analogous to Example 2 starting from the compound obtained according to Example 231, the expected product is obtained in the form of a white solid (yield=94%).

M.p.=130-132° C.

Example 233

2-[[1-[[2-(Acetylamino)-6-benzothiazolyl]sulfonyl]-5-(trifluoromethyl)-1H-indol-2-yl]methoxy]-2-methylpropanoic acid methyl ester By following a procedure analogous to Example 215 starting from the compound obtained according to Preparation 134, the expected product is obtained in the form of a white solid (yield=52%).
M.p.=212-214° C.

Example 234

2-[[1-[[2-(Acetylamino)-6-benzothiazolyl]sulfonyl]-5-(trifluoromethyl)-1H-indol-2-yl]methoxy]-2-methylpropanoic acid By following a procedure analogous to Example 2 starting from the compound obtained according to Example 233, the expected product is obtained in the form of a beige solid (yield=86%).
M.p.=144-146° C.

Example 235

2-[[1-[(2,3-Dihydro-5-benzofuranyl)sulfonyl]-5-(trifluoromethyl)-1H-indol-2-yl]methoxy]-2-methylpropanoic acid methyl ester By following a procedure analogous to Example 215 starting from the compound obtained according to Preparation 135, the expected product is obtained in the form of a colorless oil (yield=75%).
$^1$H NMR (DMSOd$_6$, 250 MHz) δ=8.19 (d, 1H), 8.02 (s, 1H), 7.92 (d, 1H), 7.83 (dd, 1H), 7.63 (dd, 1H), 6.94 (s, 1H), 6.91 (d, 1H), 4.87 (s, 2H), 4.61 (t, 2H), 3.68 (s, 3H), 3.19 (t, 2H), 1.48 (s, 6H).

Example 236

2-[[1-[(2,3-Dihydro-5-benzofuranyl)sulfonyl]-5-(trifluoromethyl)-1H-indol-2-yl]methoxy]-2-methylpropanoic acid By following a procedure analogous to Example 2 starting from the compound obtained according to Example 235, the expected product is obtained in the form of a white solid (yield=99%).
M.p.=92-94° C.

Example 237

2-Methyl-2-[[1-[(2-methyl-7-benzothiazolyl)sulfonyl]-5-(trifluoromethyl)-1H-indol-2-yl]methoxy] propanoic acid methyl ester By following a procedure analogous to Example 215 starting from the compound obtained according to Preparation 136, the expected product is obtained in the form of a beige solid (yield=75%).
M.p.=118-120° C.

Example 238

2-Methyl-2-[[1-[(2-methyl-7-benzothiazolyl)sulfonyl]-5-(trifluoromethyl)-1H-indol-2-yl]methoxy] propanoic acid By following a procedure analogous to Example 2 starting from the compound obtained according to Example 237, the expected product is obtained in the form of a white solid (yield=91%).
M.p.=98-100° C.

Example 239

2-[[1-[(2,3-Dihydro-1,4-benzodioxin-6-yl)sulfonyl]-5-(trifluoromethyl)-1H-indol-2-yl]methoxy]-2-methylpropanoic acid methyl ester By following a procedure analogous to Example 215 starting from the compound obtained according to Preparation 137, the expected product is obtained in the form of a white solid (yield=81%).
M.p.=128-130° C.

Example 240

2-[[1-[(2,3-Dihydro-1,4-benzodioxin-6-yl)sulfonyl]-5-(trifluoromethyl)-1H-indol-2-yl]methoxy]-2-methylpropanoic acid By following a procedure analogous to Example 2 starting from the compound obtained according to Example 239, the expected product is obtained in the form of a white solid (yield=95%).
M.p.=75° C.

Example 241

2-[[1-[(3,4-Dihydro-4-methyl-2H-1,4-benzoxazin-7-yl)sulfonyl]-5-(trifluoromethyl)-1H-indol-2-yl]methoxy]-2-methylpropanoic acid methyl ester By following a procedure analogous to Example 215 starting from the compound obtained according to Preparation 138, the expected product is obtained in the form of a white solid (yield=85%).
M.p.=96-98° C.

Example 242

2-[[1-[(3,4-Dihydro-4-methyl-2H-1,4-benzoxazin-7-yl)sulfonyl]-5-(trifluoromethyl)-1H-indol-2-yl]methoxy]-2-methylpropanoic acid By following a procedure analogous to Example 2 starting from the compound obtained according to Example 241, the expected product is obtained in the form of a white solid (yield=99%).
M.p.=148-150° C.

Example 243

2-[[1-[(1-Acetyl-2,3-dihydro-1H-indol-5-yl)sulfonyl]-5-(trifluoromethyl)-1H-indol-2-yl]methoxy]-2-methylpropanoic acid methyl ester By following a procedure analogous to Example 215 starting from the compound obtained according to Preparation 139, the expected product is obtained in the form of a white solid (yield=84%).

M.p.=154-156° C.

Example 244

2-[[1-[(1-Acetyl-2,3-dihydro-1H-indol-5-yl)sulfonyl]-5-(trifluoromethyl)-1H-indol-2-yl]methoxy]-2-methylpropanoic acid By following a procedure analogous to Example 2 starting from the compound obtained according to Example 243, the expected product is obtained in the form of a white solid (yield=61%).

M.p.=176-178° C.

Example 245

2-[[1-[(3,5-Dimethylphenyl)sulfonyl]-5-(trifluoromethyl)-1H-indol-2-yl]methoxy]-2-methylpropanoic acid methyl ester By following a procedure analogous to Example 215 starting from the compound obtained according to Preparation 140, the expected product is obtained in the form of a white solid (yield=86%).

M.p.=132-134° C.

Example 246

2-[[1-[(3,5-Dimethylphenyl)sulfonyl]-5-(trifluoromethyl)-1H-indol-2-yl]methoxy]-2-methylpropanoic acid By following a procedure analogous to Example 2 starting from the compound obtained according to Example 245, the expected product is obtained in the form of a white solid (yield=82%).

M.p.=150-152° C.

Example 247

2-[[1-[(2,5-Dimethoxyphenyl)sulfonyl]-5-(trifluoromethyl)-1H-indol-2-yl]methoxy]-2-methylpropanoic acid methyl ester By following a procedure analogous to Example 215 starting from the compound obtained according to Preparation 141, the expected product is obtained in the form of a white solid (yield=84%).

M.p.=130-132° C.

Example 248

2-[[1-[(2,5-Dimethoxyphenyl)sulfonyl]-5-(trifluoromethyl)-1H-indol-2-yl]methoxy]-2-methylpropanoic acid By following a procedure analogous to Example 2 starting from the compound obtained according to Example 247, the expected product is obtained in the form of a white solid (yield=50%).

M.p.=186-188° C.

Example 249

2-[[1-[[4-(1-Methylethyl)phenyl]sulfonyl]-5-(trifluoromethyl)-1H-indol-2-yl]methoxy]-2-methylpropanoic acid methyl ester By following a procedure analogous to Example 215 starting from the compound obtained according to Preparation 142, the expected product is obtained in the form of a colorless oil (yield=86%).

$^1$H NMR (DMSOd$_6$, 250 MHz) δ=8.23 (d, 1H), 8.02 (d, 1H), 7.91 (dt, 2H), 7.65 (dd, 1H), 7.49 (dt, 2H), 6.96 (d, 1H), 4.86 (s, 2H), 3.68 (s, 3H), 2.92 (hep, 1H), 1.46 (s, 6H), 1.15 (d, 6H).

Example 250

2-[[1-[[4-(1-Methylethyl)phenyl]sulfonyl]-5-(trifluoromethyl)-1H-indol-2-yl]methoxy]-2-methylpropanoic acid By following a procedure analogous to Example 2 starting from the compound obtained according to Example 249, the expected product is obtained in the form of a white solid (yield=74%).

M.p.=132-134° C.

Example 251

2-[[1-(1,3-Benzodioxol-5-ylsulfonyl)-5-chloro-1H-indol-2-yl]methoxy]-2-methylpropanoic acid methyl ester By following a procedure analogous to Example 215 starting from the compound obtained according to Preparation 143, the expected product is obtained in the form of a white solid (yield=83%).

M.p.=90-92° C.

Example 252

2-[[1-(1,3-Benzodioxol-5-ylsulfonyl)-5-chloro-1H-indol-2-yl]methoxy]-2-methylpropanoic acid By following a procedure analogous to Example 2 starting from the compound obtained according to Example 251, the expected product is obtained in the form of a white solid (yield=99%).

M.p.=174-176° C.

Example 253

2-[[1-[[2-(Acetylamino)-6-benzothiazolyl]sulfonyl]-5-chloro-1H-indol-2-yl]methoxy]-2-methylpropanoic acid methyl ester By following a procedure analogous to Example 215 starting from the compound obtained according to Preparation 144, the expected product is obtained in the form of a yellow solid (yield=34%).
M.p.=112-114° C.

Example 254

2-[[1-[[2-(Acetylamino)-6-benzothiazolyl]sulfonyl]-5-chloro-1H-indol-2-yl]methoxy]-2-methylpropanoic acid By following a procedure analogous to Example 2 starting from the compound obtained according to Example 253, the expected product is obtained in the form of a white solid (yield=90%).
M.p.=162-164° C.

Example 255

2-[[1-[(1-Acetyl-2,3-dihydro-1H-indol-5-yl)sulfonyl]-5-chloro-1H-indol-2-yl]methoxy]-2-methylpropanoic acid methyl ester By following a procedure analogous to Example 215 starting from the compound obtained according to Preparation 145, the expected product is obtained in the form of a beige solid (yield=90%).
M.p.=128-130° C.

Example 256

2-[[1-[(1-Acetyl-2,3-dihydro-1H-indol-5-yl)sulfonyl]-5-chloro-1H-indol-2-yl]methoxy]-2-methylpropanoic acid By following a procedure analogous to Example 2 starting from the compound obtained according to Example 255, the expected product is obtained in the form of a white solid (yield=95%).
M.p.=142-144° C.

Example 257

2-[[5-Chloro-1-[(2,3-dihydro-5-benzofuranyl)sulfonyl]-1H-indol-2-yl]methoxy]-2-methylpropanoic acid methyl ester By following a procedure analogous to Example 215 starting from the compound obtained according to Preparation 146, the expected product is obtained in the form of a colorless oil (yield=80%).
$^1$H NMR (DMSOd$_6$, 300 MHz) δ=8.10 (d, 1H), 7.86 (d, 1H), 7.77 (dd, 1H), 7.66 (d, 1H), 7.33 (dd, 1H), 7.89 (d, 1H), 6.79 (s, 1H), 4.83 (s, 2H), 4.60 (t, 2H), 3.67 (s, 3H), 3.18 (t, 2H), 1.47 (s, 6H).

Example 258

2-[[5-Chloro-1-[(2,3-dihydro-5-benzofuranyl)sulfonyl]-1H-indol-2-yl]methoxy]-2-methylpropanoic acid By following a procedure analogous to Example 2 starting from the compound obtained according to Example 257, the expected product is obtained in the form of a white solid (yield=94%).
M.p.=130-132° C.

Example 259

2-Methyl-2-[[5-chloro-1-[(2-methyl-7-benzothiazolyl)sulfonyl]-1H-indol-2-yl]-methoxy]propanoic acid methyl ester By following a procedure analogous to Example 215 starting from the compound obtained according to Preparation 147, the expected product is obtained in the form of a yellow oil (yield=78%).
$^1$H NMR (DMSOd$_6$, 250 MHz) δ=8.24 (dd, 1H), 7.95 (d, 1H), 7.84 (dd, 1H), 7.69 (m, 2H), 7.33 (dd, 1H), 6.87 (d, 1H), 4.81 (s, 2H), 3.62 (s, 3H), 2.85 (s, 3H), 1.34 (s, 6H).

Example 260

2-Methyl-2-[[5-chloro-1-[(2-methyl-7-benzothiazolyl)sulfonyl]-1H-indol-2-yl]-methoxy]propanoic acid By following a procedure analogous to Example 2 starting from the compound obtained according to Example 259, the expected product is obtained in the form of a white solid (yield=94%).
M.p.=128-130° C.

Example 261

2-[[5-Chloro-1-[(2,3-dihydro-1,4-benzodioxin-6-yl)sulfonyl]-1H-indol-2-yl]methoxy]-2-methylpropanoic acid methyl ester By following a procedure analogous to Example 215 starting from the compound obtained according to Preparation 148, the expected product is obtained in the form of a colorless oil (yield 87%).
$^1$H NMR (DMSOd$_6$, 300 MHz) δ=8.02 (d, 1H), 7.88 (d, 2H), 7.67 (d, 1H), 7.46 (d, 2H), 7.36 (dd, 1H), 6.81 (s, 1H), 4.82 (s, 2H), 3.66 (s, 3H), 2.97 (hep, 1H), 1.45 (s, 6H), 1.15 (d, 6H).

Example 262

2-[[5-Chloro-1-[(2,3-dihydro-1,4-benzodioxin-6-yl)sulfonyl]-1H-indol-2-yl]methoxy]-2-methylpropanoic acid By following a procedure analogous to Example 2 starting from the compound obtained according to Example 261, the expected product is obtained in the form of a white solid (yield=88%).
M.p.=156-158° C.

Example 263

2-[[5-Chloro-1-[(3,4-dihydro-4-methyl-2H-1,4-benzoxazin-7-yl)sulfonyl]-1-indol-2-yl]methoxy]-2-methylpropanoic acid methyl ester By following a procedure analogous to Example 215 starting from the compound obtained according to Preparation 149, the expected product is obtained in the form of a white solid (yield=85%).
M.p.=96-98° C.

Example 264

2-[[5-Chloro-1-[(3,4-dihydro-4-methyl-2H-1,4-benzoxazin-7-yl)sulfonyl]-1H-indol-2-yl]methoxy]-2-methylpropanoic acid By following a procedure analogous to Example 2 starting from the compound obtained according to Example 263, the expected product is obtained in the form of a white solid (yield=98%).
M.p.=148-150° C.

Example 265

2-[[5-Chloro-1-[[4-(1-methylethyl)phenyl]sulfonyl]-1H-indol-2-yl]methoxy]-2-methylpropanoic acid methyl ester By following a procedure analogous to Example 215 starting from the compound obtained according to Preparation 150, the expected product is obtained in the form of a colorless oil (yield=94%).
$^1$H NMR (DMSOd$_6$, 300 MHz) δ=8.02 (d, 1H), 7.88 (d, 2H), 7.67 (d, 1H), 7.46 (d, 2H), 7.36 (dd, 1H), 6.81 (s, 1H), 4.82 (s, 2H), 3.66 (s, 3H), 2.97 (hep, 1H), 1.45 (s, 6H), 1.15 (d, 6H).

Example 266

2-[[5-Chloro-1-[[4-(1-methylethyl)phenyl]sulfonyl]-1H-indol-2-yl]methoxy]-2-methylpropanoic acid By following a procedure analogous to Example 2 starting from the compound obtained according to Example 265, the expected product is obtained in the form of a pale yellow solid (yield=95%).
M.p.=60° C.

Example 267

2-[[5-Chloro-1-[(3,5-dimethylphenyl)sulfonyl]-1H-indol-2-yl]methoxy]-2-methylpropanoic acid methyl ester By following a procedure analogous to Example 215 starting from the compound obtained according to Preparation 151, the expected product is obtained in the form of a white solid (yield=94%).
M.p.=110-112° C.

Example 268

2-[[5-Chloro-1-[(3,5-dimethylphenyl)sulfonyl]-1H-indol-2-yl]methoxy]-2-methylpropanoic acid By following a procedure analogous to Example 2 starting from the compound obtained according to Example 267, the expected product is obtained in the form of a white solid (yield=97%).
M.p.=162-164° C.

Example 269

2-[[5-Chloro-1-[(2,5-dimethoxyphenyl)sulfonyl]-1H-indol-2-yl]methoxy]-2-methylpropanoic acid methyl ester By following a procedure analogous to Example 215 starting from the compound obtained according to Preparation 152, the expected product is obtained in the form of a beige solid (yield=70%).
M.p.=132-134° C.

Example 270

2-[[5-Chloro-1-[(2,5-dimethoxyphenyl)sulfonyl]-1H-indol-2-yl]methoxy]-2-methylpropanoic acid By following a procedure analogous to Example 2 starting from the compound obtained according to Example 269, the expected product is obtained in the form of a white solid (yield=96%).
M.p.=156-158° C.

Example 271

2-[[5-Chloro-1-[(4-methoxyphenyl)sulfonyl]-1H-indol-2-yl]methoxy]-2-methylpropanoic acid methyl ester By following a procedure analogous to Example 215 starting from the compound obtained according to Preparation 153, the expected product is obtained in the form of a white solid (yield=92%).
M.p.=96-98° C.

Example 272

2-[[5-Chloro-1-[(4-methoxyphenyl)sulfonyl]-1H-indol-2-yl]methoxy]-2-methylpropanoic acid By following a procedure analogous to Example 2 starting from the compound obtained according to Example 271, the expected product is obtained in the form of a white solid (yield=99%).
M.p.=150-152° C.

Example 273

2-[([5-Chloro-1-[(2-methyl-6-benzothiazolyl)sulfonyl]-1H-indol-2-yl]methoxy]propanoic acid ethyl ester By following a procedure analogous to Example 215 starting from the compound obtained according to Preparation 154, the expected product is obtained in the form of a yellow oil (yield=78%).

¹H NMR (DMSOd₆, 250 MHz) δ=8.93 (s, 1H), 8.00 (m, 3H), 7.66 (d, 1H), 7.35 (dd, 1H), 6.85 (s, 1H), 5.03 (d, 1H), 4.92 (d, 1H), 4.24 (d, 1H), 4.13 (d, 2H), 2.83 (s, 3H), 1.32 (d, 3H), 1.19 (t, 3H).

Example 274

2-[[5-Chloro-1-[(2-methyl-6-benzothiazolyl)sulfonyl]-1H-indol-2-yl]methoxy]propanoic acid By following a procedure analogous to Example 2 starting from the compound obtained according to Example 273, the expected product is obtained in the form of a white solid (yield=95%).
M.p.=106-108° C.

Example 275

2-[[5-Chloro-1-[(2,3-dihydro-1,4-benzodioxin-6-yl)sulfonyl]-1H-indol-2-yl]-methoxy]propanoic acid ethyl ester By following a procedure analogous to Example 215 starting from the compound obtained according to Preparation 155, the expected product is obtained in the form of a yellow oil (yield=86%).
¹H NMR (DMSOd₆, 300 MHz) δ=7.98 (d, 1H), 7.68 (d, 1H), 7.46 (m, 2H), 7.35 (dd, 1H), 7.01 (d, 1H), 6.83 (s, 1H), 4.97 (d, 1H), 4.84 (d, 1H), 4.27 (m, 5H), 4.20 (q, 2H), 1.35 (d, 3H), 1.19 (t, 3H).

Example 276

2-[[5-Chloro-1-[(2,3-dihydro-1,4-benzodioxin-6-yl)sulfonyl]-1H-indol-2-yl]-methoxy]propanoic acid By following a procedure analogous to Example 2 starting from the compound obtained according to Example 275, the expected product is obtained in the form of a yellow solid (yield=97%).
M.p.=70° C.

Example 277

2-[[5-Chloro-1-[(3,4-dihydro-4-methyl-2H-1,4-benzoxazin-7-yl)sulfonyl]-1H-indol-2-yl]methoxy]propanoic acid ethyl ester By following a procedure analogous to Example 215 starting from the compound obtained according to Preparation 156, the expected product is obtained in the form of a colorless oil (yield=85%).
¹H NMR (DMSOd₆, 250 MHz) δ=8.01 (d, 1H), 7.66 (d, 1H), 7.34 (dd, 1H), 7.13 (dd, 1H), 6.99 (d, 1H), 6.78 (m, 2H), 4.98 (d, 1H), 4.85 (d, 1H), 4.23 (m, 3H), 4.18 (q, 2H), 3.24 (m, 2H), 2.80 (s, 3H), 1.34 (d, 3H), 1.19 (t, 3H).

Example 278

2-[[5-Chloro-1-[(3,4-dihydro-4-methyl-2H-1,4-benzoxazin-7-yl)sulfonyl]-1H-indol-2-yl]methoxy]propanoic acid By following a procedure analogous to Example 2 starting from the compound obtained according to Example 277, the expected product is obtained in the form of a white solid (yield=98%).
M.p.=68° C.

Example 279

2-[[5-Chloro-1-[(3,5-dimethyl-4-isoxazolyl)sulfonyl]-1H-indol-2-yl]methoxy]propanoic acid ethyl ester By following a procedure analogous to Example 215 starting from the compound obtained according to Preparation 157, the expected product is obtained in the form of a colorless oil (yield=91%).
¹H NMR (DMSOd₆, 300 MHz) δ=7.84 (d, 1H), 7.78 (d, 1H), 7.40 (dd, 1H), 6.92 (s, 1H), 4.91 (d, 1H), 4.77 (d, 1H), 4.12 (q, 1H), 4.08 (q, 2H), 2.63 (s, 3H), 2.03 (s, 3H), 1.18 (m, 6H).

Example 280

2-[[5-Chloro-1-[(3,5-dimethyl-4-isoxazolyl)sulfonyl]-1H-indol-2-yl]methoxy]propanoic acid By following a procedure analogous to Example 2 starting from the compound obtained according to Example 279, the expected product is obtained in the form of a white solid (yield=92%).
M.p.=110-112° C.

Example 281

2-[[5-Chloro-1-[(2,5-dimethoxyphenyl)sulfonyl]-1H-indol-2-yl]methoxy]propanoic acid ethyl ester By following a procedure analogous to Example 215 starting from the compound obtained according to Preparation 158, the expected product is obtained in the form of a beige solid (yield=88%).
M.p.=118-120° C.

Example 282

2-[[5-Chloro-1-[(2,5-dimethoxyphenyl)sulfonyl]-1H-indol-2-yl]methoxy]propanoic acid By following a procedure analogous to Example 2 starting from the compound obtained according to Example 281, the expected product is obtained in the form of a white solid (yield=99%).
M.p.=196-198° C.

Example 283

2-[[1-[(2-Methyl-6-benzothiazolyl)sulfonyl]-5-(trifluoromethyl)-1H-indol-2-yl]-methoxy]propanoic acid ethyl ester By following a procedure analogous to Example 215 starting from the compound obtained according to Preparation 160, the expected product is obtained in the form of a yellow oil (yield=83%).
¹H NMR (DMSOd₆, 250 MHz) δ=8.98 (m, 1H), 8.26 (d, 1H), 8.04 (m, 3H), 7.65 (dd, 1H), 7.01 (s, 1H), 5.07 (d, 1H), 4.95 (d, 1H), 4.26 (q, 1H), 4.14 (q, 2H), 2.83 (s, 3H), 1.34 (d, 3H), 1.16 (t, 3H).

Example 284

2-[[1-[(2-Methyl-6-benzothiazolyl)sulfonyl]-5-(trifluoromethyl)-1H-indol-2-yl]-methoxy]propanoic acid By following a procedure analogous to Example 2 starting from the compound obtained according to Example 283, the expected product is obtained in the form of a white solid (yield=84%).
M.p.=146-148° C.

Example 285

2-[[1-[(6-Benzothiazolyl)sulfonyl]-5-(trifluoromethyl)-1H-indol-2-yl]methoxy]propanoic acid ethyl ester By following a procedure analogous to Example 215 starting from the compound obtained according to Preparation 161, the expected product is obtained in the form of a yellow oil (yield 76%).
$^1$H NMR (DMSOd$_6$, 250 MHz) δ=9.67 (s, 1H), 9.13 (d, 1H), 8.21 (m, 2H), 8.14 (dd, 1H), 8.11 (m, 1H), 7.68 (dd, 1H), 7.01 (s, 1H), 5.08 (d, 1H), 4.96 (d, 1H), 4.26 (q, 1H), 4.11 (q, 2H), 1.31 (d, 3H), 1.16 (t, 3H).

Example 286

2-[[1-[(6-benzothiazolyl)sulfonyl]-5-(trifluoromethyl)-1H-indol-2-yl]methoxy]propanoic acid By following a procedure analogous to Example 2 starting from the compound obtained according to Example 285, the expected product is obtained in the form of a pasty beige solid (yield=57%).
$^1$H NMR (DMSOd$_6$, 300 MHz) δ=9.67 (s, 1H), 9.15 (d, 1H), 8.24 (m, 2H), 8.11 (dd, 1H), 8.03 (s, 1H), 7.66 (dd, 1H), 7.02 (s, 1H), 5.10 (d, 1H), 4.94 (d, 1H), 4.18 (q, 1H), 1.32 (d, 3H).

Example 287

2-[[1-[(2,3-Dihydro-1,4-benzodioxin-6-yl)sulfonyl]-5-(trifluoromethyl)-1H-indol-2-yl]methoxy]propanoic acid ethyl ester By following a procedure analogous to Example 215 starting from the compound obtained according to Preparation 162, the expected product is obtained in the form of a yellow oil (yield=84%).
$^1$H NMR (DMSOd$_6$, 250 MHz) δ=8.19 (d, 1H), 8.03 (s, 1H), 7.66 (dd, 1H), 7.53 (m, 2H), 7.04 (dd, 1H), 6.98 (s, 1H), 5.01 (d, 1H), 4.88 (d, 1H), 4.27 (m, 5H), 4.21 (q, 2H), 1.36 (d, 3H), 1.19 (t, 3H).

Example 288

2-[[1-[(2,3-Dihydro-1,4-benzodioxin-6-yl)sulfonyl]-5-(trifluoromethyl)-1H-indol-2-yl]methoxy]propanoic acid By following a procedure analogous to Example 2 starting from the compound obtained according to Example 287, the expected product is obtained in the form of a yellow solid (yield=99%).
M.p.=70° C.

Example 289

2-[[1-[(3,4-Dihydro-4-methyl-2H-1,4-benzoxazin-7-yl)sulfonyl]-5-(trifluoromethyl)-1H-indol-2-yl]methoxy]propanoic acid ethyl ester By following a procedure analogous to Example 215 starting from the compound obtained according to Preparation 163, the expected product is obtained in the form of a yellow oil (yield=88%).
$^1$H NMR (DMSOd$_6$, 300 MHz) δ=8.22 (d, 1H), 8.02 (s, 1H), 7.65 (dd, 1H), 7.19 (dd, 1H), 7.04 (d, 1H), 6.96 (s, 1H), 6.78 (d, 1H), 5.03 (d, 1H), 4.89 (d, 1H), 4.24 (m, 3H), 4.14 (q, 2H), 3.24 (m, 2H), 2.80 (s, 3H), 1.36 (d, 3H), 1.19 (t, 3H).

Example 290

2-[[1-[(3,4-Dihydro-4-methyl-2H-1,4-benzoxazin-7-yl)sulfonyl]-5-(trifluoromethyl)-1H-indol-2-yl]methoxy]propanoic acid By following a procedure analogous to Example 2 starting from the compound obtained according to Example 289, the expected product is obtained in the form of a white solid (yield=87%).
M.p.=118-120° C.

Example 291

2-[[1-[(2,5-Dimethoxyphenyl)sulfonyl]-5-(trifluoromethyl)-1H-indol-2-yl]-methoxy]propanoic acid ethyl ester By following a procedure analogous to Example 215 starting from the compound obtained according to Preparation 164, the expected product is obtained in the form of a white solid (yield=89%).
M.p.=130-132° C.

Example 292

2-[[1-[(2,5-Dimethoxyphenyl)sulfonyl]-5-(trifluoromethyl)-1H-indol-2-yl]-methoxy]propanoic acid By following a procedure analogous to Example 2 starting from the compound obtained according to Example 291, the expected product is obtained in the form of a white solid (yield=97%).
M.p.=212-214° C.

Example 293

(2S)-2-[[5-chloro-1-[(6-benzothiazolyl)sulfonyl]-1H-indol-2-yl]methoxy]propanoic acid ethyl ester By following a procedure analogous to Example 215 starting from the compound obtained according to Preparation 166, the expected product is obtained in the form of a yellow oil (yield=77%).
$^1$H NMR (DMSOd$_6$, 300 MHz) δ=9.66 (s, 1H), 9.08 (d, 1H), 8.21 (d, 1H), 8.05 (m, 2H), 7.67 (d, 1H), 7.36 (dd, 1H), 6.86 (s, 1H), 5.03 (d, 1H), 4.93 (d, 1H), 4.23 (q, 1H), 4.10 (q, 2H), 1.31 (d, 3H), 1.17 (t, 3H).

Example 294

(2S)-2-[[5-chloro-1-[(6-benzothiazolyl)sulfonyl]-1H-indol-2-yl]methoxy]propanoic acid By following a procedure analogous to Example 2 starting from the compound obtained according to Example 293, the expected product is obtained in the form of a white solid (yield=66%).

M.p.=82° C.
$[\alpha]_D^{28}$=−41° (c=0.39; MeOH).

Example 295

(2R)-2-[[5-chloro-1-[(6-benzothiazolyl)sulfonyl]-1H-indol-2-yl]methoxy]propanoic acid methyl ester By following a procedure analogous to Example 215 starting from the compound obtained according to Preparation 168, the expected product is obtained in the form of a yellow oil (yield=80%).

$^1$H NMR (DMSOd$_6$, 300 MHz) δ=9.66 (s, 1H), 9.08 (d, 1H), 8.22 (d, 1H), 8.03 (m, 2H), 7.67 (d, 1H), 7.36 (dd, 1H), 6.86 (s, 1H), 5.03 (d, 1H), 4.92 (d, 1H), 4.27 (q, 1H), 3.66 (s, 3H), 1.32 (d, 3H).

Example 296

5-Chloro-1-[(2-methyl-7-benzothiazolyl)sulfonyl]-1H-indole-2-butanoic acid methyl ester By following a procedure analogous to Example 215 starting from the compound obtained according to Preparation 169, the expected product is obtained in the form of a yellow solid (yield=76%).

M.p.=129° C.

Example 297

5-Chloro-1-[(2-methyl-7-benzothiazolyl)sulfonyl]-1H-indole-2-butanoic acid

By following a procedure analogous to Example 2 starting from the compound obtained according to Example 296, the expected product is obtained in the form of a white powder (yield=93%).

M.p.=177-181° C.

Example 298

1-[(1-Acetyl-1H-indol-5-yl)sulfonyl]-5-chloro-1H-indole-2-butanoic acid methyl ester By following a procedure analogous to Example 215 starting from the compound obtained according to Preparation 170, the expected product is obtained in the form of a white powder (yield=89%).

M.p.=127-131° C.

Example 299

1-[(1H-indol-5-yl)sulfonyl]-5-chloro-1H-indole-2-butanoic acid

By following a procedure analogous to Example 2 starting from the compound obtained according to Example 298, the expected product is obtained in the form of a white solid (yield=52%).

M.p.=213° C.

Example 300

5-Chloro-1-[(2-methyl-7-benzothiazolyl)sulfonyl]-1H-indole-2-propanoic acid methyl ester By following a procedure analogous to Example 215 starting from the compound obtained according to Preparation 171, the expected product is obtained in the form of an amorphous solid (yield=70%).

$^1$H NMR (DMSOd$_6$, 300 MHz) δ=8.25 (dd, 1H), 7.93 (d, 1H), 7.76 (d, 1H), 7.68 (d, 1H), 7.63 (m, 1H), 7.30 (dd, 1H), 6.64 (s, 1H), 3.59 (s, 3H), 3.24 (t, 2H), 2.83 (s, 3H), 2.77 (t, 2H).

Example 301

5-Chloro-1-[(2-methyl-7-benzothiazolyl)sulfonyl]-1H-indole-2-propanoic acid

By following a procedure analogous to Example 2 starting from the compound obtained according to Example 300, the expected product is obtained in the form of a white powder (yield=86%).

M.p.=188-189° C.

Example 302

1-[(2-Amino-6-benzoxazolyl)sulfonyl]-5-chloro-1H-indole-2-propanoic acid methyl ester By following a procedure analogous to Example 215 starting from the compound obtained according to Preparation 172, the expected product is obtained in the form of a beige solid (yield=50%).

M.p.=190-195° C.

Example 303

1-[(2-Amino-6-benzoxazolyl)sulfonyl]-5-chloro-1H-indole-2-propanoic acid

By following a procedure analogous to Example 2 starting from the compound obtained according to Example 302, the expected product is obtained in the form of a white solid (yield=53%).

M.p.=242-249° C.

Example 304

5-Chloro-1-[(2,3-dihydro-5-benzofuranyl)sulfonyl]-1H-indole-2-propanoic acid methyl ester By following a procedure analogous to Example 215 starting from the compound obtained according to Preparation 173, the expected product is obtained in the form of an amorphous solid (yield=88%).

¹H NMR (DMSOd₆, 300 MHz) δ=8.02 (d, 1H), 7.70 (m, 1H), 7.63 (dd, 1H), 7.58 (d, 1H), 7.30 (dd, 1H), 6.89 (d, 1H), 6.56 (s, 1H), 4.60 (t, 2H), 3.62 (s, 3H), 3.28 (t, 2H), 3.18 (t, 2H), 2.81 (t, 2H).

Example 305

5-Chloro-1-[(2,3-dihydro-5-benzofuranyl)sulfonyl]-1H-indole-2-propanoic acid

By following a procedure analogous to Example 2 starting from the compound obtained according to Example 304, the expected product is obtained in the form of a white solid (yield=91%).
M.p.=170-171° C.

Example 306

1-[(2-Amino-6-benzothiazolyl)sulfonyl]-5-chloro-1H-indole-2-propanoic acid methyl ester By following a procedure analogous to Example 215 starting from the compound obtained according to Preparation 174, the expected product is obtained in the form of a yellow solid (yield=47%).
M.p.=217-222° C.

Example 307

1-[(2-Amino-6-benzothiazolyl)sulfonyl]-5-chloro-1H-indole-2-propanoic acid

By following a procedure analogous to Example 2 starting from the compound obtained according to Example 306, the expected product is obtained in the form of a white powder (yield=45%).
M.p.=250-255° C.

Example 308

2-[[[5-Chloro-1-(phenylsulfonyl)-1H-indol-2-yl]methyl]thio]-2-methylpropanoic acid By following a procedure analogous to Example 201 starting from the compound obtained according to Preparation 120 and 2-methyl-2-(2-propynylthio)propanoic acid, the expected product is obtained in the form of a beige solid (yield=14%).
M.p.=150-152° C.

Example 309

2-[[[5-Chloro-1-(phenylsulfonyl)-1H-indol-2-yl]methyl]thio]propanoic acid

By following a procedure analogous to Example 201 starting from the compound obtained according to Preparation 120 and 2-(2-propynylthio)propanoic acid, the expected product is obtained in the form of a white solid (yield=17%).
M.p.=138° C.

Example 310

2-[[[1-(Phenylsulfonyl)-5-(trifluoromethyl)-1H-indol-2-yl]methyl]thio]-2-methylpropanoic acid By following a procedure analogous to Example 201 starting from the compound obtained according to Preparation 121 and 2-methyl-2-(2-propynylthio)propanoic acid, the expected product is obtained in the form of a beige solid (yield=8%).
M.p.=90° C.

Example 311

2-[[[1-(Phenylsulfonyl)-5-(trifluoromethyl)-1H-indol-2-yl]methyl]thio]propanoic acid By following a procedure analogous to Example 201 starting from the compound obtained according to Preparation 121 and 2-(2-propynylthio)propanoic acid, the expected product is obtained in the form of a beige solid (yield=15%).
M.p.=120° C.

Example 312

1-[(6-Benzothiazolyl)sulfonyl]-5-methyl-1H-indole-2-butanoic acid methyl ester

By following a procedure analogous to Example 201 starting from the compound obtained according to Preparation 175 and the methyl ester of 5-hexynoic acid, the expected product is obtained in the form of a yellow powder (yield=47%).
M.p.=128-130° C.

Example 313

1-[(6-Benzothiazolyl)sulfonyl]-5-methyl-1H-indole-2-butanoic acid

By following a procedure analogous to Example 2 starting from the compound obtained according to Example 312, the expected product is obtained in the form of a yellow powder (yield=70%).
M.p.=128° C.

Example 314

1-(Phenylsulfonyl)-5-methyl-1H-indole-2-propanoic acid methyl ester

By following a procedure analogous to Example 201 starting from the compound obtained according to Preparation 176 and the methyl ester of 4-pentynoic acid, the expected product is obtained in the form of a beige solid (yield=13%).
M.p.=98-102° C.

Example 315

1-(Phenylsulfonyl)-5-methyl-1H-indole-2-propanoic acid

By following a procedure analogous to Example 2 starting from the compound obtained according to Example 314, the expected product is obtained in the form of a white powder (yield=59%).
M.p.=176-182° C.

Example 316

1-[(6-Benzothiazolyl)sulfonyl]-5-chloro-α,α-dimethyl-1H-indole-2-butanoic acid

By following a procedure analogous to Example 201 starting from the compound obtained according to Preparation 177 and 2,2-dimethyl-5-hexynoic acid, the expected product is obtained in the form of a yellow powder (yield=46%).

M.p.=151° C.

Example 317

5-Chloro-α,α-dimethyl-1-(phenylsulfonyl)-1H-indole-2-butanoic acid

By following a procedure analogous to Example 201 starting from the compound obtained according to Preparation 120 and 2,2-dimethyl-5-hexynoic acid, the expected product is obtained in the form of a brown solid (yield=32%).
M.p.=242° C.

Example 318

5-Chloro-1-[(2,3-dihydro-1H-indol-5-yl)sulfonyl]-1H-indole-2-propanoic acid

By following a procedure analogous to Example 2 starting from the compound obtained according to Example 158, the expected product is obtained in the form of a brown solid (yield=37%).
M.p.=157° C.

Example 319

5-Chloro-1-[(1H-indol-5-yl)sulfonyl]-1H-indole-2-propanoic acid

A solution of 40 mg (0.1 mM) of the compound obtained according to Example 318 in 4 ml of toluene is prepared and a solution of 22 mg (0.1 mM) of DDQ (2,3-dichloro-5,6-dicyano-1,4-benzoquinone) in 4 ml of toluene is added at the reflux temperature of the solvent. The reaction mixture is stirred for 12 hours at the reflux temperature of the solvent and then cooled, acidified by the addition of M hydrochloric acid solution and diluted with ethyl acetate. The organic phase is washed with sodium thiosulfate solution and then with water, dried over magnesium sulfate and concentrated under reduced pressure. The evaporation residue is purified by HPLC using an acetonitrile/water gradient mixture as the eluent to give the expected product in the form of a beige solid (yield=28%).
M.p.=79° C.

Example 320

5-Chloro-1-[[4-amino-3-(methylthio)phenyl]sulfonyl]-1H-indole-2-butanoic acid

A solution of 1 g (2.27 mM) of the compound obtained according to Example 117 in 16 ml of ethanol and 16 ml of 3.5 M aqueous potassium hydroxide solution is prepared. The mixture is stirred at room temperature for 5 hours, 0.9 ml of methyl iodide is then added and the reaction mixture is stirred again for 1 hour at room temperature. The medium is then diluted with 100 ml of water and acidified slowly with N hydrochloric acid solution. The precipitate formed is extracted with dichloromethane and the organic phase obtained is washed with water, dried over magnesium sulfate and concentrated under reduced pressure to give the expected product in the form of a crystalline white solid (yield=95%).
M.p.=158° C.

Example 321

5-Chloro-1-[(4-fluoro-3-nitrophenyl)sulfonyl]-1H-indole-2-butanoic acid methyl ester By following a procedure analogous to Example 215 starting from the compound obtained according to Preparation 178, the expected product is obtained in the form of a pale yellow powder (yield=96%).
M.p.=93° C.

Example 322

1-[(4-Amino-3-nitrophenyl)sulfonyl]-5-chloro-1H-indole-2-butanoic acid methyl ester A solution of 100 mg (0.22 mM) of the compound obtained according to Example 321 in 1 ml of dioxane is prepared and 0.77 ml of 32% aqueous ammonia is added. The mixture is stirred at room temperature for 30 min and then diluted with 8 ml of ethyl acetate, washed with water, dried over magnesium sulfate and concentrated under reduced pressure to give the expected product in the form of a pale yellow powder (yield=95%).
M.p.=157° C.

Example 323

5-Chloro-1-[(3,4-diaminophenyl)sulfonyl]-1H-indole-2-butanoic acid methyl ester

A suspension of 604 mg (1.33 mM) of the compound obtained according to Example 322 in 8 ml of acetic acid is prepared and 390 mg (7 mM) of iron powder are added, with stirring. The mixture is stirred at 60° C. for 1 hour and then diluted with water and ethyl acetate. The organic phase is separated off, filtered, washed with water, dried over magnesium sulfate and concentrated under reduced pressure to give the expected product in the form of a pale yellow powder (yield=70%).
M.p.=158-160° C.

Example 324

1-(1H-benzimidazol-5-ylsulfonyl)-5-chloro-1H-indole-2-butanoic acid methyl ester A suspension of 498 mg (1.18 mM) of the compound obtained according to Example 323 in 1.5 ml of formic acid is prepared. The mixture is stirred at 60° C. for 2 hours and then diluted with water, neutralized with 10 ml of N sodium hydroxide solution and extracted with ethyl acetate. The organic phase is separated off, washed with water, dried over magnesium sulfate and concentrated under reduced pressure. The crude product is purified by chromatography on silica gel using a toluene/isopropanol/aqueous ammonia mixture (85/15/1; v/v/v) as the eluent to give the expected product in the form of a beige foam (yield=83%).
$^1$H NMR (DMSOd$_6$, 300 MHz) δ=12.95 (s, 1H), 8.46 (s, 1H), 8.10 (m, 2H), 7.72 (d, 1H), 7.56 (m, 2H), 7.32 (dd, 1H), 7.19 (m, 2H), 6.58 (s, 1H), 3.58 (s, 3H), 3.05 (t, 2H), 2.45 (t, 2H), 1.99 (quin, 2H).

Example 325

1-(1H-benzimidazol-5-ylsulfonyl)-5-chloro-1H-indole-2-butanoic acid

By following a procedure analogous to Example 2 starting from the compound obtained according to Example 324, the expected product is obtained in the form of a white powder (yield=66%).
M.p.=212° C.

Example 326

5-Chloro-1-[(2,3-dihydro-1H-indol-5-yl)sulfonyl]-1H-indole-2-butanoic acid

By following a procedure analogous to Example 2 starting from the compound obtained according to Example 134, the expected product is obtained in the form of a beige solid (yield=19%).
M.p.=203° C.

The compounds according to the invention described above have been shown in the Tables below:

Table I collates compounds according to the invention in which X is a single bond and $R_3$ and $R_4$ are each a hydrogen atom.

Table II collates examples of compounds of formula I according to the invention in which X is an oxygen atom.

Table III collates examples of compounds of formula I according to the invention in which X is a sulfur atom.

Table IV collates the compounds in which X is a single bond and $R_3$ or $R_4$ is other than a hydrogen atom.

In these Tables, Ac represents an acetyl group.

TABLE I

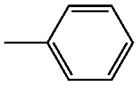

| Ex. | $R_a$ | $R_b$ | Ar | n | R |
|---|---|---|---|---|---|
| 1 | 5-Cl | H | 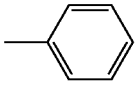 | 1 | $CH_3$ |
| 2 | 5-Cl | H | 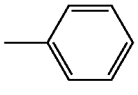 | 1 | H |
| 2a | 5-Cl | H | 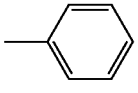 | 1 | Na |
| 3 | 5-$CF_3$ | H | 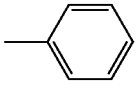 | 1 | $CH_3$ |
| 4 | 5-$CF_3$ | H | 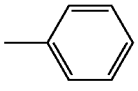 | 1 | H |
| 5 | 5-Br | H | 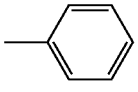 | 1 | $CH_3$ |
| 6 | 5-Br | H | 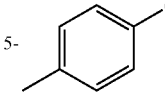 | 1 | H |
| 7 | 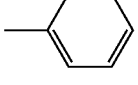 | H | 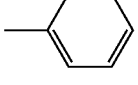 | 1 | $CH_3$ |

TABLE I-continued
![structure](indole with Ra, Rb, SO2Ar, (CH2)n-CH2-CO2R)
| Ex. | Rₐ | Rᵦ | Ar | n | R |
|---|---|---|---|---|---|
| 8 | 5-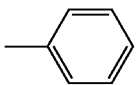(4-CF₃-phenyl) | H | 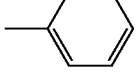phenyl | 1 | H |
| 9 | H | H | 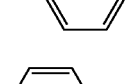phenyl | 1 | CH₃ |
| 10 | H | H | 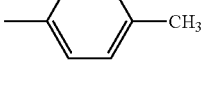phenyl | 1 | H |
| 11 | 5-Cl | H | 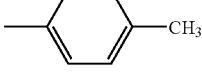4-CH₃-phenyl | 1 | CH₃ |
| 12 | 5-Cl | H | 4-CH₃-phenyl | 1 | H |
| 13 | 5-Cl | H | 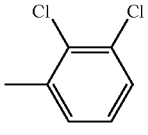2,3-diCl-phenyl | 1 | CH₃ |
| 14 | 5-Cl | H | 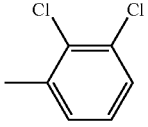2,3-diCl-phenyl | 1 | H |
| 15 | 5-Cl | H | 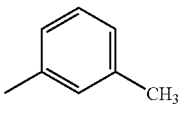3-CH₃-phenyl | 1 | CH₃ |
| 16 | 5-Cl | H | 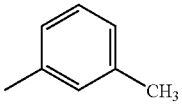3-CH₃-phenyl | 1 | H |
| 17 | 5-Cl | H | 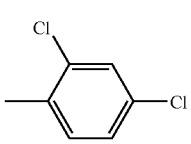2,4-diCl-phenyl | 1 | CH₃ |
| 18 | 5-Cl | H | 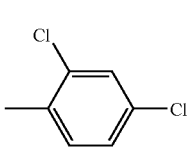2,4-diCl-phenyl | 1 | H |

TABLE I-continued
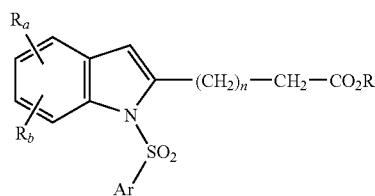
| Ex. | $R_a$ | $R_b$ | Ar | n | R |
|---|---|---|---|---|---|
| 19 | 5-Cl | H | 4-CF₃-C₆H₄ | 1 | CH₃ |
| 20 | 5-Cl | H | 4-CF₃-C₆H₄ | 1 | H |
| 21 | 5-Cl | H | 4-OMe-C₆H₄ | 1 | CH₃ |
| 22 | 5-Cl | H | 4-OMe-C₆H₄ | 1 | H |
| 23 | 5-Cl | H | 4-COCH₃-C₆H₄ | 1 | CH₃ |
| 24 | 5-Cl | H | 4-COCH₃-C₆H₄ | 1 | H |
| 25 | 5-Cl | H | 4-biphenyl | 1 | CH₃ |
| 26 | 5-Cl | H | 4-biphenyl | 1 | H |
| 27 | 5-Cl | H | 3-OMe-C₆H₄ | 1 | CH₃ |
| 28 | 5-Cl | H | 3-OMe-C₆H₄ | 1 | H |
| 29 | 5-Cl | H | 2,5-(OMe)₂-C₆H₃ | 1 | CH₃ |

TABLE I-continued
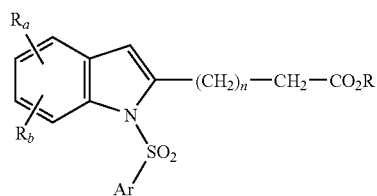
| Ex. | $R_a$ | $R_b$ | Ar | n | R |
|---|---|---|---|---|---|
| 30 | 5-Cl | H | 2,5-dimethoxy-4-methylphenyl (MeO, Me, OMe) | 1 | H |
| 31 | 5-Cl | H | 4-C(CH$_3$)$_3$-phenyl | 1 | CH$_3$ |
| 32 | 5-Cl | H | 4-C(CH$_3$)$_3$-phenyl | 1 | H |
| 33 | 5-Cl | H | 4-C$_2$H$_5$-phenyl | 1 | CH$_3$ |
| 34 | 5-Cl | H | 4-C$_2$H$_5$-phenyl | 1 | H |
| 35 | 5-Cl | H | 4-CH(CH$_3$)$_2$-phenyl | 1 | CH$_3$ |
| 36 | 5-Cl | H | 4-CH(CH$_3$)$_2$-phenyl | 1 | H |
| 37 | 5-Cl | H | 4-C$_3$H$_7$-phenyl | 1 | CH$_3$ |
| 38 | 5-Cl | H | 4-C$_3$H$_7$-phenyl | 1 | H |
| 39 | 5-Cl | H | 4-C$_5$H$_{11}$-phenyl | 1 | CH$_3$ |
| 40 | 5-Cl | H | 4-C$_5$H$_{11}$-phenyl | 1 | H |
| 41 | 5-Cl | H | 3,5-dimethylphenyl | 1 | CH$_3$ |

TABLE I-continued
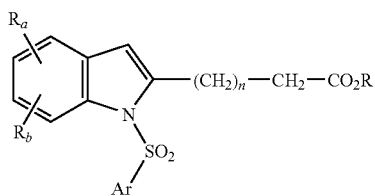
| Ex. | $R_a$ | $R_b$ | Ar | n | R |
|---|---|---|---|---|---|
| 42 | 5-Cl | H | 3,5-dimethylphenyl | 1 | H |
| 43 | 5-Cl | H | 2,3,5-trimethylphenyl | 1 | $CH_3$ |
| 44 | 5-Cl | H | 2,3,5-trimethylphenyl | 1 | H |
| 45 | 5-Cl | H | 4-chlorophenyl | 1 | $CH_3$ |
| 46 | 5-Cl | H | 4-chlorophenyl | 1 | H |
| 47 | 5-Cl | H | 4-fluorophenyl | 1 | $CH_3$ |
| 48 | 5-Cl | H | 4-fluorophenyl | 1 | H |
| 49 | 5-Cl | H | 4-chloro-3-methylphenyl | 1 | $CH_3$ |
| 50 | 5-Cl | H | 4-chloro-3-methylphenyl | 1 | H |
| 51 | 5-Cl | H | 3-(trifluoromethyl)phenyl | 1 | $CH_3$ |

TABLE I-continued

| Ex. | $R_a$ | $R_b$ | Ar | n | R |
|---|---|---|---|---|---|
| 52 | 5-Cl | H | 3-CF₃-phenyl | 1 | H |
| 53 | 5-Cl | H | 4-(NHCOCH₃)-phenyl | 1 | CH₃ |
| 54 | 5-Cl | H | 4-CN-phenyl | 1 | CH₃ |
| 55 | 5-Cl | H | 4-phenoxy-phenyl | 1 | CH₃ |
| 56 | 5-Cl | H | 4-phenoxy-phenyl | 1 | H |
| 57 | 5-Cl | H | naphthalen-1-yl | 1 | CH₃ |
| 58 | 5-Cl | H | naphthalen-1-yl | 1 | H |
| 59 | 5-Cl | H | naphthalen-2-yl | 1 | CH₃ |
| 60 | 5-Cl | H | naphthalen-2-yl | 1 | H |
| 61 | 5-Cl | H | 4,8-dimethyl-naphthalen-1-yl | 1 | CH₃ |
| 62 | 5-Cl | H | 4,8-dimethyl-naphthalen-1-yl | 1 | H |

TABLE I-continued

| Ex. | $R_a$ | $R_b$ | Ar | n | R |
|---|---|---|---|---|---|
| 63 | 5-Cl | H | 5-methyl-1-(NHCOCH₃)naphthalen-1-yl | 1 | CH₃ |
| 64 | 5-Cl | H | 5-methyl-1-(NHCOCH₃)naphthalen-1-yl | 1 | H |
| 65 | 5-Cl | H | 8-methylquinolin-1-yl | 1 | CH₃ |
| 66 | 5-Cl | H | 8-methylquinolin-1-yl | 1 | H |
| 67 | 5-Cl | H | phenyl | 2 | CH₃ |
| 68 | 5-Cl | H | phenyl | 2 | H |
| 69 | 5-Cl | H | 2,3-dichlorophenyl | 2 | CH₃ |
| 70 | 5-Cl | H | 2,3-dichlorophenyl | 2 | H |
| 71 | 5-Cl | H | 4-methoxyphenyl | 2 | CH₃ |
| 72 | 5-Cl | H | 4-methoxyphenyl | 2 | H |
| 73 | 5-Cl | H | 8-methylquinolin-1-yl | 2 | CH₃ |

TABLE I-continued
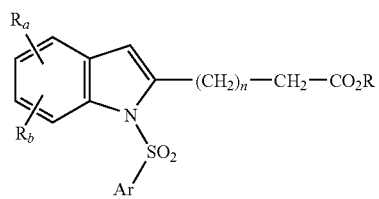
| Ex. | $R_a$ | $R_b$ | Ar | n | R |
|---|---|---|---|---|---|
| 74 | 5-Cl | H | 8-methylquinolin-yl | 2 | H |
| 75 | 5-Cl | H | 4-isopropylphenyl | 2 | $CH_3$ |
| 76 | 5-Cl | H | 4-isopropylphenyl | 2 | H |
| 77 | 5-Cl | H | naphthalen-2-yl | 2 | $CH_3$ |
| 78 | 5-Cl | H | naphthalen-2-yl | 2 | H |
| 79 | 5-Cl | H | 3,5-dimethylphenyl | 2 | $CH_3$ |
| 80 | 5-Cl | H | 3,5-dimethylphenyl | 2 | H |
| 81 | 5-Cl | H | 3-methoxyphenyl | 2 | $CH_3$ |
| 82 | 5-Cl | H | 3-methoxyphenyl | 2 | H |
| 83 | 5-Cl | H | 2,5-dimethoxyphenyl | 2 | $CH_3$ |

TABLE I-continued

| Ex. | R$_a$ | R$_b$ | Ar | n | R |
|---|---|---|---|---|---|
| 84 | 5-Cl | H | 2,5-dimethoxy-3-methylphenyl (MeO, OMe, Me-substituted phenyl) | 2 | H |
| 85 | 5-Cl | H | 1-methylnaphthyl | 2 | CH$_3$ |
| 86 | 5-Cl | H | 1-methylnaphthyl | 2 | H |
| 87 | 5-F | H | phenyl | 1 | CH$_3$ |
| 88 | 5-Cl | 6-Cl | phenyl | 1 | CH$_3$ |
| 89 | 5-Cl | 6-Cl | phenyl | 1 | H |
| 90 | 4-Cl | 6-Cl | phenyl | 1 | CH$_3$ |
| 91 | 4-Cl | 6-Cl | phenyl | 1 | H |
| 92 | 6-CF$_3$ | H | phenyl | 1 | CH$_3$ |
| 93 | 6-CF$_3$ | H | phenyl | 1 | H |
| 94 | 5-COCH$_3$ | H | phenyl | 1 | CH$_3$ |
| 95 | 5-COCH$_3$ | H | phenyl | 1 | H |
| 96 | 5-F | 6-Cl | phenyl | 1 | CH$_3$ |

TABLE I-continued
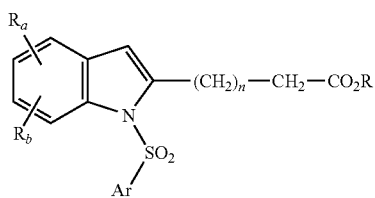
| Ex. | R$_a$ | R$_b$ | Ar | n | R |
|---|---|---|---|---|---|
| 97 | 5-F | 6-Cl | phenyl | 1 | H |
| 98 | 5-Cl | 7-Cl | phenyl | 1 | CH$_3$ |
| 99 | 5-Cl | 7-Cl | phenyl | 1 | H |
| 100 | 5-CN | H | phenyl | 1 | CH$_3$ |
| 101 | 5-CN | H | phenyl | 1 | H |
| 102 | 5-benzoyl | H | phenyl | 1 | CH$_3$ |
| 103 | 5-benzoyl | H | phenyl | 1 | H |
| 104 | 5-Cl | H | phenyl | 3 | CH$_3$ |
| 105 | 5-Cl | H | phenyl | 3 | H |
| 106 | 5-OCF$_3$ | H | phenyl | 1 | CH$_3$ |
| 107 | 5-OCF$_3$ | H | phenyl | 1 | H |
| 108 | 5-Cl | H | phenyl | 1 | —CH(CH$_3$)$_2$ |
| 109 | 5-Cl | H | 4-methyl-3,4-dihydro-2H-benzo[1,4]oxazin-7-yl | 2 | CH$_3$ |

TABLE I-continued
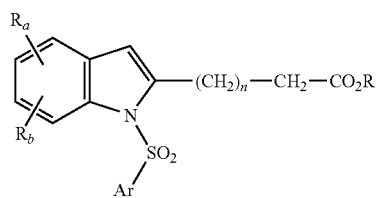
| Ex. | $R_a$ | $R_b$ | Ar | n | R |
|---|---|---|---|---|---|
| 110 | 5-Cl | H | | 2 | H |
| 111 | 5-Cl | H | | 2 | $CH_3$ |
| 112 | 5-Cl | H | | 2 | $CH_3$ |
| 113 | 5-Cl | H | | 2 | H |
| 114 | 5-Cl | H | | 2 | $CH_3$ |
| 115 | 5-Cl | H | | 2 | H |
| 116 | 5-Cl | H | | 2 | $CH_3$ |
| 117 | 5-Cl | H | | 2 | H |
| 118 | 5-Cl | H | | 2 | $CH_3$ |
| 119 | 5-Cl | H | | 2 | H |

TABLE I-continued

| Ex. | R$_a$ | R$_b$ | Ar | n | R |
|---|---|---|---|---|---|
| 120 | 5-Cl | H | 3,4,5-trimethylisoxazol-4-yl | 2 | CH$_3$ |
| 121 | 5-Cl | H | 3,4,5-trimethylisoxazol-4-yl | 2 | H |
| 122 | 5-Cl | H | 1,3,4,5-tetramethylpyrazol-4-yl | 2 | CH$_3$ |
| 123 | 5-Cl | H | 1,3,4,5-tetramethylpyrazol-4-yl | 2 | H |
| 124 | 5-Cl | H | 1,4-dimethylimidazol-5-yl | 2 | CH$_3$ |
| 125 | 5-Cl | H | 1,4-dimethylimidazol-5-yl | 2 | H |
| 126 | 5-Cl | H | 4-methyl-2,1,3-benzothiadiazol-5-yl | 2 | CH$_3$ |
| 127 | 5-Cl | H | 4-methyl-2,1,3-benzothiadiazol-5-yl | 2 | H |
| 128 | 5-Cl | H | 5-methyl-2,1,3-benzothiadiazol-6-yl | 2 | CH$_3$ |
| 129 | 5-Cl | H | 5-methyl-2,1,3-benzothiadiazol-6-yl | 2 | H |
| 130 | 5-Cl | H | 2,2,6-trimethylchroman-7-yl | 2 | CH$_3$ |

TABLE I-continued
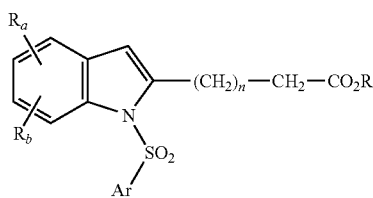
| Ex. | $R_a$ | $R_b$ | Ar | n | R |
|---|---|---|---|---|---|
| 131 | 5-Cl | H | 2,2-dimethyl-6-methylchroman | 2 | H |
| 132 | 5-Cl | H | 1,1,4,4-tetramethyl-6-methyltetralin | 2 | CH$_3$ |
| 133 | 5-Cl | H | 1,1,4,4-tetramethyl-6-methyltetralin | 2 | H |
| 134 | 5-Cl | H | 1-acetyl-5-methylindoline | 2 | CH$_3$ |
| 135 | 5-Cl | H | 1-acetyl-5-methylindoline | 2 | H |
| 136 | 5-Cl | H | 2,6-dimethylbenzothiazole | 2 | CH$_3$ |
| 137 | 5-Cl | H | 2,6-dimethylbenzothiazole | 2 | H |
| 138 | 5-Cl | H | 2-acetamido-6-methylbenzothiazole | 2 | CH$_3$ |
| 139 | 5-Cl | H | 2-acetamido-6-methylbenzothiazole | 2 | H |

TABLE I-continued

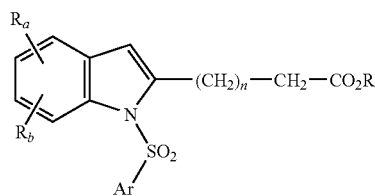

| Ex. | R_a | R_b | Ar | n | R |
|---|---|---|---|---|---|
| 140 | 5-Cl | H | 6-methyl-2-methyl-benzoxazole | 2 | $CH_3$ |
| 141 | 5-Cl | H | 5-methyl-2,3-dihydrobenzofuran | 2 | $CH_3$ |
| 142 | 5-Cl | H | 5-methyl-2,3-dihydrobenzofuran | 2 | H |
| 143 | 5-Cl | H | 5-methyl-2-methyl-benzothiazole | 2 | $CH_3$ |
| 144 | 5-Cl | H | 5-methyl-2-methyl-benzothiazole | 2 | H |
| 145 | 5-Cl | H | 6-methyl-2-amino-benzoxazole | 2 | $CH_3$ |
| 146 | 5-Cl | H | 6-methyl-2-amino-benzoxazole | 2 | H |
| 147 | 5-Cl | H | 4,5-dimethyl-2-acetamido-thiazole | 2 | $CH_3$ |
| 148 | 5-Cl | H | 4,5-dimethyl-2-acetamido-thiazole | 2 | H |
| 149 | 5-Cl | H | 6-methyl-3,4-dihydroquinolin-2(1H)-one | 2 | $CH_3$ |
| 150 | 5-Cl | H | 7-methyl-2-acetyl-1,2,3,4-tetrahydroisoquinoline | 2 | $CH_3$ |

TABLE I-continued

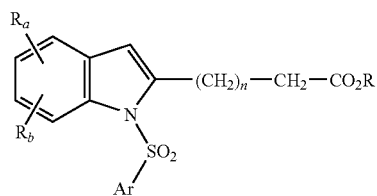

| Ex. | $R_a$ | $R_b$ | Ar | n | R |
|---|---|---|---|---|---|
| 151 | 5-Cl | H | 7-methyl-2-acetyl-1,2,3,4-tetrahydroisoquinolin-yl | 2 | H |
| 152 | 5-Cl | H | pyridin-2-yl-methyl | 2 | CH$_3$ |
| 153 | 5-Cl | H | pyridin-2-yl-methyl | 2 | H |
| 154 | 5-Cl | H | 6-methylbenzothiazol-2-yl | 1 | CH$_3$ |
| 155 | 5-Cl | H | 6-methylbenzothiazol-2-yl | 1 | H |
| 156 | 5-Cl | H | 6-methyl-2-acetamidobenzothiazol-yl | 1 | CH$_3$ |
| 157 | 5-Cl | H | 6-methyl-2-acetamidobenzothiazol-yl | 1 | H |
| 158 | 5-Cl | H | 5-methyl-1-acetylindolin-yl | 1 | CH$_3$ |
| 159 | 5-Cl | H | 5-methyl-1-acetylindolin-yl | 1 | H |
| 160 | 5-Cl | H | benzo[1,3]dioxol-5-yl-methyl | 1 | CH$_3$ |

TABLE I-continued

[Structure: indole with Ra, Rb substituents, N-SO2-Ar, and 2-(CH2)n-CH2-CO2R chain]

| Ex. | Ra | Rb | Ar | n | R |
|---|---|---|---|---|---|
| 161 | 5-Cl | H | methylenedioxyphenyl | 1 | H |
| 162 | 5-Cl | H | methylenedioxyphenyl | 2 | CH₃ |
| 163 | 5-Cl | H | methylenedioxyphenyl | 2 | H |
| 164 | 5-Cl | H | 4-(morpholinosulfonyl)phenyl | 2 | CH₃ |
| 165 | 5-Cl | H | 4-(morpholinosulfonyl)phenyl | 2 | H |
| 166 | 5-Cl | H | pyridin-2-yl | 1 | CH₃ |
| 167 | 5-Cl | H | pyridin-2-yl | 1 | H |
| 168 | 5-CF₃ | H | benzothiazol-6-yl | 2 | CH₃ |
| 169 | 5-CF₃ | H | benzothiazol-6-yl | 2 | H |
| 170 | 5-CF₃ | H | benzothiazol-6-yl | 1 | CH₃ |
| 171 | 5-CF₃ | H | benzothiazol-6-yl | 1 | H |
| 172 | 5-CF₃ | H | 2-methylbenzoxazol-6-yl | 2 | CH₃ |

TABLE I-continued

| Ex. | R$_a$ | R$_b$ | Ar | n | R |
|---|---|---|---|---|---|
| 173 | 5-CF$_3$ | H | 6-methyl-2-methyl-benzoxazole | 2 | H |
| 174 | 5-CF$_3$ | H | 1-acetyl-6-methyl-indoline | 2 | CH$_3$ |
| 174 | 5-CF$_3$ | H | 1-acetyl-6-methyl-indoline | 2 | H |
| 176 | 5-CF$_3$ | H | 5-methyl-2,3-dihydrobenzofuran | 2 | CH$_3$ |
| 177 | 5-CF$_3$ | H | 5-methyl-2,3-dihydrobenzofuran | 2 | H |
| 178 | 5-CF$_3$ | H | 5-methyl-2-methyl-benzothiazole | 2 | CH$_3$ |
| 179 | 5-CF$_3$ | H | 5-methyl-2-methyl-benzothiazole | 2 | H |
| 180 | 5-CF$_3$ | H | 6-methyl-2-amino-benzothiazole | 1 | CH$_3$ |
| 181 | 5-CF$_3$ | H | 6-methyl-2-amino-benzothiazole | 1 | H |
| 182 | 5-CF$_3$ | H | 6-methyl-2-methyl-benzothiazole | 1 | CH$_3$ |
| 183 | 5-CF$_3$ | H | 6-methyl-2-methyl-benzothiazole | 1 | H |

TABLE I-continued

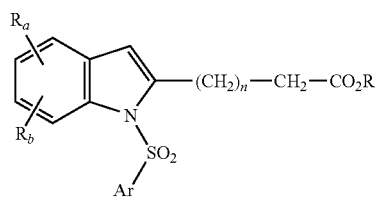

| Ex. | $R_a$ | $R_b$ | Ar | n | R |
|---|---|---|---|---|---|
| 184 | 5-CF$_3$ | H | 2,5-dimethylbenzothiazol-yl | 1 | CH$_3$ |
| 185 | 5-CF$_3$ | H | 2,5-dimethylbenzothiazol-yl | 1 | H |
| 186 | 5-CF$_3$ | H | 2,6-dimethylbenzoxazol-yl | 1 | CH$_3$ |
| 187 | 5-CF$_3$ | H | 2,7-dimethylbenzothiazol-yl | 1 | CH$_3$ |
| 188 | 5-CF$_3$ | H | 1-acetyl-5-methylindolin-yl | 1 | CH$_3$ |
| 189 | 5-CF$_3$ | H | 1-acetyl-5-methylindolin-yl | 1 | H |
| 190 | 5-CF$_3$ | H | 5-methyl-2,3-dihydrobenzofuran-yl | 1 | CH$_3$ |
| 191 | 5-CF$_3$ | H | 5-methyl-2,3-dihydrobenzofuran-yl | 1 | H |
| 192 | 5-CF$_3$ | H | 4-methylphenyl-morpholinosulfonyl | 1 | CH$_3$ |
| 193 | 5-CF$_3$ | H | 4-methylphenyl-morpholinosulfonyl | 1 | H |
| 194 | 5-Cl | H | 2-amino-6-methylbenzothiazol-yl | 2 | CH$_3$ |

TABLE I-continued

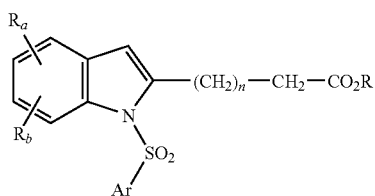

| Ex. | $R_a$ | $R_b$ | Ar | n | R |
|---|---|---|---|---|---|
| 195 | 5-Cl | H | 6-methyl-2-amino-benzothiazol-2-yl | 2 | H |
| 196 | 5-CF$_3$ | H | 5-methyl-indolin-1-yl | 2 | H |
| 197 | 5-CF$_3$ | H | 6-methyl-2-(acetylamino)-benzothiazol-2-yl | 2 | CH$_3$ |
| 198 | 5-CF$_3$ | H | 6-methyl-2-(acetylamino)-benzothiazol-2-yl | 2 | H |
| 199 | 5-CF$_3$ | H | 6-methyl-2-methyl-benzothiazol-2-yl | 2 | CH$_3$ |
| 200 | 5-CF$_3$ | H | 6-methyl-2-methyl-benzothiazol-2-yl | 2 | H |
| 225 | 5-CF$_3$ | H | 5-methyl-benzo[1,3]dioxol-5-yl | 2 | CH$_3$ |
| 226 | 5-CF$_3$ | H | 5-methyl-benzo[1,3]dioxol-5-yl | 2 | H |
| 227 | 5-CF$_3$ | H | 6-methyl-2-(acetylamino)-benzothiazol-2-yl | 1 | CH$_3$ |
| 228 | 5-CF$_3$ | H | 6-methyl-2-(acetylamino)-benzothiazol-2-yl | 1 | H |

TABLE I-continued

| Ex. | $R_a$ | $R_b$ | Ar | n | R |
|---|---|---|---|---|---|
| 296 | 5-Cl | H | 2-methyl-7-methylbenzothiazole | 2 | $CH_3$ |
| 297 | 5-Cl | H | 2-methyl-7-methylbenzothiazole | 2 | H |
| 298 | 5-Cl | H | 5-methyl-1-acetylindole | 2 | $CH_3$ |
| 299 | 5-Cl | H | 5-methylindole | 2 | H |
| 300 | 5-Cl | H | 2-methyl-7-methylbenzothiazole | 1 | $CH_3$ |
| 301 | 5-Cl | H | 2-methyl-7-methylbenzothiazole | 1 | H |
| 302 | 5-Cl | H | 2-amino-6-methylbenzoxazole | 1 | $CH_3$ |
| 303 | 5-Cl | H | 2-amino-6-methylbenzoxazole | 1 | H |
| 304 | 5-Cl | H | 5-methyl-2,3-dihydrobenzofuran | 1 | $CH_3$ |
| 305 | 5-Cl | H | 5-methyl-2,3-dihydrobenzofuran | 1 | H |
| 306 | 5-Cl | H | 2-amino-6-methylbenzothiazole | 1 | $CH_3$ |

TABLE I-continued
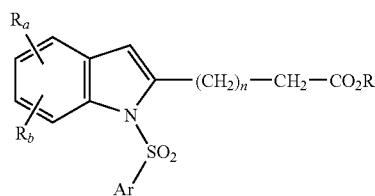
| Ex. | $R_a$ | $R_b$ | Ar | n | R |
|---|---|---|---|---|---|
| 307 | 5-Cl | H | 6-methyl-2-amino-benzothiazol-2-yl | 1 | H |
| 312 | 5-CH$_3$ | H | 6-methyl-benzothiazol-2-yl | 1 | CH$_3$ |
| 313 | 5-CH$_3$ | H | 6-methyl-benzothiazol-2-yl | 1 | H |
| 314 | 5-CH$_3$ | H | 4-methylphenyl | 1 | CH$_3$ |
| 315 | 5-CH$_3$ | H | 4-methylphenyl | 1 | H |
| 318 | 5-Cl | H | 5-methyl-indolin-2-yl | 1 | H |
| 319 | 5-Cl | H | 5-methyl-indol-2-yl | 1 | H |
| 320 | 5-Cl | H | 2-amino-5-methyl-3-(methylthio)phenyl | 2 | H |
| 321 | 5-Cl | H | 4-fluoro-3-nitro-phenyl | 2 | CH$_3$ |
| 322 | 5-Cl | H | 2-amino-5-methyl-3-nitro-phenyl | 2 | CH$_3$ |
| 323 | 5-Cl | H | 2,3-diamino-5-methyl-phenyl | 2 | CH$_3$ |

TABLE I-continued

Structure: indole with Ra, Rb substituents, N-SO2-Ar, and 2-(CH2)n-CH2-CO2R

| Ex. | Ra | Rb | Ar | n | R |
|---|---|---|---|---|---|
| 324 | 5-Cl | H | 5-methyl-1H-benzimidazol-2-yl | 2 | CH₃ |
| 325 | 5-Cl | H | 5-methyl-1H-benzimidazol-2-yl | 2 | H |
| 326 | 5-Cl | H | 5-methylindolin-2-yl | 2 | H |

TABLE II

Structure: indole with Ra, N-SO2-Ar, and 2-(CH2)n-O-C(R3)(R4)-COOR

| Ex. | Ra | n | R₃ | R₄ | Ar | R |
|---|---|---|---|---|---|---|
| 201 | 5-Cl | 1 | CH₃ | H | phenyl | C₂H₅ |
| 202 | 5-Cl | 1 | CH₃ | H | phenyl | H |
| 203 | 5-Cl | 1 | H | H | phenyl | CH₃ |
| 204 | 5-Cl | 1 | H | H | phenyl | H |
| 205 | 5-Cl | 1 | CH₃ | CH₃ | phenyl | CH₃ |
| 206 | 5-Cl | 1 | CH₃ | CH₃ | phenyl | H |
| 207 | 5-CF₃ | 1 | H | H | phenyl | CH₃ |
| 208 | 5-CF₃ | 1 | H | H | phenyl | H |
| 209 | 5-CF₃ | 1 | CH₃ | H | phenyl | C₂H₅ |
| 210 | 5-CF₃ | 1 | CH₃ | H | phenyl | H |
| 211 | 5-CF₃ | 1 | CH₃ | CH₃ | phenyl | CH₃ |
| 212 | 5-CF₃ | 1 | CH₃ | CH₃ | phenyl | H |
| 213 | 5-Cl | 2 | H | H | phenyl | C₂H₅ |
| 214 | 5-Cl | 2 | H | H | phenyl | H |

TABLE II-continued

| Ex. | $R_a$ | n | $R_3$ | $R_4$ | Ar | R |
|---|---|---|---|---|---|---|
| 215 | 5-Cl | 1 | $CH_3$ | $CH_3$ | 6-methylbenzothiazol-2-yl | $CH_3$ |
| 216 | 5-Cl | 1 | $CH_3$ | $CH_3$ | 6-methylbenzothiazol-2-yl | H |
| 217 | 5-$CF_3$ | 1 | $CH_3$ | $CH_3$ | 6-methylbenzothiazol-2-yl | $CH_3$ |
| 218 | 5-$CF_3$ | 1 | $CH_3$ | $CH_3$ | 6-methylbenzothiazol-2-yl | H |
| 219 | 5-Cl | 1 | $CH_3$ | $CH_3$ | 2,6-dimethylbenzothiazol-5-yl | $CH_3$ |
| 220 | 5-Cl | 1 | $CH_3$ | $CH_3$ | 2,6-dimethylbenzothiazol-5-yl | H |
| 221 | 5-Cl | 1 | $CH_3$ | $CH_3$ | 2,5-dimethylbenzothiazol-6-yl | $CH_3$ |
| 222 | 5-Cl | 1 | $CH_3$ | $CH_3$ | 2,5-dimethylbenzothiazol-6-yl | H |
| 223 | 5-Cl | 1 | $CH_3$ | H | 6-methylbenzothiazol-2-yl | $C_2H_5$ |
| 224 | 5-Cl | 1 | $CH_3$ | H | 6-methylbenzothiazol-2-yl | H |
| 229 | 5-$CF_3$ | 1 | $CH_3$ | $CH_3$ | 2,6-dimethylbenzothiazol-5-yl | $CH_3$ |
| 230 | 5-$CF_3$ | 1 | $CH_3$ | $CH_3$ | 2,6-dimethylbenzothiazol-5-yl | H |
| 231 | 5-$CF_3$ | 1 | $CH_3$ | $CH_3$ | 6-methylbenzo[1,3]dioxol-5-yl | $CH_3$ |
| 232 | 5-$CF_3$ | 1 | $CH_3$ | $CH_3$ | 6-methylbenzo[1,3]dioxol-5-yl | H |
| 233 | 5-$CF_3$ | 1 | $CH_3$ | $CH_3$ | 2-acetamido-6-methylbenzothiazol-5-yl | $CH_3$ |
| 234 | 5-$CF_3$ | 1 | $CH_3$ | $CH_3$ | 2-acetamido-6-methylbenzothiazol-5-yl | H |
| 235 | 5-$CF_3$ | 1 | $CH_3$ | $CH_3$ | 5-methyl-2,3-dihydrobenzofuran-6-yl | $CH_3$ |
| 236 | 5-$CF_3$ | 1 | $CH_3$ | $CH_3$ | 5-methyl-2,3-dihydrobenzofuran-6-yl | H |
| 237 | 5-$CF_3$ | 1 | $CH_3$ | $CH_3$ | 2,7-dimethylbenzothiazol-?-yl | $CH_3$ |
| 238 | 5-$CF_3$ | 1 | $CH_3$ | $CH_3$ | 2,7-dimethylbenzothiazol-?-yl | H |
| 239 | 5-$CF_3$ | 1 | $CH_3$ | $CH_3$ | 7-methyl-2,3-dihydrobenzo[1,4]dioxin-6-yl | $CH_3$ |
| 240 | 5-$CF_3$ | 1 | $CH_3$ | $CH_3$ | 7-methyl-2,3-dihydrobenzo[1,4]dioxin-6-yl | H |
| 241 | 5-$CF_3$ | 1 | $CH_3$ | $CH_3$ | 4,7-dimethyl-3,4-dihydro-2H-benzo[1,4]oxazin-6-yl | $CH_3$ |

TABLE II-continued

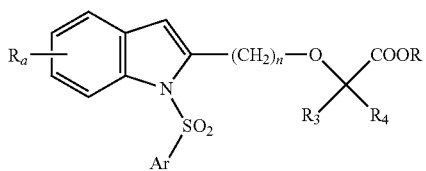

| Ex. | $R_a$ | n | $R_3$ | $R_4$ | Ar | R |
|---|---|---|---|---|---|---|
| 242 | 5-CF$_3$ | 1 | CH$_3$ | CH$_3$ | 4-methyl-N-methyl-benzomorpholinyl | H |
| 243 | 5-CF$_3$ | 1 | CH$_3$ | CH$_3$ | 5-methyl-N-Ac-indolinyl | CH$_3$ |
| 244 | 5-CF$_3$ | 1 | CH$_3$ | CH$_3$ | 5-methyl-N-Ac-indolinyl | H |
| 245 | 5-CF$_3$ | 1 | CH$_3$ | CH$_3$ | 3,5-dimethylphenyl | CH$_3$ |
| 246 | 5-CF$_3$ | 1 | CH$_3$ | CH$_3$ | 3,5-dimethylphenyl | H |
| 247 | 5-CF$_3$ | 1 | CH$_3$ | CH$_3$ | 2,5-dimethoxy-4-methylphenyl | CH$_3$ |
| 248 | 5-CF$_3$ | 1 | CH$_3$ | CH$_3$ | 2,5-dimethoxy-4-methylphenyl | H |
| 249 | 5-CF$_3$ | 1 | CH$_3$ | CH$_3$ | 4-isopropylphenyl | CH$_3$ |
| 250 | 5-CF$_3$ | 1 | CH$_3$ | CH$_3$ | 4-isopropylphenyl | H |
| 251 | 5-Cl | 1 | CH$_3$ | CH$_3$ | 5-methylbenzo[1,3]dioxolyl | CH$_3$ |

TABLE II-continued

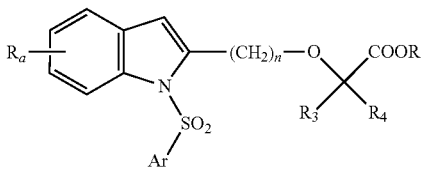

| Ex. | $R_a$ | n | $R_3$ | $R_4$ | Ar | R |
|---|---|---|---|---|---|---|
| 252 | 5-Cl | 1 | CH$_3$ | CH$_3$ | 5-methylbenzo[1,3]dioxolyl | H |
| 253 | 5-Cl | 1 | CH$_3$ | CH$_3$ | 6-methyl-2-NHAc-benzothiazolyl | CH$_3$ |
| 254 | 5-Cl | 1 | CH$_3$ | CH$_3$ | 6-methyl-2-NHAc-benzothiazolyl | H |
| 255 | 5-Cl | 1 | CH$_3$ | CH$_3$ | 5-methyl-N-Ac-indolinyl | CH$_3$ |
| 256 | 5-Cl | 1 | CH$_3$ | CH$_3$ | 5-methyl-N-Ac-indolinyl | H |
| 257 | 5-Cl | 1 | CH$_3$ | CH$_3$ | 5-methyl-2,3-dihydrobenzofuranyl | CH$_3$ |
| 258 | 5-Cl | 1 | CH$_3$ | CH$_3$ | 5-methyl-2,3-dihydrobenzofuranyl | H |
| 259 | 5-Cl | 1 | CH$_3$ | CH$_3$ | 7-methyl-2-methylbenzothiazolyl | CH$_3$ |
| 260 | 5-Cl | 1 | CH$_3$ | CH$_3$ | 7-methyl-2-methylbenzothiazolyl | H |
| 261 | 5-Cl | 1 | CH$_3$ | CH$_3$ | 7-methyl-2,3-dihydrobenzo[1,4]dioxinyl | CH$_3$ |
| 262 | 5-Cl | 1 | CH$_3$ | CH$_3$ | 7-methyl-2,3-dihydrobenzo[1,4]dioxinyl | H |

TABLE II-continued

Structure: $R_a$-indole-2-(CH$_2$)$_n$-O-C(R$_3$)(R$_4$)-COOR, with N-SO$_2$-Ar

| Ex. | R$_a$ | n | R$_3$ | R$_4$ | Ar | R |
|---|---|---|---|---|---|---|
| 263 | 5-Cl | 1 | CH$_3$ | CH$_3$ | 7-methyl-4-methyl-3,4-dihydro-2H-benzo[1,4]oxazine | CH$_3$ |
| 264 | 5-Cl | 1 | CH$_3$ | CH$_3$ | 7-methyl-4-methyl-3,4-dihydro-2H-benzo[1,4]oxazine | H |
| 265 | 5-Cl | 1 | CH$_3$ | CH$_3$ | 4-isopropylphenyl | CH$_3$ |
| 266 | 5-Cl | 1 | CH$_3$ | CH$_3$ | 4-isopropylphenyl | H |
| 267 | 5-Cl | 1 | CH$_3$ | CH$_3$ | 3,5-dimethylphenyl | CH$_3$ |
| 268 | 5-Cl | 1 | CH$_3$ | CH$_3$ | 3,5-dimethylphenyl | H |
| 269 | 5-Cl | 1 | CH$_3$ | CH$_3$ | 2,5-dimethoxy-methylphenyl | CH$_3$ |
| 270 | 5-Cl | 1 | CH$_3$ | CH$_3$ | 2,5-dimethoxy-methylphenyl | H |
| 271 | 5-Cl | 1 | CH$_3$ | CH$_3$ | 4-methoxyphenyl | CH$_3$ |
| 272 | 5-Cl | 1 | CH$_3$ | CH$_3$ | 4-methoxyphenyl | H |
| 273 | 5-Cl | 1 | CH$_3$ | H | 2,6-methylbenzothiazole | C$_2$H$_5$ |
| 274 | 5-Cl | 1 | CH$_3$ | H | 2,6-methylbenzothiazole | H |
| 275 | 5-Cl | 1 | CH$_3$ | H | 6-methyl-2,3-dihydrobenzo[1,4]dioxine | C$_2$H$_5$ |
| 276 | 5-Cl | 1 | CH$_3$ | H | 6-methyl-2,3-dihydrobenzo[1,4]dioxine | H |
| 277 | 5-Cl | 1 | CH$_3$ | H | 7-methyl-4-methyl-3,4-dihydro-2H-benzo[1,4]oxazine | C$_2$H$_5$ |
| 278 | 5-Cl | 1 | CH$_3$ | H | 7-methyl-4-methyl-3,4-dihydro-2H-benzo[1,4]oxazine | H |
| 279 | 5-Cl | 1 | CH$_3$ | H | 3,4,5-trimethylisoxazole | C$_2$H$_5$ |
| 280 | 5-Cl | 1 | CH$_3$ | H | 3,4,5-trimethylisoxazole | H |
| 281 | 5-Cl | 1 | CH$_3$ | H | 2,5-dimethoxy-methylphenyl | C$_2$H$_5$ |
| 282 | 5-Cl | 1 | CH$_3$ | H | 2,5-dimethoxy-methylphenyl | H |
| 283 | 5-CF$_3$ | 1 | CH$_3$ | H | 2,6-methylbenzothiazole | C$_2$H$_5$ |
| 284 | 5-CF$_3$ | 1 | CH$_3$ | H | 2,6-methylbenzothiazole | H |

TABLE II-continued

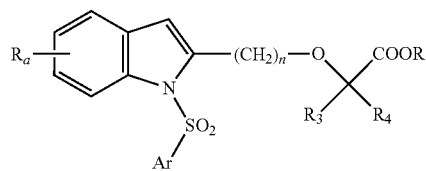

| Ex. | $R_a$ | n | $R_3$ | $R_4$ | Ar | R |
|---|---|---|---|---|---|---|
| 285 | 5-CF$_3$ | 1 | CH$_3$ | H | 6-methylbenzothiazol-2-yl | C$_2$H$_5$ |
| 286 | 5-CF$_3$ | 1 | CH$_3$ | H | 6-methylbenzothiazol-2-yl | H |
| 287 | 5-CF$_3$ | 1 | CH$_3$ | H | 7-methyl-2,3-dihydro-1,4-benzodioxin-6-yl | C$_2$H$_5$ |
| 288 | 5-CF$_3$ | 1 | CH$_3$ | H | 7-methyl-2,3-dihydro-1,4-benzodioxin-6-yl | H |
| 289 | 5-CF$_3$ | 1 | CH$_3$ | H | 4-methyl-7-methyl-3,4-dihydro-2H-benzo[1,4]oxazin-6-yl | C$_2$H$_5$ |
| 290 | 5-CF$_3$ | 1 | CH$_3$ | H | 4-methyl-7-methyl-3,4-dihydro-2H-benzo[1,4]oxazin-6-yl | H |
| 291 | 5-CF$_3$ | 1 | CH$_3$ | H | 2,4-dimethoxy-5-methylphenyl | C$_2$H$_5$ |
| 292 | 5-CF$_3$ | 1 | CH$_3$ | H | 2,4-dimethoxy-5-methylphenyl | H |
| 293 | 5-Cl (S) | 1 | CH$_3$ | H | 6-methylbenzothiazol-2-yl | C$_2$H$_5$ |
| 294 | 5-Cl (S) | 1 | CH$_3$ | H | 6-methylbenzothiazol-2-yl | H |
| 295 | 5-Cl (R) | 1 | CH$_3$ | H | 6-methylbenzothiazol-2-yl | C$_2$H$_5$ |

TABLE III

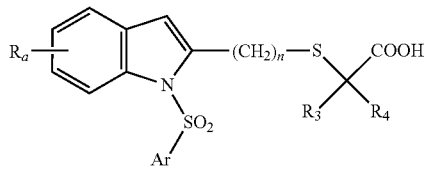

| Ex. | $R_a$ | N | $R_3$ | $R_4$ | Ar |
|---|---|---|---|---|---|
| 308 | 5-Cl | 1 | CH$_3$ | CH$_3$ | p-tolyl |
| 309 | 5-Cl | 1 | CH$_3$ | H | p-tolyl |
| 310 | 5-CF$_3$ | 1 | CH$_3$ | CH$_3$ | p-tolyl |
| 311 | 5-CF$_3$ | 1 | CH$_3$ | H | p-tolyl |

TABLE IV

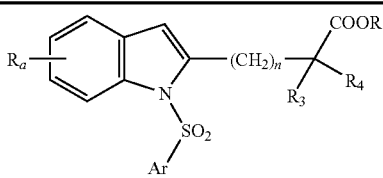

| Ex. | $R_a$ | n | $R_3$ | $R_4$ | Ar | R |
|---|---|---|---|---|---|---|
| 316 | 5-Cl | 2 | CH$_3$ | CH$_3$ | 6-methylbenzothiazol-2-yl | H |
| 317 | 5-Cl | 2 | CH$_3$ | CH$_3$ | p-tolyl | H |

Pharmacological Activity

The compounds of the invention were subjected to biological tests in order to evaluate their potential for treating or preventing certain pathological conditions. The first step was to measure the ability of the compounds to behave as PPAR nuclear receptor activators.

A transactivation test is used as a primary screening test. Cos-7 cells are transfected with a plasmid expressing a chimera of a PPAR-Gal4 murine or human receptor (PPARα-Gal4, PPARδ-Gal4 or PPARγ-Gal4 receptor) and a 5Gal4pGL3 TK Luc reporter plasmid. The transfections are carried out with the aid of a chemical agent (Jet PEI).

The transfected cells are distributed over 384-well plates and left to stand for 24 hours.

After 24 hours the culture medium is changed. The test products are added (final concentration of between $3.10^{-5}$ and $3.10^{-10}$ M) to the culture medium. After incubation overnight, the expression of luciferase is measured after the addition of "SteadyGlo" according to the instructions provided by the manufacturer (Promega).

$10^{-5}$ M fenofibric acid (PPARα agonist), $10^{-8}$ M GW501516 (PPARδ agonist) and $10^{-6}$ M rosiglitazone (PPARγ agonist) are used as references.

The results are expressed as the induction rate (number of times) compared with the basal level in percentage activity of the appropriate reference (reference=100%). The effect-concentration curves and the $EC_{50}$ values are calculated using the Assay Explorer software (MDL).

In micromolar concentration, the compounds according to the invention have an induction rate ranging up to 154% (PPARα), 127% (PPARδ) and 100% (PPAR-γ). Some compounds according to the invention have an $EC_{50}$ below 50 nM, especially the hPPARδ receptor.

A second series of tests was performed with the compounds according to the invention in order to confirm the activity deduced from their affinity for the aforementioned receptors. This test consists in measuring the β-oxidation on HuH7 cells of human hepatic origin and C2C12 cells of murine muscular origin after differentiation in myotubes.

The cells are inoculated into Petri dishes containing a central well. The products are added to the culture medium and incubated for 48 hours at different concentrations. After incubation for 22 hours, C14-radiolabeled oleate (1-C14 oleate) is added to the culture medium. The β-oxidation reaction is stopped 2 hours later by the addition of 40% perchloric acid.

The $CO_2$ liberated during the oxidation of the oleate is trapped with KOH solution and then counted.

Each test is performed three times.

The results are expressed in % variation relative to the control dishes (dishes without compounds).

According to this test, the compounds according to the invention increase the β-oxidation up to +148% at a concentration of 10 μM on HuH7 cells. The β-oxidation is also increased by 82% in the presence of, for example, the compound according to Example 4 used at a concentration of 100 μM in a test on C2C12 cells.

Some compounds according to the invention were tested in a db/db mouse model in order to confirm their potential as active principles. The test protocol is as follows:

Homozygous C57BL/Ks-db male mice (db/db mice), 11 to 13 weeks old at the start of the studies, are divided up into groups of 9-10 animals. The products are administered orally once a day for 5 days. One group of mice receives the vehicle only (0.5 or 1% methyl cellulose solution). A blood sample is taken from the retro-orbital sinus before treatment and 4 hours after the last gavage.

After centrifugation, the serum is collected and the cholesterol, triglyceride and glucose levels are measured using a multiparameter analyzer with commercial kits.

The results are expressed in % variation on the final day relative to the control group.

As examples of the compounds according to the invention, the following comparative results are obtained:

| Compound | Dose (mg/kg) | Glucose | Triglycerides | Cholesterol |
|---|---|---|---|---|
| Fenofibrate | 100 | −9 | −7 | +32 |
| Rosiglitazone | 3 | −41 | −52 | −30 |
| Ex. 2 | 30 | 0 | −7 | +30 |
| Ex. 4 | 30 | −30 | −12 | +41 |
| Ex. 155 | 30 | −35 | −41 | +38 |
| Ex. 163 | 30 | −38 | −35 | −15 |
| Ex. 202 | 30 | −52 | −48 | +25 |

These results, which are in agreement with the modifications expected of PPARα and/or PPARδ nuclear receptor activators, confirm the value of the compounds according to the invention for use as active principles of drugs for preventing or treating hypertriglyceridemia and hypercholesterolemia and, more generally, for re-establishing normal parameters in the event of a perturbation of the lipid and carbohydrate metabolism. The compounds according to the invention are also useful in the treatment of endothelial dysfunction, inflammatory disease or neurodegeneration.

The invention further relates to the pharmaceutical compositions intended for the prevention or treatment of the aforesaid diseases when they contain at least one of the compounds of formula I according to the invention as the active principle.

These pharmaceutical compositions can be prepared in conventional manner using pharmaceutically acceptable excipients to give forms that can preferably be administered orally, e.g. tablets or capsules.

In practical terms, if the compound is administered orally, the daily dosage in humans will preferably be between 5 and 500 mg.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating a condition selected from the group consisting of hypertriglyceridemia, hyperlipidemia, hypercholesterolemia, dyslipidemia, obesity, insulin resistence, diabetes, atherosclerosis, myocardial infarction, hypertension, cerebral vascular disease, rheumatoid arthritis, Alzheimer's disease, and Parkinson's disease in a subject in need thereof, said method comprising administering to said subject a pharmacologically effective amount of a compound corresponding to formula I:

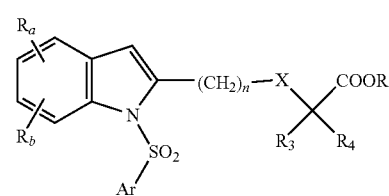

(I)

wherein $R_a$ and $R_b$ are independently selected from the group consisting of hydrogen, halogen, $C_1$-$C_6$ alkyl, $CF_3$, CN, CO—$R_2$, $OR_2$ and phenyl optionally substituted by $C_1$-$C_4$ alkyl or $CF_3$;

$R_2$ is $C_1$-$C_4$ alkyl, $CF_3$ or phenyl optionally substituted by $C_1$-$C_4$ alkyl or $CF_3$;

$R_3$ and $R_4$ are independently hydrogen or $C_1$-$C_4$ alkyl;

R is hydrogen or $C_1$-$C_3$ alkyl;

n is 1, 2 or 3;

X is a single bond, an oxygen atom or a sulfur atom; and

Ar is an aromatic or heteroaromatic ring selected from the group consisting of phenyl, naphthyl, quinolinyl, isoquinolinyl, pyridinyl, pyrazolyl, imidazolyl, isoxazolyl, thiazolyl, benzimidazolyl, benzothiazolyl, 2,1,3-benzothiadiazolyl, 3,4-dihydro-1,4-benzoxazinyl, 5,6,7,8- tetrahydronaphthalenyl, 1,2,3,4-tetrahydroquinolinyl, 1,2,3,4-tetrahydroiso-quinolinyl, 1,2,3,4-tetrahydro-2-oxoquinolinyl, 3,4-dihydro-2H-benzopyranyl, indolyl, 2,3-dihydroindolyl, benzofuranyl, 2,3-dihydrobenzofuranyl, 1,3-benzodioxolyl, 1,4-benzodioxanyl and benzoxazolyl optionally substituted by one or more substituents selected from the group consisting of halogen, $C_1$-$C_6$ alkyl, phenyl, $CF_3$, CN, CO—$R_2$, $OR_2$, $SR_2$, NH—$COR_2$, morpholinyl, amino and 4-morpholinosulfonyl;

or a pharmaceutically acceptable salt thereof.

2. A method according to claim 1, wherein said condition is selected from the group consisting of hypertriglyceridemia, hyperlipidemia, hypercholesterolemia, obesity and diabetes.

3. A method according to claim 1, wherein said condition is neurodegeneration selected from the group consisting of Alzheimer's disease and Parkinson's disease.

\* \* \* \* \*